(12) United States Patent
Harrow et al.

(10) Patent No.: US 6,878,529 B2
(45) Date of Patent: Apr. 12, 2005

(54) COMPOUNDS FOR THE TREATMENT OF SEXUAL DYSFUNCTION

(75) Inventors: Ian Dennis Harrow, Kent (GB); Peter Stacey, Kent (GB); Roderick Thomas Walsh, Kent (GB); Christopher Peter Wayman, Kent (GB); Stephen Charles Phillips, Kent (GB)

(73) Assignee: Pfizer Inc., New York, NY (US)

( * ) Notice: Subject to any disclaimer, the term of this patent is extended or adjusted under 35 U.S.C. 154(b) by 230 days.

(21) Appl. No.: 09/905,846

(22) Filed: Jul. 13, 2001

(65) Prior Publication Data

US 2002/0102707 A1 Aug. 1, 2002

Related U.S. Application Data

(60) Provisional application No. 60/220,908, filed on Jul. 26, 2000.

(30) Foreign Application Priority Data

Jul. 14, 2000 (GB) .............................................. 0017387

(51) Int. Cl.[7] ......................... C12N 15/12; C12N 15/52; C12N 15/57; C12N 15/63; C12N 15/79
(52) U.S. Cl. .............. 435/69.1; 435/252.3; 435/252.33; 435/254.11; 435/320.1; 435/410; 435/455; 435/468; 435/471; 536/23.2; 536/23.5
(58) Field of Search ............................. 435/325, 252.3, 435/252.33, 254.11, 410, 455, 468, 471, 320.1, 69.1; 536/23.5, 23.2

(56) References Cited

U.S. PATENT DOCUMENTS

2002/0102707 A1 * 8/2002 Harrow et al. .............. 435/226

FOREIGN PATENT DOCUMENTS

| EP | 1069188 | 1/2000 |
|---|---|---|
| WO | WO9953077 | 10/1999 |
| WO | WO0047750 | 8/2000 |

OTHER PUBLICATIONS

Kinzler et al., "Whole genome PCR: application to the identification of sequences bound by gene regulatory proeins," Nucl. Acids Res. 17 (10): 3645–3653, 1989.*
GenBank Acc. No. AW372628, US National Library of Medicine, Bethesda, MD, Feb. 4, 2000, accessed by PTO on Oct. 24, 2003.*
GenBank Acc. No. AW955378, US National Library of Medicine, Bethesda, MD, Jun. 1, 2000, accessed by PTO on Oct. 24, 2003.*
GenBank Acc. No. AI422225, US National Library of Medicine, Bethesda, MD, Mar. 30, 1999, accessed by PTO on Oct. 24, 2003.*
GenBank Acc. No. R54681, US National Library of Medicine, Bethesda, MD, May 22, 1995, accessed by PTO on Oct. 24, 2003.*
Rudinger, J., "Characteristics of the amino acids components of a peptide hormone sequence," in Peptide Hormones, Parsons (ed.), University Park Press: Baltimore, MD, pp. 1–7, 1976.*
GenBank Acc. No. AF067196, US National Library of Medicine, Bethesda, MD, Jul. 1, 1998, accessed by PTO on Oct. 29, 2003.*
Kennell, D.E. "Principles and practices of nucleic acid hybridization," Progr. Nucl. Acid Res. Mol. Biol. 11: 259–301, 1971.*
Ngo et al., "Computational complexity, protein structure prediction, and the Levinthal paradox," in The Protein Folding Problem and Tertiary Structure Prediction, Merz et al. (eds.), Birkhauser Boston: Boston, MA, pp. 433 and 492–495, 1994.*
Ikeda, K., et al. *The Journal of Biological Chemistry*, vol. 274, No. 5: pp. 32469–32477, 1999.
Ghaddar, G., et al., *Biochem. J.*, vol. 347: pp. 419–429, 2000.

* cited by examiner

Primary Examiner—Scott D. Priebe
(74) Attorney, Agent, or Firm—Peter C. Richardson; Gregg C. Benson; Deborah A. Martin

(57) ABSTRACT

Polynucleotide and polypeptide sequences are described. The polypeptide sequences comprise one or more of: (a) a polypeptide having the deduced amino acid sequence translated from the polynucleotide sequence in SEQ ID NO: 1 or SEQ ID NO: 5 and variants, fragments, homologues, analogues and derivatives thereof; (b) a polypeptide of SEQ ID NO: 2 and variants, fragments, homologues, analogues and derivatives thereof (c) a polypeptide encoded by the cDNA of NCIMB 41110 and variants, fragments, homologues, analogues and derivatives thereof; or (d) a polypeptide which has at least 78% identity to (i) the polypeptide encoded by the polynucleotide of SEQ ID NO: 1 or SEQ ID NO: 5, (ii) the polypeptide of SEQ ID NO: 2, or (iii) the polypeptide encoded by the cDNA of NCIMB 41110. Such polypeptide sequences are, inter alia, useful in the prophylaxis and/or treatment of sexual dysfunction, in particular male erectile dysfunction (MED) or female sexual dysfunction (FSD), preferably female sexual arousal disorder (FSAD).

5 Claims, 26 Drawing Sheets

Figure 1A

Analysis of open reading frames (ORFs) of human SEP cDNA sequence

```
            10         20         30         40         50         60
    .........|.........|.........|.........|.........|.........|
    ggcaccagctcagccccaagccactgctctcccatcccagtccctggaaatccacccact
    G..T..S..S..A..P..S..H..C..S..P..I..P..V..P..G..N..P..P..T..
    A..P..A..Q..P..Q..A..T..A..L..P..S..Q..S..L..E..I..H..P..L..
    H..Q..L..S..P..K..P..L..L..S..H..P..S..P..W..K..S..T..H..L..

70         80         90        100        110        120
    .........|.........|.........|.........|.........|.........|
    tggcccagctcaccccaactccaacccactgggacccagtctccaggggcctgactgtgg
    W..P..S..S..P..Q..L..Q..P..T..G..T..Q..S..P..G..A..*..L..W..
    G..P..A..H..P..N..S..N..P..L..G..P..S..L..Q..G..P..D..C..G..
    A..Q..L..T..P..T..P..T..H..W..D..P..V..S..R..G..L..T..V..G..

130        140        150        160        170        180
    .........|.........|.........|.........|.........|.........|
    gcggcagccactcctgagtgagcaaaggttcctccgcggtgctctcccgtccagagccct
    A..A..A..T..P..E..*..A..K..V..P..P..R..C..S..P..V..Q..S..P..
    R..Q..P..L..L..S..E..Q..R..F..L..R..G..A..L..P..S..R..A..L..
    G..S..H..S..*..V..S..K..G..S..S..A..V..L..S..R..P..E..P..C..

190        200        210        220        230        240
    .........|.........|.........|.........|.........|.........|
    gctgatggggaagtccgaaggccccgtggggatggtggagagcgctggccgtgcagggca
    A..D..G..E..V..R..R..P..R..G..D..G..G..E..R..W..P..C..R..A..
    L..M..G..K..S..E..G..P..V..G..M..V..E..S..A..G..R..A..G..Q..
    *..W..G..S..P..K..A..P..W..G..W..W..R..A..L..A..V..Q..G..R..

250        260        270        280        290        300
    .........|.........|.........|.........|.........|.........|
    gaagcgcccggggttcctggagggggggctgctgctgctgctgctgctggtgaccgctgc
    E..A..P..G..V..P..G..G..G..A..A..A..A..A..A..A..G..D..R..C..
    K..R..P..G..F..L..E..G..G..L..L..L..L..L..L..L..V..T..A..A..
    S..A..R..G..S..W..R..G..G..C..C..C..C..C..C..W..*..P..L..P..
```

Figure 1b

```
         310       320       330       340       350       360
.........|.........|.........|.........|.........|.........|
cctggtggccttgggtgtcctctacgccgaccgcagagggaagcagctgccacgccttgc
P..G..G..L..G..C..P..L..R..R..P..Q..R..E..A..A..T..P..C..
L..V..A..L..G..V..L..Y..A..D..R..R..G..K..Q..L..P..R..L..A..
W..W..P..W..V..S..S..T..P..T..A..E..G..S..S..C..H..A..L..L..

370       380       390       400       410       420
.........|.........|.........|.........|.........|.........|
tagccggctgtgcttcttacaggaggagaggaccttttgtaaaacgaaaaccccgagggat
*..P..A..V..L..L..T..G..G..E..D..L..C..K..T..K..T..P..R..D..
S..R..L..C..F..L..Q..E..E..R..T..F..V..K..R..K..P..R..G..I..
A..G..C..A..S..Y..R..R..R..G..P..L..*..N..E..N..P..E..G..S..

430       440       450       460       470       480
.........|.........|.........|.........|.........|.........|
cccagaggcccaagaggtgagcgaggtctgcaccacccctggctgcgtgatagcagctgc
P..R..G..P..R..G..E..R..G..L..H..H..P..W..L..R..D..S..S..C..
P..E..A..Q..E..V..S..E..V..C..T..T..P..G..C..V..I..A..A..A..
Q..R..P..K..R..*..A..R..S..A..P..P..L..A..A..*..*..Q..L..P..

490       500       510       520       530       540
.........|.........|.........|.........|.........|.........|
caggatcctccagaacatggacccgaccacggaaccgtgtgacgacttctaccagtttgc
Q..D..P..P..E..H..G..P..D..H..G..T..V..*..R..L..L..P..V..C..
R..I..L..Q..N..M..D..P..T..T..E..P..C..D..D..F..Y..Q..F..A..
G..S..S..R..T..W..T..R..P..R..N..R..V..T..T..S..T..S..L..H..

550       560       570       580       590       600
.........|.........|.........|.........|.........|.........|
atgcggaggctggctgcggcgccacgtgatccctgagaccaactcaagatacagcatctt
M..R..R..L..A..A..A..P..R..D..P..*..D..Q..L..K..I..Q..H..L..
C..G..G..W..L..R..R..H..V..I..P..E..T..N..S..R..Y..S..I..F..
A..E..A..G..C..G..A..T..*..S..L..R..P..T..Q..D..T..A..S..L..
```

Figure 1C

```
            610       620       630       640       650       660
        ....|.........|.........|.........|.........|.........|
        tgacgtcctccgcgacgagctggaggtcatcctcaaagcggtgctggagaattcgactgc
        *..R..P..P..R..R..A..G..G..H..P..Q..S..G..A..G..E..F..D..C..
        D..V..L..R..D..E..L..E..V..I..L..K..A..V..L..E..N..S..T..A..
        T..S..S..A..T..S..W..R..S..S..S..K..R..C..W..R..I..R..L..P..

670       680       690       700       710       720
        ....|.........|.........|.........|.........|.........|
        caaggaccggccggctgtggagaaggccaggacgctgtaccgctcctgcatgaaccagag
        Q..G..P..A..G..C..G..E..G..Q..D..A..V..P..L..L..H..E..P..E..
        K..D..R..P..A..V..E..K..A..R..T..L..Y..R..S..C..M..N..Q..S..
        R..T..G..R..L..W..R..R..P..G..R..C..T..A..P..A..*..T..R..V..

730       740       750       760       770       780
        ....|.........|.........|.........|.........|.........|
        tgtgatagagaagcgaggctctcagcccctgctggacatcttggaggtggtgggaggctg
        C..D..R..E..A..R..L..S..A..P..A..G..H..L..G..G..G..G..R..L..
        V..I..E..K..R..G..S..Q..P..L..L..D..I..L..E..V..V..G..G..W..
        *..*..R..S..E..A..L..S..P..C..W..T..S..W..R..W..W..E..A..G..

790       800       810       820       830       840
        ....|.........|.........|.........|.........|.........|
        gccggtggcgatggacaggtggaacgagaccgtaggactcgagtgggagctggagcggca
        A..G..G..D..G..Q..V..E..R..D..R..R..T..R..V..G..A..G..A..A..
        P..V..A..M..D..R..W..N..E..T..V..G..L..E..W..E..L..E..R..Q..
        R..W..R..W..T..G..G..T..R..P..*..D..S..S..G..S..W..S..G..S..

850       860       870       880       890       900
        ....|.........|.........|.........|.........|.........|
        gctggcgctgatgaactcacagttcaacaggcgcgtcctcatcgacctcttcatctggaa
        A..G..A..D..E..L..T..V..Q..Q..A..R..P..H..R..P..L..H..L..E..
        L..A..L..M..N..S..Q..F..N..R..R..V..L..I..D..L..F..I..W..N..
        W..R..*..*..T..H..S..S..T..G..A..S..S..S..T..S..S..S..G..T..
```

Figure 1D

```
          910       920       930       940       950       960
  .........|.........|.........|.........|.........|.........|
  cgacgaccagaactccagccggcacatcatctacatagaccagcccaccttgggcatgcc
  R..R..P..E..L..Q..P..A..H..H..L..H..R..P..A..H..L..G..H..A..
  D..D..Q..N..S..S..R..H..I..I..Y..I..D..Q..P..T..L..G..M..P..
  T..T..R..T..P..A..G..T..S..S..T..*..T..S..P..P..W..A..C..P..

970       980       990      1000      1010      1020
  .........|.........|.........|.........|.........|.........|
  ctcccgagagtactacttcaacggcggcagcaaccggaaggtgcgggaagcctacctgca
  L..P..R..V..L..L..Q..R..R..Q..Q..P..E..G..A..G..S..L..P..A..
  S..R..E..Y..Y..F..N..G..G..S..N..R..K..V..R..E..A..Y..L..Q..
  P..E..S..T..T..S..T..A..A..A..T..G..R..C..G..K..P..T..C..S..

1030      1040      1050      1060      1070      1080
  .........|.........|.........|.........|.........|.........|
  gttcatggtgtcagtggccacgttgctgcgggaggatgcaaacctgcccagggacagctg
  V..H..G..V..S..G..H..V..A..A..G..G..C..K..P..A..Q..G..Q..L..
  F..M..V..S..V..A..T..L..L..R..E..D..A..N..L..P..R..D..S..C..
  S..W..C..Q..W..P..R..C..C..G..R..M..Q..T..C..P..G..T..A..A..

1090      1100      1110      1120      1130      1140
  .........|.........|.........|.........|.........|.........|
  cctggtgcaggaggacatggtgcaggtgctggagctggagacacagctggccaaggccac
  P..G..A..G..G..H..G..A..G..A..G..A..G..D..T..A..G..Q..G..H..
  L..V..Q..E..D..M..V..Q..V..L..E..L..E..T..Q..L..A..K..A..T..
  W..C..R..R..T..W..C..R..C..W..S..W..R..H..S..W..P..R..P..R..

1150      1160      1170      1180      1190      1200
  .........|.........|.........|.........|.........|.........|
  ggtaccccaggaggagagacacgacgtcatcgccttgtaccaccggatgggactggagga
  G..T..P..G..G..E..T..R..R..H..R..L..V..P..P..D..G..T..G..G..
  V..P..Q..E..E..R..H..D..V..I..A..L..Y..H..R..M..G..L..E..E..
  Y..P..R..R..R..D..T..T..S..S..P..C..T..T..G..W..D..W..R..S..
```

Figure 1E

```
          1210      1220      1230      1240      1250      1260
     .........|.........|.........|.........|.........|.........|
     gctgcaaagccagtttggcctgaagggatttaactggactctgttcatacaaactgtgct
     A..A..K..P..V..W..P..E..G..I..*..L..D..S..V..H..T..N..C..A..
     L..Q..S..Q..F..G..L..K..G..F..N..W..T..L..F..I..Q..T..V..L..
     C..K..A..S..L..A..*..R..D..L..T..G..L..C..S..Y..K..L..C..Y..

1270      1280      1290      1300      1310      1320
     .........|.........|.........|.........|.........|.........|
     atcctctgtcaaaatcaagctgctgccagatgaggaagtggtggtctatggcatcccta
     I..L..C..Q..N..Q..A..A..A..R..*..G..S..G..G..L..W..H..P..L..
     S..S..V..K..I..K..L..L..P..D..E..E..V..V..V..Y..G..I..P..Y..
     P..L..S..K..S..S..C..C..Q..M..R..K..W..W..S..M..A..S..P..T..

1330      1340      1350      1360      1370      1380
     .........|.........|.........|.........|.........|.........|
     cctgcagaaccttgaaaacatcatcgacacctactcagccaggaccatacagaactacct
     P..A..E..P..*..K..H..H..R..H..L..L..S..Q..D..H..T..E..L..P..
     L..Q..N..L..E..N..I..I..D..T..Y..S..A..R..T..I..Q..N..Y..L..
     C..R..T..L..K..T..S..S..T..P..T..Q..P..G..P..Y..R..T..T..W..

1390      1400      1410      1420      1430      1440
     .........|.........|.........|.........|.........|.........|
     ggtctggcgcctggtgctggaccgcattggtagcctaagccagagattcaaggacacacg
     G..L..A..P..G..A..G..P..H..W..*..P..K..P..E..I..Q..G..H..T..
     V..W..R..L..V..L..D..R..I..G..S..L..S..Q..R..F..K..D..T..R..
     S..G..A..W..C..W..T..A..L..V..A..*..A..R..D..S..R..T..H..E..

1450      1460      1470      1480      1490      1500
     .........|.........|.........|.........|.........|.........|
     agtgaactaccgcaaggcgctgtttggcacaatggtggaggaggtgcgctggcgtgaatg
     S..E..L..P..Q..G..A..V..W..H..N..G..G..G..G..A..L..A..*..M..
     V..N..Y..R..K..A..L..F..G..T..M..V..E..E..V..R..W..R..E..C..
     *..T..T..A..R..R..C..L..A..Q..W..W..R..R..C..A..G..V..N..V..
```

Figure 1F

```
             1510       1520       1530       1540       1550       1560
        .........|.........|.........|.........|.........|.........|
        tgtgggctacgtcaacagcaacatggagaacgccgtgggctccctctacgtcagggaggc
        C..G..L..R..Q..Q..Q..H..G..E..R..R..G..L..P..L..R..Q..G..G..
        V..G..Y..V..N..S..N..M..E..N..A..V..G..S..L..Y..V..R..E..A..
        W..A..T..S..T..A..T..W..R..T..P..W..A..P..S..T..S..G..R..R..

1570       1580       1590       1600       1610       1620
        .........|.........|.........|.........|.........|.........|
        gttccctggagacagcaagagcatggtcagagaactcattgacaaggtgcggacagtgtt
        V..P..W..R..Q..Q..E..H..G..Q..R..T..H..*..Q..G..A..D..S..V..
        F..P..G..D..S..K..S..M..V..R..E..L..I..D..K..V..R..T..V..F..
        S..L..E..T..A..R..A..W..S..E..N..S..L..T..R..C..G..Q..C..L..

1630       1640       1650       1660       1670       1680
        .........|.........|.........|.........|.........|.........|
        tgtggagacgctggacgagctgggctggatggacgaggagtccaagaagaaggcgcagga
        C..G..D..A..G..R..A..G..L..D..G..R..G..V..Q..E..E..G..A..G..
        V..E..T..L..D..E..L..G..W..M..D..E..E..S..K..K..K..A..Q..E..
        W..R..R..W..T..S..W..A..G..W..T..R..S..P..R..R..R..R..R..R..

1690       1700       1710       1720       1730       1740
        .........|.........|.........|.........|.........|.........|
        gaaggccatgagcatccgggagcagatcgggcaccctgactacatcctggaggagatgaa
        E..G..H..E..H..P..G..A..D..R..A..P..*..L..H..P..G..G..D..E..
        K..A..M..S..I..R..E..Q..I..G..H..P..D..Y..I..L..E..E..M..N..
        R..P..*..A..S..G..S..R..S..G..T..L..T..T..S..W..R..R..*..T..

1750       1760       1770       1780       1790       1800
        .........|.........|.........|.........|.........|.........|
        caggcgcctggacgaggagtactccaatctgaacttctcagaggacctgtactttgagaa
        Q..A..P..G..R..G..V..L..Q..S..E..L..L..R..G..P..V..L..*..E..
        R..R..L..D..E..E..Y..S..N..L..N..F..S..E..D..L..Y..F..E..N..
        G..A..W..T..R..S..T..P..I..*..T..S..Q..R..T..C..T..L..R..T..
```

Figure 16

```
             1810       1820       1830       1840       1850       1860
         ........|.........|.........|.........|.........|.........|
         cagtctgcagaacctcaaggtgggcgcccagcggagcctcaggaagcttcgggaaaaggt
         Q..S..A..E..P..Q..G..G..R..P..A..E..P..Q..E..A..S..G..K..G..
         S..L..Q..N..L..K..V..G..A..Q..R..S..L..R..K..L..R..E..K..V..
         V..C..R..T..S..R..W..A..P..S..G..A..S..G..S..F..G..K..R..W..

1870       1880       1890       1900       1910       1920
         ........|.........|.........|.........|.........|.........|
         ggacccaaatctctggatcatcggggcggcggtggtcaatgcgttctactccccaaaccg
         G..P..K..S..L..D..H..R..G..G..G..G..Q..C..V..L..L..P..K..P..
         D..P..N..L..W..I..I..G..A..A..V..V..N..A..F..Y..S..P..N..R..
         T..Q..I..S..G..S..S..G..R..R..W..S..M..R..S..T..P..Q..T..E..

1930       1940       1950       1960       1970       1980
         ........|.........|.........|.........|.........|.........|
         aaaccagattgtattccctgccgggatcctccagcccccttcttcagcaaggagcagcc
         K..P..D..C..I..P..C..R..D..P..P..A..P..L..L..Q..Q..G..A..A..
         N..Q..I..V..F..P..A..G..I..L..Q..P..P..F..F..S..K..E..Q..P..
         T..R..L..Y..S..L..P..G..S..S..S..P..P..S..S..A..R..S..S..H..

1990       2000       2010       2020       2030       2040
         ........|.........|.........|.........|.........|.........|
         acaggccttgaactttggaggcattgggatggtgatcgggcacgagatcacgcacggctt
         T..G..L..E..L..W..R..H..W..D..G..D..R..A..R..D..H..A..R..L..
         Q..A..L..N..F..G..G..I..G..M..V..I..G..H..E..I..T..H..G..F..
         R..P..*..T..L..E..A..L..G..W..*..S..G..T..R..S..R..T..A..L..

2050       2060       2070       2080       2090       2100
         ........|.........|.........|.........|.........|.........|
         tgacgacaatggccggaacttcgacaagaatggcaacatgatggattggtggagtaactt
         *..R..Q..W..P..E..L..R..Q..E..W..Q..H..D..G..L..V..E..*..L..
         D..D..N..G..R..N..F..D..K..N..G..N..M..M..D..W..W..S..N..F..
         T..T..M..A..G..T..S..T..R..M..A..T..*..W..I..G..G..V..T..S..
```

Figure 1H

```
              2110      2120      2130      2140      2150      2160
        .........|.........|.........|.........|.........|.........|
        ctccacccagcacttccgggagcagtcagagtgcatgatctaccagtacggcaactactc
        L..H..P..A..L..P..G..A..V..R..V..H..D..L..P..V..R..Q..L..L..
        S..T..Q..H..F..R..E..Q..S..E..C..M..I..Y..Q..Y..G..N..Y..S..
        P..P..S..T..S..G..S..S..Q..S..A..*..S..T..S..T..A..T..T..P..

2170      2180      2190      2200      2210      2220
        .........|.........|.........|.........|.........|.........|
        ctgggacctggcagacgaacagaacgtgaacggattcaacacccttggggaaaacattgc
        L..G..P..G..R..R..T..E..R..E..R..I..Q..H..P..W..G..K..H..C..
        W..D..L..A..D..E..Q..N..V..N..G..F..N..T..L..G..E..N..I..A..
        G..T..W..Q..T..N..R..T..*..T..D..S..T..P..L..G..K..T..L..L..

2230      2240      2250      2260      2270      2280
        .........|.........|.........|.........|.........|.........|
        tgacaacggagggttgcggcaagcctataaggcctacctcaagtggatggcagagggtgg
        *..Q..R..R..G..A..A..S..L..*..G..L..P..Q..V..D..G..R..G..W..
        D..N..G..G..V..R..Q..A..Y..K..A..Y..L..K..W..M..A..E..G..G..
        T..T..E..G..C..G..K..P..I..R..P..T..S..S..G..W..Q..R..V..A..

2290      2300      2310      2320      2330      2340
        .........|.........|.........|.........|.........|.........|
        caaggaccagcagctgcccggcctggatctcacccatgagcagctcttcttcatcaacta
        Q..G..P..A..A..A..R..P..G..S..H..P..*..A..A..L..L..H..Q..L..
        K..D..Q..Q..L..P..G..L..D..L..T..H..E..Q..L..F..F..I..N..Y..
        R..T..S..S..C..P..A..W..I..S..P..M..S..S..S..S..S..S..T..M..

2350      2360      2370      2380      2390      2400
        .........|.........|.........|.........|.........|.........|
        tgcccaggtgtggtgcgggtcctaccggcccgagttcgccatccaatccatcaagacaga
        C..P..G..V..V..R..V..L..P..A..R..V..R..H..P..I..H..Q..D..R..
        A..Q..V..W..C..G..S..Y..R..P..E..F..A..I..Q..S..I..K..T..D..
        P..R..C..G..A..G..P..T..G..P..S..S..P..S..N..P..S..R..Q..T..
```

Figure 1I

```
           2410      2420      2430      2440      2450      2460
        .........|.........|.........|.........|.........|.........|
        cgtccacagtcccctgaagtacagggtactggggtcgctgcagaacctggccgccttcgc
        R..P..Q..S..P..E..V..Q..G..T..G..V..A..A..E..P..G..R..L..R..
        V..H..S..P..L..K..Y..R..V..L..G..S..L..Q..N..L..A..A..F..A..
        S..T..V..P..*..S..T..G..Y..W..G..R..C..R..T..W..P..P..S..Q..

2470      2480      2490      2500      2510      2520
        .........|.........|.........|.........|.........|.........|
        agacacgttccactgtgcccggggcaccccatgcaccccaaggagcgatgccgcgtgtg
        R..H..V..P..L..C..P..G..H..P..H..A..P..Q..G..A..M..P..R..V..
        D..T..F..H..C..A..R..G..T..P..M..H..P..K..E..R..C..R..V..W..
        T..R..S..T..V..P..G..A..P..P..C..T..P..R..S..D..A..A..C..G..

2530      2540      2550      2560      2570      2580
        .........|.........|.........|.........|.........|.........|
        gtagccaaggccctgccgcgctgtgcggcccacgcccacctgctgctcggaggcatctgt
        V..A..K..A..L..P..R..C..A..A..H..A..H..L..L..L..G..G..I..C..
        *..P..R..P..C..R..A..V..R..P..T..P..T..C..C..S..E..A..S..V..
        S..Q..G..P..A..A..L..C..G..P..R..P..P..A..A..R..R..H..L..C..

2590      2600      2610      2620      2630      2640
        .........|.........|.........|.........|.........|.........|
        gcgaaggtgcagctagcggcgacccagtgtacgtcccgccccggccaaccatgccaagcc
        A..K..V..Q..L..A..A..T..Q..C..T..S..R..P..G..Q..P..C..Q..A..
        R..R..C..S..*..R..R..P..S..V..R..P..A..P..A..N..H..A..K..P..
        E..G..A..A..S..G..D..P..V..Y..V..P..P..R..P..T..M..P..S..L..

2650      2660      2670      2680      2690      2700
        .........|.........|.........|.........|.........|.........|
        tgcctgccaggcctctgcgcctggcctagggtgcagccacctgcctgacacccagggatg
        C..L..P..G..L..C..A..W..P..R..V..Q..P..P..A..*..H..P..G..M..
        A..C..Q..A..S..A..P..G..L..G..C..S..H..L..P..D..T..Q..G..*..
        P..A..R..P..L..R..L..A..*..G..A..A..T..C..L..T..P..R..D..E..
```

Figure 1J

```
          2710      2720      2730      2740      2750      2760
    .........|.........|.........|.........|.........|.........|
    agcagtgtccagtgcagtacctggaccggagcccctccacagacacccgcggggctcag
    S..S..V..Q..C..S..T..W..T..G..A..P..S..T..D..T..R..G..A..Q..
    A..V..S..S..A..V..P..G..P..E..P..P..P..Q..T..P..A..G..L..S..
    Q..C..P..V..Q..Y..L..D..R..S..P..L..H..R..H..P..R..G..S..V..

2770      2780      2790      2800      2810      2820
    .........|.........|.........|.........|.........|.........|
    tgcccccgtcacagctctgtagagacaatcaactgtgtcctgcccacccctccaaggtgca
    C..P..R..H..S..S..V..E..T..I..N..C..V..L..P..T..L..Q..G..A..
    A..P..V..T..A..L..*..R..Q..S..T..V..S..C..P..P..S..K..V..H..
    P..P..S..Q..L..C..R..D..N..Q..L..C..P..A..H..P..P..R..C..I..

2830      2840      2850      2860      2870      2880
    .........|.........|.........|.........|.........|.........|
    ttgtcttccagtatctacagcttcagacttgagctaagtaaatgcttcaaagaaaaaaaa
    L..S..S..S..I..Y..S..F..R..L..E..L..S..K..C..F..K..E..K..K..
    C..L..P..V..S..T..A..S..D..L..S..*..V..N..A..S..K..K..K..K..
    V..F..Q..Y..L..Q..L..Q..T..*..A..K..*..M..L..Q..R..K..K..K..

2890      2900      2910      2920      2930      2940
    .........|.........|.........|.........|.........|.........|
    aaaaaaaaaaaaa
    K..K..K..K..
     K..K..K..K..
      K..K..K..
```

Figure 2

Comparison of human SEP to most closely related human proteins by pairwise alignment
from the blastp algorithm

| Swiss-Prot Protein name | Whole protein | Catalytic domain |
|---|---|---|
| SEP_HUMAN | 100% (779/779) | 100% (209/209) |
| NEP_HUMAN | 54% (382/696) | 66% (139/209) |
| ECE1_HUMAN | 39% (281/707) | 54% (113/209) |
| ECE2_HUMAN | 39% (298/757) | 52% (109/209) |
| PEX_HUMAN | 39% (284/723) | 50% (108/214) |
| XCE_HUMAN | 36% (257/710) | 48% (101/209) |
| KELL_HUMAN | 27% (189/700) | 36% (77/209) |

Figure 3

Comparison of human, rat and mouse sequences for SEP by pairwise alignment from blastp (protein) and fasta (coding nucleotide) algorithms

| Species | Protein (%identity) | Coding nucleotide (%identity) |
|---|---|---|
| Human | 100% (779/779) | 100% (2337 overlap) |
| Mouse | 77% (690/770) | 82% (2082 overlap) |
| Rat | 77% (607/780) | 82% (2109 overlap) |

Figure 4A

Multiple alignment of human SEP and related human proteins showing catalytic domain

```
                    *        20         *        40         *        60
SEP_HUMAN    : MG---------------K--SEGPVGMVESAGRAGQK-------------------- :  20
NEP_HUMAN    : MG---------------K--SESQMDITDINTPKPKKK-----------------Q :  22
ECE1_HUMAN   : MRGVWPPPVSALLSALGMSTYKRATLDEEDLVDSLSEGDAYPNGLQVNFHSPRSGQRCWA :  60
ECE2_HUMAN   : MN----VALQELGAGSNMVEYKRATLRDEDAPETPVEGGASPDAMEVGFQ--KGTRQLLG :  54
PEX_HUMAN    : ---------------------MEAETGSSVETGKKANR------------------G :  18
XCE_HUMAN    : MEP----PYSLTAHYDEFQEVKYVSRCGAGGARGASLPPGFPLGAARSATGARSG---LP :  53
KELL_HUMAN   : MEG---------GDQSEEEPRERSQAGGMGTLWSQESTPEERLPVEGS----------R :  40

*        80         *       100         *       120
SEP_HUMAN    : RPGFLEGGLLLLLLLVTAALVALGVLYADRRGKQLPRLASRLCFLQEERTFVKRKPRGIP :  80
NEP_HUMAN    : RWTPLEISLSVLVLLLTIIAVTMIALYAT------------------YDDG-------- :  55
ECE1_HUMAN   : ARTQVEKRLVVLVVLLAAGLVACLAALGIQYQT---------------RSP--------- :  96
ECE2_HUMAN   : SRTQLELVLAGASLLLAALLLGCLVALGVQYH---------------RDPS----H--- :  91
PEX_HUMAN    : TRIALVVFVGGTLVLGTILFLVSQGLLSLQAK---------------QEY--------- :  53
XCE_HUMAN    : RWNRREVCLLSGLVFAAGLCAILAAMLALKYLG-------------PVAAGG-----G-- :  93
KELL_HUMAN   : PWAVARRVLTAILILGLLLCFSVLLFYNFQNCG---------------PRP--------- :  76

*       140         *       160         *       180
SEP_HUMAN    : EAQEVSEVCTTPGCVIAAARILQN-MDPTTEPCDDFYQFACGGWLRRHVIPETNSRYSIF : 139
NEP_HUMAN    : -------ICKSSDCIKSAARLIQN-MDATTEPCTDFFKYACGGWLKRNVIPETSSRYGNF : 107
ECE1_HUMAN   : ------SVCLSEACVSVTSSILSS-MDPTVDPCHDFFSYACGGWIKANPVPDGHSRWGTF : 149
ECE2_HUMAN   : ------STCLTEACIRVAGKILES-LDRGVSPCEDFYQFSCGGWIRRNPLPDGRSRWNTF : 144
PEX_HUMAN    : --------CLKPECIEAAAAILSK-VNLSVDPCDNFFRFACDGWISNNPIPEDMPSYGVY : 104
XCE_HUMAN    : ---ACPEGCPERKAFARAARFLAANLDASIDPCQDFYSFACGGWLRRHAIPDDKLTYGTI : 150
KELL_HUMAN   : --------CETSVCLDLRDHYLAS-GNTSVAPCTDFFSFACG---------RAKETNNSF : 118

*       200         *       220         *       240
SEP_HUMAN    : DVLRDELEVILKAVLENSTA--KDRPAVEKARTLYRSCMNQSVIEKRGSQPLLDILEV-V : 196
NEP_HUMAN    : DILRDELEVVLKDVLQEPKT--EDIVAVQKAKALYRSCINESAIDSRGGEPLLKLLPD-I : 164
ECE1_HUMAN   : SNLWEHNQAIIKHLLENSTA--SVSEAERKAQVYYRACMNETRIEELRAKPLMELIER-L : 206
ECE2_HUMAN   : NSLWDQNQAILKHLLENTTFN-SSSEAEQKTQRFYLSCLQVERIEELGAQPLRDLIEK-I : 202
PEX_HUMAN    : PWLRHNVDLKLKELLEKSISRRRDTEAIQKAKILYSSCMNEKAIEKADAKPLLHILRHSP : 164
XCE_HUMAN    : AAIGEQNEERLRRLLARPGGG-PGGAAQRKVRAFFRSCLDMREIERLGPRPMLEVIED-C : 208
KELL_HUMAN   : QELATKNKNRLRRILEVQNS-WHPGSGEEKAFQFYNSCMDTLAIEAAGTGPLRQVIEE-L : 176

*       260         *       280         *       300
SEP_HUMAN    : GGWPVAMDR------WNETVGLEWELERQLALMNSQFNRRVLIDLFIWNDDQNSSRHIIY : 250
NEP_HUMAN    : YGWPVATEN------WEQKYGASWTAEKAIAQLNSKYGKKVLINLFVGTDDKNSVNHVIH : 218
ECE1_HUMAN   : GGWNITGP-------WAKDN-----FQDTLQVVTAHYRTSPFFSVYVSADSKNSNSNVIQ : 254
ECE2_HUMAN   : GGWNITGP-------WDQDN-----FMEVLKAVAGTYRATPFFTVYISADSKSSNSNVIQ : 250
PEX_HUMAN    : FRWPVLESNIGPEGVWSERK---FSLLQTLATFRGQYSNSVFIRLYVSPDDKASNEHILK : 221
XCE_HUMAN    : GGWDLGGAE------ERPGVAARWDLNRLLYKAQGVYSAAALFSLTVSLDDRNSSRYVIR : 262
KELL_HUMAN   : GGWRISGK-------WTSLN-----FNRTLRLLMSQYGHFPFFRAYLGPHPASPHTPVIQ : 224

*       320         *       340         *       360
SEP_HUMAN    : IDQPTLGMPSR-EYYFNGGSNRKVREAYLQFMVSVATLLREDANLPRDSCLVQEDMVQVL : 309
NEP_HUMAN    : IDQPRLGLPSR-DYYECTGIYKEACTAYVDFMISVARLIRQEERLPIDENQLALEMNKVM : 277
ECE1_HUMAN   : VDQSGLGLPSR-DYYLNKTENEKVLTGYLNYMVQLGKLLGGGDE-----EAIRPQMQQIL : 308
ECE2_HUMAN   : VDQSGLFLPSR-DYYLNRTANEKVLTAYLDYMEELGMLLGGRP------TSTREQMQQVL : 303
PEX_HUMAN    : LDQATLSLAVREDYLDNSTEAKSYRDALYKFMVDTAVLLGANS------SRAEHDMKSVL : 275
XCE_HUMAN    : IDQDGLTLPERTLYLAQDEDSEKVLAAYRVFMERVLSLLGADA-------VEQKAQEIL : 314
KELL_HUMAN   : IDQPEFDVPLK--QDQEQKIYAQIFREYLTYLNQLGTLLGGDP------SKVQEHSSLSI : 276

*       380         *       400         *       420
SEP_HUMAN    : ELETQLAKATVPQ--EERHDVIALYHRMGLEELQSQFGLKG----FNWTLFIQTVLSSVK : 363
NEP_HUMAN    : ELEKEIANATAKP--EDRNDPMLLYNKMTLAQIQNNFSLEINGKPFSWLNFTNEIMSTVN : 335
ECE1_HUMAN   : DFETALANITIPQ--EKRRDEELIYHKVTAAELQ---TLAP---AINWLPFLNTIFYPVE : 360
ECE2_HUMAN   : ELEIQLANITVPQ--DQRRDEEKIYHKMSISELQ---ALAP---SMDWLEFLSFLLSPLE : 355
PEX_HUMAN    : RLEIKIAEIMIPH--ENRTS-EAMYNKMNISELS---AMIP---QFDWLGYIKKVIDTRL : 326
XCE_HUMAN    : QVEQQLANITVSEYDDLRRDVSSMYNKVTLGQLQ---KITP---HLRWKWLLDQIFQEDF : 368
KELL_HUMAN   : SITSRLFQFLRPL--EQRRAQGKLFQMVTIDQLK---EMAP---AIDWLSCLQATFTPMS : 328
```

Figure 7B

```
                       *       440         *       460         *       480
SEP_HUMAN    : IKLL----PDEEVVVYGIPYLQNLENIIDTYSAR---TIQNYLVWRLVLDRIGSLSQRFK : 416
NEP_HUMAN    : ISIT----NEEDVVVYAPEYLTKLKPILTKYSAR---DLQNLMSWRFIMDLVSSLSRTYK : 388
ECE1_HUMAN   : IN------ESEPIVVYDKEYLEQISTLNTTDRC---LLNNYMIWNLVRKTSSFLDQRFQ : 411
ECE2_HUMAN   : LS------DSEPVVVYGMDYLQQVSELINRTEPS---ILNNYLIWNLVQKTTSSLDRRFE : 406
PEX_HUMAN    : YPHLKDISPSENVVVRVPQYFKDLFRILGSERKK---TIANYLVWRMVYSRIPNLSRRFQ : 383
XCE_HUMAN    : SE------EEEVVLLATDYMQQVSQLIRSTPHR---VLHNYLVWRVVVVLSEHLSPPFR : 418
KELL_HUMAN   : LS------PSQSLVVHDVEYLKNMSQLVEEMLLKQRDFLQSHMILGLVVTLSPALDSQFQ : 382

*       500         *       520         *       540
SEP_HUMAN    : DTRVNYRKALFGTMVEEV-----RWRECVGYVNSNMENAVGSLYVREAFPGDSKSMVREL : 471
NEP_HUMAN    : ESRNAFRKALYGTTSETA-----TWRRCANYVNGNMENAVGRLYVEAAFAGESKHVVEDL : 443
ECE1_HUMAN   : DADEKFMEVMYGTKKTCLP----RWKFCVSDTENNLGFALGPMFVKATFAEDSKSIATEI : 467
ECE2_HUMAN   : SAQEKLLETLYGTKKSCVP----RWQTCISNTDDALGFALGSLFVKATFDRQSKEIAEGM : 462
PEX_HUMAN    : YRWLEFSRVIQGTTTLLP-----QWDKCVNFIESALPYVVGKMFVDVYFQEDKKEMMEEL : 438
XCE_HUMAN    : EALHELAQEMEGSDKPQE-----LARVCLGQANRHFGMALGALFVHEHFSAASKAKVQQL : 473
KELL_HUMAN   : EARRKLSQKLRELTEQPPMPARPRWMKCVEETGTFFEPTLAALFVREAFGPSTRSAAMKL : 442

*       560         *       580         *       600
SEP_HUMAN    : IDKVRTVFVETLD-ELGWMDEESKKKAQEKAMSIREQIGHPDYILEEMNRRLDEEYSNLN : 530
NEP_HUMAN    : IAQIREVFIQTLD-DLTWMDAETKKRAEEKALAIKERIGYPDDIVSNDNK-LNNEYLELN : 501
ECE1_HUMAN   : ILEIKKAFEESLS-TLKWMDEETRKSAKEKADAIYNMIGYPNFIMDP--KELDKVFNDYT : 524
ECE2_HUMAN   : ISEIRTAFEEALG-QLVWMDEKTRQAAKEKADAIYDMIGFPDFILEP--KELDDVYDGYE : 519
PEX_HUMAN    : VEGVRWAFIDMLEKENEWMDAGTKRKAKEKARAVLAKVGYPEFIMND--THVNEDLKAIK : 496
XCE_HUMAN    : VEDIKYILGQRLE-ELDWMDAETRAAARAKLQYMMVMVGYPDFLLKP--DAVDKEY-EFE : 529
KELL_HUMAN   : FTAIRDALITRLR-NLPWMNEETQNMAQDKVAQLQVEMGASEWALKP--ELARQEYNDIQ : 499

*       620         *       640         *       660
SEP_HUMAN    : FSEDLYFENSLQNLKVGAQRSLRKLREKVDPNLWIIGAAVVNAFYSPNRNQIVFPAGILQ : 590
NEP_HUMAN    : YKEDEYFENIIQNLKFSQSKQLKKLREKVDKDEWISGAAVVNAFYSSGRNQIVFPAGILQ : 561
ECE1_HUMAN   : AVPDLYFENAMRFFNFSWRVTADQLRKAPNRDQWSMTPPMVNAYYSPTKNEIVFPAGILQ : 584
ECE2_HUMAN   : ISEDSFFQNMLNLYNFSAKVMADQLRKPPSRDQWSMTPQTVNAYYLPTKNEIVFPAGILQ : 579
PEX_HUMAN    : FSEADYFGNVLQTRKYLAQSDFFWLRKAVPKTEWFTNPTTVNAFYSASTNQIRFPAGELQ : 556
XCE_HUMAN    : VHEKTYFKNILNSIRFSIQLSVKKIRQEVDKSTWLLPPQALNAYYLPNKNQMVFPAGILQ : 589
KELL_HUMAN   : LGSS-FLQSVLSCVRSLRARIVQSFLQPHPQHRWKVSPWDVNAYYSVSDHVVVFPAGLLQ : 558

==catalytic domain==
                       *       680         *       700         *       720
SEP_HUMAN    : PPFFS-KEQPQALNFGGIGMVIGHEITHGFDDNGRNFDKNGNMMDWWSNFSTQHFREQSE : 649
NEP_HUMAN    : PPFFS-AQQSNSLNYGGIGMVIGHEITHGFDDNGRNFNKDGDLVDWWTQQSASNFKEQSQ : 620
ECE1_HUMAN   : APFYT-RSSPKALNFGGIGVVVGHELTHAFDDQGREYDKDGNLRPWWKNSSVEAFKRQTE : 643
ECE2_HUMAN   : APFYA-RNHPKALNFGGIGVVMGHELTHAFDDQGREYDKEGNLRPWWQNESLAAFRNHTA : 638
PEX_HUMAN    : KPFFWGTEYPRSLSYGAIGVIVGHEFTHGFDNNGRKYDKNGNLDPWWSTESEEKFKEKTK : 616
XCE_HUMAN    : PTLYD-PDFPQSLNYGGIGTIIGHELTHGYDDWGGQYDRSGNLLHWWTEASYSRFLRKAE : 648
KELL_HUMAN   : PPFFH-PGYPRAVNFGAAGSIMAHELLHIFY---QLLLPGG-----CLACDNHALQEAHL : 609

=====================catalytic domain=====================
                       *       740         *       760         *       780
SEP_HUMAN    : CMIYQYGNYSWDLADEQNVNGFNTLGENIADNGGVRQAYKAYLKWMA--EGG-KDQQLPG : 706
NEP_HUMAN    : CMVYQYGNFSWDLAGGQHLNGINTLGENIADNGGLGQAYRAYQNYIK--KNG-EEKLLPG : 677
ECE1_HUMAN   : CMVEQYSNYS---VNGEPVNGRHTLGENIADNGGLKAAYRAYQNWVK--KNG-AEHSLPT : 697
ECE2_HUMAN   : CMEEQYNQYQ---VNGERLNGRQTLGENIADNGGLKAAYNAYKAWLR--KHG-EEQQLPA : 692
PEX_HUMAN    : CMINQYSNYYWK-KAGLNVKGKRTLGENIADNGGLREAFRAYRKWINDRRQGLEEPLLPG : 675
XCE_HUMAN    : CIVRLYDNFT---VYNQRVNGKHTLGENIADMGGLKLAYHAYQKWVR--EHG-PEHPLPR : 702
KELL_HUMAN   : CLKRHYAAFP--LPSRTSFNDSLTFLENAADVGGLAIALQAYSKRLLR-HHG--ETVLPS : 664

====================catalytic domain===================
                       *       800         *       820         *       840
SEP_HUMAN    : LDLTHEQLFFINYAQVWCGSYRPEFAIQSIKTDVHSPLKYRVLGSLQNLAAFADTFHCAR : 766
NEP_HUMAN    : LDLNHKQLFFLNFAQVWCGTYRPEYAVNSIKTDVHSPGNFRIIGTLQNSAEFSEAFHCRK : 737
ECE1_HUMAN   : LGLTNNQLFFLGFAQVWCSVRTPESSHEGLITDPHSPSRFRVIGSLSNSKEFSEHFRCPP : 757
ECE2_HUMAN   : VGLTNHQLFFVGFAQVWCSVRTPESSHEGLVTDPHSPARFRVLGTLSNSRDFLRHFGCPV : 752
PEX_HUMAN    : ITFTNNQLFFLSYAHVRCNSYRPEAAREQVQIGAHSPPQFRVNGAISNFEEFQKAFNCPP : 735
XCE_HUMAN    : LKYTHDQLFFIAFAQNWCIKRRSQSIYLQVLTDKHAPEHYRVLGSVSQFEEFGRVLHCPK : 762
KELL_HUMAN   : LDLSPQQIFFRSYAQVMCRKPSPQ-D----SHDTHSPPHLRVHGPLSSTPAFARYFRCAR : 719

=====================catalytic domain=====================
```

Figure 4C

```
                           *
SEP_HUMAN   : GTPMHPKER-CRVW  : 779
NEP_HUMAN   : NSYMNPEKK-CRVW  : 750
ECE1_HUMAN  : GSPMNPPHK-CEVW  : 770
ECE2_HUMAN  : GSPMNPGQL-CEVW  : 765
PEX_HUMAN   : NSTMNRGMDSCRLW  : 749
XCE_HUMAN   : VSPMNPAHK-CSVW  : 775
KELL_HUMAN  : GALLNPSSR-CQLW  : 732

==catalytic===
```

Figure 5A

Multiple alignment of human, rat and mouse SEP proteins showing catalytic domain

```
                  *        20         *        40         *        60
SEP_HUMAN  : MGKSEGPVGMVESAGRAGQKRPGFLEGGLLLLL-LLVTAALVALGVLYADRRGKQLPRLA :  59
SEP_RAT    : MGKSESSVGMMERADNCGRRRLGFVECGLLVLLTLLLMGAIVTLGVFYS--IGKQLPLLN :  58
SEP_MOUSE  : --------MVERAGWCRKKSPGFVEYGLMVLL-LLLLGAIVTLGVFYS--IGKQLPLLT :  48

*        80         *       100         *       120
SEP_HUMAN  : SRLCFLQEERTFVKRKPRGIPEAQEVSEVCTTPGCVIAAARILQNMDPTTEPCDDFYQFA : 119
SEP_RAT    : SLLHVSRHERTVVKRVLR---DSSQKSDICTTPSCVIAAARILQNMDQSKKPCDNFYQYA : 115
SEP_MOUSE  : SLLHFSWDERTVVKRALR---DSSLKSDICTTPSCVIAAARILENMDQSRNPCENFYQYA : 105

*       140         *       160         *       180
SEP_HUMAN  : CGGWLRRHVIPETNSRYSIFDVLRDELEVILKAVLENSTAKDRPAVEKARTLYRSCMNQS : 179
SEP_RAT    : CGGWLRHHVIPETNSRYSVFDILRDELEVILKGVLEDSSVQHRPAVEKAKTLYRSCMNQS : 175
SEP_MOUSE  : CGGWLRHHVIPETNSRYSVFDILRDELEVILKGVLEDSTSQHRPAVEKAKTLYRSCMNQS : 165

*       200         *       220         *       240
SEP_HUMAN  : VIEKRGSQPLLDILEVVGGWPVAMDRWNETVGLEWELERQLALMNSQFNRRVLIDLFIWN : 239
SEP_RAT    : VIEKRDSEPLLNVLDMIGGWPVAMDKWNETMGPKWELERQLAVLNSQFNRRVLIDLFIWN : 235
SEP_MOUSE  : VIEKRDSEPLLSVLKMVGGWPVALDKWNETMGLKWELERQLAVLNSQFNRRVLIDLFIWN : 225

*       260         *       280         *       300
SEP_HUMAN  : DDQNSSRHIIYIDQPTLGMPSREYYFNGGSNRKVREAYLQFMVSVATLLREDANLPRDSC : 299
SEP_RAT    : DDQNSSRHVIYIDQPTLGMPSREYYFKEDS-HRVREAYLQFMTSVATMLRRDLNLPGETD : 294
SEP_MOUSE  : DDQNSSRHVIYIDQPTLGMPSREYYFQEDNNHKVRKAYPEFMTSVATMLRKDQNLSKESA : 285

*       320         *       340         *       360
SEP_HUMAN  : LVQEDMVQVLELETQLAKATVPQEERHDVIALYHRMGLEELQSQFGLKGFNWTLFIQTVL : 359
SEP_RAT    : LVQEEMAQVLHLETHLANATVPQEKRHDVTALYHRMGLEELQERFGLKGFNWTLFIQNVL : 354
SEP_MOUSE  : MVREEMAEVLELETHLANATVPQEKRHDVTALYHRMDLMELQERFGLKGFNWTLFIQNVL : 345

*       380         *       400         *       420
SEP_HUMAN  : SSVKIKLLPDEEVVVYGIPYLQNLENIIDTYSARTIQNYLVWRLVLDRIGSLSQRFKDTR : 419
SEP_RAT    : SSVQVELLPNEEVVVYGIPYLENLEEIIDVFPAQTLQNYLVWRLVLDRIGSLSQRFKEAR : 414
SEP_MOUSE  : SSVEVELFPDEEVVVYGIPYLENLEDIIDSYSARTMQNYLVWRLVLDRIGSLSQRFKEAR : 405

*       440         *       460         *       480
SEP_HUMAN  : VNYRKALFGTMVEEVRWRECVGYVNSNMENAVGSLYVREAFPGDSKSMVRELIDKVRTVF : 479
SEP_RAT    : VDYRKALYGTTMEEVRWRECVSYVNSNMESAVGSLYIKRAFSKDSKSIVSELIEKIRSVF : 474
SEP_MOUSE  : VDYRKALYGTTVEEVRWRECVSYVNSNMESAVGSLYIKRAFSKDSKSTVRELIEKIRSVF : 465

*       500         *       520         *       540
SEP_HUMAN  : VETLDELGWMDEESKKKAQEKAMSIREQIGHPDYILEEMNRRLDEEYSNLNFSEDLYFEN : 539
SEP_RAT    : VDNLDELNWMDEESKKKAQEKALNIREQIGYPDYILEDNNRHLDEEYSSLTFSEDLYFEN : 534
SEP_MOUSE  : VDNLDELNWMDEESKKKAQEKAMNIREQIGYPDYILEDNNKHLDEEYSSLTFYEDLYFEN : 525

*       560         *       580         *       600
SEP_HUMAN  : SLQNLKVGAQRSLRKLREKVDPNLWIIGAAVVNAFYSPNRNQIVFPAGILQPPFFSKEQP : 599
SEP_RAT    : GLQNLKNNAQRSLKKLREKVDQNLWIIGAAVVNAFYSPNRNLIVFPAGILQPPFFSKDQP : 594
SEP_MOUSE  : GLQNLKNNAQRSLKKLREKVDQNLWIIGAAVVNAFYSPNRNQIVFPAGILQPPFFSKDQP : 585

======catalytic domain======
                  *       620         *       640         *       660
SEP_HUMAN  : QALNFGGIGMVIGHEITHGFDDNGRNFDKNGNMMDWWSNFSTQHFREQSECMIYQYGNYS : 659
SEP_RAT    : QALNFGGIGMVIGHEITHGFDDNGRNFDKNGNMLDWWSNFSARHFRQQSQCMIYQYGSNFS : 654
SEP_MOUSE  : QSLNFGGIGMVIGHEITHGFDDNGRNFDKNGNMLDWWSNFSARHFQQQSQCMIYQYGNFS : 645

========================catalytic domain========================
```

Figure 5B

```
              *        680         *         700         *         720
SEP_HUMAN  : WDLADEQNVNGFNTLGENIADNGGVRQAYKAYLKWMAEGGKDQQLPGLDLTHEQLFFINY : 719
SEP_RAT    : WELADNQNVNGFSTLGENIADNGGVRQAYKAYLQWLAEGGRDQRLPGLNLTYAQLFFINY : 714
SEP_MOUSE  : WELADNQNVNGFSSLGENIADNGGVRQAYKAYLRWLADGGKDQRLPGLNLTYAQLFFINY : 705

=====================catalytic domain======================
              *        740         *         760         *         780
SEP_HUMAN  : AQVWCGSYRPEFAIQSIKTDVHSPLKYRVLGSLQNLAAFADTFHCARGTPMHPKERCRVW : 779
SEP_RAT    : AQVWCGSYRPEFAIQSIKTDVHSPLKYRVLGSLQNLPGFSEAFHCPRGSPMHPMNRCRIW : 774
SEP_MOUSE  : AQVWCGSYRPEFAVQSIKTDVHSPLKYRVLGSLQNLPGFSEAFHCPRGSPMHPMKRCRIW : 765

=====================catalytic domain======================
```

Figure 6A

Multiple alignment of human, rat and mouse SEP coding sequence showing catalytic domain

```
                    *        20         *        40         *        60
SEP_HUMAN : ATGGGGAAGTCCGAAGGCCCCGTGGGGATGGTGGAGAGCGCTGGCCGTGCAGGGCAGAAG :  60
SEP_RAT   : ATGGGGAAGTCGGAGAGCTCAGTGGGGATGATGGAGAGAGCGGACAACTGTGGGAGGAGG :  60
SEP_MOUSE : ---------------------------ATGGTGGAGAGAGCAGGCTGGTGTCGGAAGAAG :  33

*        80         *       100         *       120
SEP_HUMAN : CGCCCGGGGTTCCTGGAGGGGGGGCTGCTGCTGCTGCTG---CTGCTGGTGACCGCTGCC : 117
SEP_RAT   : CGCCTAGGCTTCGTGGAGTGTGGGCTGCTGGTACTGCTGACACTGCTGTTGATGGGAGCC : 120
SEP_MOUSE : TCCCCAGGCTTCGTGGAGTATGGGCTGATGTGCTGCTG---CTGCTGTTGCTGGGAGCC :  90

*       140         *       160         *       180
SEP_HUMAN : CTGGTGGCCTTGGGTGTCCTCTACGCCGACCGCAGAGGGAAGCAGCTGCCACGCCTTGCT : 177
SEP_RAT   : ATAGTGACTCTGGGTGTCTTCTACA------GCATAGGGAAGCAGCTGCCCCTCTTAAAT : 174
SEP_MOUSE : ATAGTGACTCTGGGTGTCTTCTACA------GCATAGGGAAGCAGCTGCCCCTCTTAACT : 144

*       200         *       220         *       240
SEP_HUMAN : AGCCGGCTGTGCTTCTTACAGGAGGAGAGGACCTTTGTAAAACGAAAACCCCGAGGGATC : 237
SEP_RAT   : AGCCTGCTGCACGTCTCCCGGCATGAGAGGACGGTTGTAAAACGAG--TCCTCAGAGATT : 232
SEP_MOUSE : AGCCTGCTACACTTCTCCTGGGATGAGAGGACGGTTGTAAAACGAG--CCCTCAGGGATT : 202

*       260         *       280         *       300
SEP_HUMAN : CCAGAGGCCCAAGAGGTGAGCGAGGTCTGCACCACCCCTGGCTGCGTGATAGCAGCTGCC : 297
SEP_RAT   : CATCGC------AGAAGAGTGACATCTGTACTACCCCAAGCTGCGTGATAGCAGCTGCC : 285
SEP_MOUSE : CATCAC------TGAAAAGTGACATCTGCACCACCCCAAGCTGTGTGATAGCAGCTGCC : 255

*       320         *       340         *       360
SEP_HUMAN : AGGATCCTCCAGAACATGGACCCGACCACGGAACCGTGTGACGACTTCTACCAGTTTGCA : 357
SEP_RAT   : AGAATCCTCCAGAACATGGACCAGTCAAAGAAACCCTGCGACAACTTCTATCAGTATGCT : 345
SEP_MOUSE : AGAATCCTCGAAAACATGGACCAATCGAGGAACCCCTGTGAAAACTTCTACCAGTACGCC : 315

*       380         *       400         *       420
SEP_HUMAN : TGCGGAGGCTGGCTGCGGCGCCACGTGATCCCTGAGACCAACTCAAGATACAGCATCTTT : 417
SEP_RAT   : TGCGGAGGCTGGCTACGGCACCATGTGATCCCCGAGACCAACTCCAGATACAGCGTCTTT : 405
SEP_MOUSE : TGCGGAGGCTGGCTGAGGCACCACGTGATCCCAGAGACCAACTCCCGATACAGCGTCTTT : 375

*       440         *       460         *       480
SEP_HUMAN : GACGTCCTCCGCGACGAGCTGGAGGTCATCCTCAAAGCGGTGCTGGAGAATTCGACTGCC : 477
SEP_RAT   : GACATCCTTCGGGATGAGCTGGAGGTCATCCTCAAAGGGGTGCTGGAGGATTCCTCTGTC : 465
SEP_MOUSE : GACATCCTGCGGGACGAGCTGGAGGTTATCCTCAAAGGGGTGCTGGAGGATTCCACTTCC : 435

*       500         *       520         *       540
SEP_HUMAN : AAGGACCGGCCGGCTGTGGAGAAGGCCAGGACGCTGTACCGCTCCTGCATGAACCAGAGT : 537
SEP_RAT   : CAGCACCGCCCAGCTGTGGAGAAGGCCAAGACACTGTACCGCTCCTGCATGAACCAGAGT : 525
SEP_MOUSE : CAGCATCGCCCGGCCGTGGAGAAGGCCAAGACACTATATCGCTCCTGCATGAACCAAAGT : 495

*       560         *       580         *       600
SEP_HUMAN : GTGATAGAGAAGCGAGGCTCTCAGCCCCTGCTGGACATCTTGGAGGTGGTGGGAGGCTGG : 597
SEP_RAT   : GTGATAGAGAAGAGAGACTCTGAGCCCCTGCTGAACGTCTTAGATATGATAGGAGGTTGG : 585
SEP_MOUSE : GTGATCGAGAAGAGAGACTCTGAGCCCCTGCTGAGCGTCTTAAAAATGGTAGGAGGTTGG : 555

*       620         *       640         *       660
SEP_HUMAN : CCGGTGGCCGATGGACAGGTGGAACGAGACCGTAGGACTCGAGTGGGAGCTGGAGCGGCAG : 657
SEP_RAT   : CCTGTAGCCATGGACAAGTGGAATGAGACCATGGGCCCCAAGTGGGAACTGGAGCGGCAG : 645
SEP_MOUSE : CCTGTGGCATTGGATAAGTGGAACGAGACCATGGGCCTCAAGTGGGAACTGGAGCGACAG : 615

*       680         *       700         *       720
SEP_HUMAN : CTGGCGCTGATGAACTCACAGTTCAACAGGCGCGTCCTCATCGACCTCTTCATCTGGAAC : 717
SEP_RAT   : TTGGCTGTGTTGAACTCGCAGTTCAACAGGCGCGTCCTCATCGACCTCTTCATCTGGAAT : 705
SEP_MOUSE : TTGGCTGTGTTGAACTCGCAGTTCAACAGGCGGGTCCTCATCGACCTCTTCATCTGGAAT : 675

*       740         *       760         *       780
SEP_HUMAN : GACGACCAGAACTCCAGCCGGCACATCATCTACATAGACCAGCCCACCTTGGGCATGCCC : 777
SEP_RAT   : GATGACCAGAACTCCAGCCGGCACGTCATCTACATAGACCAGCCCACCTTGGGCATGCCC : 765
SEP_MOUSE : GACGACCAGAACTCCAGCCGGCATGTCATCTACATAGACCAGCCCACCTTGGGCATGCCA : 735
```

Figure 6B

```
                      *         800         *         820         *         840
SEP_HUMAN  :  TCCCGAGAGTACTACTTCAACGGCGGCAGCAACCGGAAGGTGCGGGAAGCCTACCTGCAG  :  837
SEP_RAT    :  TCCCGGGAGTACTATTTCAAGGAAGACAGCCACCG---GGTACGGGAAGCCTACCTGCAG  :  822
SEP_MOUSE  :  TCCCGGGAGTACTATTTCCAGGAGGACAACAACCACAAGGTACGGAAAGCCTACCCGGAG  :  795

*         860         *         880         *         900
SEP_HUMAN  :  TTCATGGTGTCAGTGGCCACGTTGCTGCGGGAGGATGCAAACCTGCCCAGGGACAGCTGC  :  897
SEP_RAT    :  TTCATGACATCAGTGGCCACTATGCTGAGGAGAGACCTGAACCTGCCCGGGGAGACCGAT  :  882
SEP_MOUSE  :  TTCATGACGTCAGTGGCCACTATGCTTAGGAAAGACCAGAACCTGTCCAAGGAGAGCGCC  :  855

*         920         *         940         *         960
SEP_HUMAN  :  CTGGTGCAGGAGGACATGGTGCAGGTGCTGGAGCTGGAGACACAGCTGGCCAAGGCCACG  :  957
SEP_RAT    :  TTGGTGCAGGAGGAAATGGCACAGGTGCTGCATCTGGAGACACATCTGGCCAACGCCACG  :  942
SEP_MOUSE  :  ATGGTGCGGGAGGAGATGGCGGAGGTGCTGGAACTGGAGACGCATCTGGCCAACGCCACA  :  915

*         980         *        1000         *        1020
SEP_HUMAN  :  GTACCCCAGGAGGAGAGACACGACGTCATCGCCTTGTACCACCGGATGGGACTGGAGGAG  :  1017
SEP_RAT    :  GTCCCCCAGGAGAAAAGGCATGATGTCACCGCCCTGTATCACCGAATGGGCCTGGAGGAG  :  1002
SEP_MOUSE  :  GTCCCCCAGGAGAAAAGGCATGATGTCACTGCCCTGTACCACCGAATGGACCTGATGGAG  :  975

*        1040         *        1060         *        1080
SEP_HUMAN  :  CTGCAAAGCCAGTTTGGCCTGAAGGGATTTAACTGGACTCTGTTCATACAAACTGTGCTA  :  1077
SEP_RAT    :  CTGCAGGAAAGGTTTGGTCTGAAGGGGTTTAACTGGACTCTCTTCATACAAAACGTGCTG  :  1062
SEP_MOUSE  :  CTACAGGAAAGGTTTGGTCTGAAGGGGTTTAACTGGACTCTCTTCATACAAAACGTGTTG  :  1035

*        1100         *        1120         *        1140
SEP_HUMAN  :  TCCTCTGTCAAAATCAAGCTGCTGCCAGATGAGGAAGTGGTGGTCTATGGCATCCCCTAC  :  1137
SEP_RAT    :  TCTTCTGTGCAAGTTGAGCTGCTCCCGAATGAGGAGGTGGTGGTCTATGGCATCCCCTAC  :  1122
SEP_MOUSE  :  TCTTCTGTGGAAGTCGAGCTGTTCCCAGATGAGGAGGTGGTGGTCTACGGCATCCCCTAC  :  1095

*        1160         *        1180         *        1200
SEP_HUMAN  :  CTGCAGAACCTTGAAAACATCATCGACACCTACTCAGCCAGGACCATACAGAACTACCTG  :  1197
SEP_RAT    :  CTGGAGAATCTTGAGGAGATCATTGACGTCTTCCCAGCACAGACCTTGCAAAACTACCTG  :  1182
SEP_MOUSE  :  CTGGAGAATCTGGAGGATATCATTGATAGCTACTCAGCACGGACCATGCAGAACTACCTG  :  1155

*        1220         *        1240         *        1260
SEP_HUMAN  :  GTCTGGCGCCTGGTGCTGGACCGCATTGGTAGCCTAAGCCAGAGATTCAAGGACACACGA  :  1257
SEP_RAT    :  GTGTGGCGCCTGGTGCTAGATCGCATCGGCAGCCTGAGCCAGAGATTCAAAGAAGCGCGT  :  1242
SEP_MOUSE  :  GTATGGCGCCTGGTGCTAGATCGAATTGGCAGCCTGAGCCAGAGATTCAAAGAGGCGCGT  :  1215

*        1280         *        1300         *        1320
SEP_HUMAN  :  GTGAACTACCGCAAGGCGCTGTTTGGCACAATGGTGGAGGAGGTGCGCTGGCGTGAATGT  :  1317
SEP_RAT    :  GTGGACTACCGCAAGGCGCTGTACGGTACAACCATGGAGGAAGTACGCTGGCGGGAGTGT  :  1302
SEP_MOUSE  :  GTGGACTACCGCAAGGCGCTGTACGGCACGACCGTGGAGGAGGTACGCTGGCGAGAGTGT  :  1275

*        1340         *        1360         *        1380
SEP_HUMAN  :  GTGGGCTACGTCAACAGCAACATGGAGAACGCCGTGGGCTCCCTCTACTCAGGGGAGGCG  :  1377
SEP_RAT    :  GTCAGCTATGTCAACAGCAACATGGAGAGTGCCGTGGGCTCCCTCTACATCAAGCGGGCC  :  1362
SEP_MOUSE  :  GTCAGCTATGTCAACAGTAACATGGAGAGCGCCGTGGGCTCCCTCTACATCAAGCGGGCC  :  1335

*        1400         *        1420         *        1440
SEP_HUMAN  :  TTCCCTGGAGACAGCAAGAGCATGGTCAGAGAACTCATTGACAAGGTGCGGACAGTGTTT  :  1437
SEP_RAT    :  TTCTCCAAGGACAGCAAGAGCATAGTCAGTGAGCTTATCGAGAAGATACGGTCCGTGTTT  :  1422
SEP_MOUSE  :  TTCTCCAAGGACAGCAAGAGCACGGTCAGAGAGCTGATTGAGAAGATAAGGTCCGTGTTT  :  1395

*        1460         *        1480         *        1500
SEP_HUMAN  :  GTGGAGACGCTGGACGAGCTGGGCTGGATGGACGAGGAGTCCAAGAAGAAGGCGCAGGAG  :  1497
SEP_RAT    :  GTGGATAACCTGGACGAGTTGAACTGGATGGATGAGGAATCCAAGAAAAAGCCCAGGAA  :  1482
SEP_MOUSE  :  GTGGATAACCTGGATGAGCTGAACTGGATGGACGAGGAATCCAAGAAGAAGCCCAGGAA  :  1455

*        1520         *        1540         *        1560
SEP_HUMAN  :  AAGGCCATGAGCATCCGGGAGCAGATCGGGCACCCTGACTACATCCTGGAGGAGATGAAC  :  1557
SEP_RAT    :  AAGGCCTTGAATATCCGGGAACAGATCGGCTACCCTGACTACATTTTGGAAGACAATAAC  :  1542
SEP_MOUSE  :  AAGGCCATGAATATACGGGAACAGATTGGCTACCCTGACTACATTTTGGAAGATAACAAT  :  1515

*        1580         *        1600         *        1620
SEP_HUMAN  :  AGGCGCCTGGACGAGGAGTACTCCAATCTGAACTTCTCAGAGGACCTGTACTTTGAGAAC  :  1617
SEP_RAT    :  AGACACCTGGATGAGGAATACTCCAGTCTGACTTTCTCAGAGGACCTGTATTTTGAGAAC  :  1602
SEP_MOUSE  :  AAACACCTGGATGAGGAATACTCCAGTTTGACTTTCTATGAGGACCTGTATTTTGAGAAC  :  1575
```

Figure 6C

```
                    *        1640         *        1660         *        1680
SEP_HUMAN  : AGTCTGCAGAACCTCAAGGTGGGCGCCCAGCGGAGCCTCAGGAAGCTTCGGGAAAAGGTG : 1677
SEP_RAT    : GGGCTTCAGAACCTCAAGAACAATGCCCAAAGGAGCCTCAAGAAACTTCGGGAAAAGGTG : 1662
SEP_MOUSE  : GGACTTCAGAACCTCAAGAACAATGCCCAGAGGAGCCTCAAGAAGCTTCGGGAAAAGGTG : 1635

*        1700         *        1720         *        1740
SEP_HUMAN  : GACCCAAATCTCTGGATCATCGGGGCGGCGGTGGTCAATGCGTTCTACTCCCCAAACCGA : 1737
SEP_RAT    : GACCAGAATCTCTGGATCATTGGGGCTGCAGTGGTCAATGCATTCTACTCCCCAAACAGA : 1722
SEP_MOUSE  : GACCAGAATCTCTGGATCATCGGGGCTGCAGTGGTCAATGCATTCTACTCCCCAAACAGA : 1695

=====catalytic domain=====
                    *        1760         *        1780         *        1800
SEP_HUMAN  : AACCAGATTGTATTCCCTGCCGGGATCCTCCAGCCCCCCTTCTTCAGCAAGGAGCAGCCA : 1797
SEP_RAT    : AACCTGATCGTCTTTCCAGCGGGGATCCTCCAGCCACCCTTCTTCAGCAAGGACCAACCA : 1782
SEP_MOUSE  : AACCAGATCGTCTTTCCAGCAGGGATTCTCCAGCCGCCCTTCTTCAGCAAGGACCAACCA : 1755

======================catalytic domain=====================
                    *        1820         *        1840         *        1860
SEP_HUMAN  : CAGGCCTTGAACTTTGGAGGCATTGGGATGGTGATCGGGCACGAGATCACGCACGGCTTT : 1857
SEP_RAT    : CAGGCCTTGAATTTCGGGGGCATCGGGATGGTGATTGGACACGAGATCACACACGGCTTT : 1842
SEP_MOUSE  : CAGTCCTTGAATTTTGGGGGCATCGGGATGGTGATTGGGCACGAGATCACACACGGCTTT : 1815

======================catalytic domain=====================
*        1880         *        1900         *        1920
SEP_HUMAN  : GACGACAATGGCCGGAACTTCGACAAGAATGGCAACATGATGGATTGGTGGAGTAACTTC : 1917
SEP_RAT    : GATGATAACGGTCGGAACTTTGACAAGAATGGCAACATGCTGGACTGGTGGAGCAACTTC : 1902
SEP_MOUSE  : GATGATAATGGTCGTAACTTTGACAAGAACGGCAACATGCTGGACTGGTGGAGTAACTTC : 1875

======================catalytic domain=====================
*        1940         *        1960         *        1980
SEP_HUMAN  : TCCACCCAGCACTTCCGGGAGCAGTCAGAGTGCATGATCCTACCAGTACGGCAACTACTCC : 1977
SEP_RAT    : TCGGCCCGGCACTTCCGACAGCAGTCACAGTGTATGATTTATCAGTACAGCAACTTCTCT : 1962
SEP_MOUSE  : TCGGCCCGGCACTTCCAACAGCAGTCGCAATGCATGATCTATCAGTACGGCAACTTCTCT : 1935

======================catalytic domain=====================
                    *        2000         *        2020         *        2040
SEP_HUMAN  : TGGGACCTGGCAGACGAACAGAACGTGAACGGATTCAACACCCTTGGGGAAAACATTGCT : 2037
SEP_RAT    : TGGGAACTAGCAGACAACCAGAATGTGAACGGATTCAGCACCCTCGGGGAGAACATCGCC : 2022
SEP_MOUSE  : TGGGAACTAGCAGACAACCAGAATGTGAACGGATTCAGTTCCCTCGGGGAGAACATTGCC : 1995

======================catalytic domain=====================
                    *        2060         *        2080         *        2100
SEP_HUMAN  : GACAACGGAGGGGTGCGGCAAGCCTATAAGGCCTACCTCAAGTGGATGGCAGAGGGTGGC : 2097
SEP_RAT    : GACAACGGCGGTGTGCGGCAGGCATACAAGGCTTACCTACAGTGGCTAGCTGAAGGCGGC : 2082
SEP_MOUSE  : GACAACGGAGGTGTGCGACAGGCATACAAGGCTTACCTACGGTGGCTGGCTGATGGCGGC : 2055

======================catalytic domain=====================
                    *        2120         *        2140         *        2160
SEP_HUMAN  : AAGGACCAGCAGCTGCCCGGCCTGGATCTCACCCATGAGCAGCTCTTCTTCATCAACTAT : 2157
SEP_RAT    : AGAGACCAGAGACTGCCGGGACTGAACCTGACCTATGCTCAGCTTTTCTTCATTAACTAT : 2142
SEP_MOUSE  : AAAGATCAGCGACTGCCGGGACTGAACCTGACCTATGCCCAGCTTTTCTTCATCAACTAT : 2115

======================catalytic domain=====================
                    *        2180         *        2200         *        2220
SEP_HUMAN  : GCCCAGGTGTGGTGCGGGTCCTACCGGCCCGAGTTCGCCATCCAATCCATCAAGACAGAC : 2217
SEP_RAT    : GCCCAGGTGTGGTGTGGGTCCTACAGGCCGGAGTTCGCCATCCAGTCCATCAAGACAGAT : 2202
SEP_MOUSE  : GCCCAGGTGTGGTGTGGGTCCTATAGGCCGGAGTTCGCCGTCCAGTCCATCAAGACGGAC : 2175

======================catalytic domain=====================
                    *        2240         *        2260         *        2280
SEP_HUMAN  : GTCCACAGTCCCCTGAAGTACAGGGTACTGGGGTCGCTGCAGAACCTGGCCGCCTTCGCA : 2277
SEP_RAT    : GTCCACAGTCCTCTTAAGTACAGGGTGCTGGGCTCACTACAGAACCTACCAGGCTTCTCT : 2262
SEP_MOUSE  : GTCCACAGTCCTCTTAAGTACAGGGTGCTGGGCTCACTACAGAACCTGCCAGGCTTCTCT : 2235

======================catalytic domain=====================
                    *        2300         *        2320         *        2340
SEP_HUMAN  : GACACGTTCCACTGTGCCCGGGGCACCCCCATGCACCCCAAGGAGCGATGCCGCGTGTGG : 2337
SEP_RAT    : GAGGCGTTCCACTGCCCACGAGGCAGCCCCATGCACCCTATGAATCGATGTCGCATCTGG : 2322
SEP_MOUSE  : GAGGCATTCCACTGCCCACGAGGCAGCCCCATGCACCCCATGAAGCGATGTCGCATCTGG : 2295

======================catalytic domain=====================
```

Figure 6D

```
                     *         2060        *         2080        *         2100
SEP_MOUSE   : TGGGAACTAGCAGACAAGCAGAATCTGAACGGATTCACTTCCCTCGGGGAGAACATTGCC  : 1995
              TGGGAaCTaGCAGACAaAcCAGAAtGTGAACGGATTCAgcaCCCTCgGGGGAgAACATtGCc
              =================catalytic domain======================
                     *         2060        *         2080        *         2100
SEP_HUMAN   : GACAACGGAGGTGTGCCGCAACCCTATAACGGCTACCTCAAGTGGATGGCAGAGGGTGGC  : 2097
SEP_RAT     : GACAACGGCGGTGTGCCGGCAGGCATACAAGGCTTACCTACACTCCTAGCTGAAGGCGGC  : 2082
SEP_MOUSE   : GACAACGGACCTGTGCCACAGGCATACAAGGCTTACCTACGGTGGCTGGCTGATGGCGGC  : 2055
              GACAACGGaGGtGTGCGgCAgGCaTAcAAGGCtTACCTacaGTGGCtGgCtGA GGcGGC
              =================catalytic domain======================
                     *         2120        *         2140        *         2160
SEP_HUMAN   : AAGGACCAGCAGCTGCCCGGCCTGGATCTCACCCATGAGCAGCTCTTCTTCATCAACTAT  : 2157
SEP_RAT     : AGAGACCAGAGATTGTCGGGACCAAGCTGACCTATGGTCAGCTTTTCTTCATTAACTAT  : 2142
SEP_MOUSE   : AAAGATCAGCGACTGCCGGGACTGAACCTGACCTATGCTCAGCTTTTCTTCATCAACTAT  : 2115
              AaaGAcCAGcgaCTGCCgGGaCTGaAcCTGACCtATGc CAGCTtTTCTTCATCAACTAT
              =================catalytic domain======================
                     *         2180        *         2200        *         2220
SEP_HUMAN   : GCCCAGGTGTGGTGCGGGTCCTACAGGCCGAGTTCGCCATCCAATCCATCAAGACACAG  : 2217
SEP_RAT     : GCCCAGGTCTCGTGTGCGTCCTACAGGCCGGAGTTCGCCATCCAGTCCATCAAGACAGAT  : 2202
SEP_MOUSE   : GCCCAGGTCTCGTCTGGGTCCTATAGGCCGGAGTTCGCCGTCCAGTCCATCAAGACGGAC  : 2175
              GCCCAGGTGTGGTGtGGGTCCTAcaGGCCgGAGTTCGCCaTCCAgTCCATCAAGACaGAc
              =================catalytic domain======================
                     *         2240        *         2260        *         2280
SEP_HUMAN   : GTCCACAGTCCCCTGAAGTACAGGGTACTGGGGTCCCTGCAGAACCTGGCCCCCTTCGCA  : 2277
SEP_RAT     : GTCCACAGTCCTCTTAAGTACAGGGTGCTGGGCTCACTACAGAACCTACCAGGCTTCTCT  : 2262
SEP_MOUSE   : GTCCACAGTCCTCTTAAGTACAGGGTGCTGGGCTCACTACAGAACCTGCCAGGCTTCTCT  : 2235
              GTCCACAGTCCtCTtAAGTACAGGGTgCTGGGcTCaCTaCAGAACCTgcCaGgCTTCTcT
              =================catalytic domain======================
                     *         2300        *         2320        *         2340
SEP_HUMAN   : GACAGGTTCCACTGTGCCCAGGCACTCCATGCACCGAAGGATCGATCCGCGTGTGG  : 2337
SEP_RAT     : GAGGCGTTCCACTGGGCACGAGGCAGCCCATGCACCTATGAATCGATGTCGCATCTGG  : 2322
SEP_MOUSE   : GAGGCATTCCACTCCGCACCAGGCAGCCCATGCACCCATGAAGCGATGTCGCATCTGG  : 2295
              GAggCgTTCCACTGccCaCGaGGCAgCCCATGCACCCcAtGaAgCGATGtCGCAtCTGG
              =================catalytic domain======================
```

Phylogenetic analysis by Neighbour-Joining Distance method expressed as a radial tree derived from multiple alignment of whole SEP-like proteins Phylogenetic analysis by Neighbour-Joining Distance method expressed as a radial tree derived from the catalytic domain region of the multiple alignment

Figure 9

SEQ ID NO: 1

```
GGCACCAGCTCAGCCCCAAGCCACTGCTCTCCCATCCCAGTCCCTGGAAATCCAC
CCACTTGGCCCAGCTCACCCCAACTCCAACCCACTGGGACCCAGTCTCCAGGGGCCTGAC
TGTGGGCGGCAGCCACTCCTGAGTGAGCAAAGGTTCCTCCGCGGTGCTCTCCCGTCCAGA
GCCCTGCTGATGGGGAAGTCCGAAGGCCCCGTGGGGATGGTGGAGAGCGCTGGCCGTGCA
GGGCAGAAGCGCCCGGGGTTCCTGGAGGGGGGGCTGCTGCTGCTGCTGCTGGTGACC
GCTGCCCTGGTGGCCTTGGGTGTCCTCTACGCCGACCGCAGAGGGAAGCAGCTGCCACGC
CTTGCTAGCCGGCTGTGCTTCTTACAGGAGGAGAGGACCTTTGTAAAACGAAAACCCCGA
GGGATCCCAGAGGCCCAAGAGGTGAGCGAGGTCTGCACCACCCCTGGCTGCGTGATAGCA
GCTGCCAGGATCCTCCAGAACATGGACCCGACCACGGAACCGTGTGACGACTTCTACCAG
TTTGCATGCGGAGGCTGGCTGCGGCGCCACGTGATCCCTGAGACCAACTCAAGATACAGC
ATCTTTGACGTCCTCCGCGACGAGCTGGAGGTCATCCTCAAAGCGGTGCTGGAGAATTCG
ACTGCCAAGGACCGGCCGGCTGTGGACAAGGCCAGGACGCTGTACCGCTCCTGCATGAAC
CAGAGTGTGATAGAGAAGCGAGGCTCTCAGCCCCTGCTGGACATCTTGGAGGTGGTGGGA
GGCTGGCCGGTGGCGATGGACAGGTGGAACGAGACCGTAGGACTCGAGTGGGAGCTGGAG
CGGCAGCTGGCGCTGATGAACTCACAGTTCAACAGGCGCGTCCTCATCGACCTCTTCATC
TGGAACGACGACCAGAACTCCAGCCGGCACATCATCTACATAGACCAGCCCACCTTGGGC
ATGCCCTCCCGAGAGTACTACTTCAACGGCGGCAGCAACCGGAAGGTGCGGGAAGCCTAC
CTGCAGTTCATGGTGTCAGTGGCCACGTTGCTGCGGGAGGATGCAAACCTGCCCAGGGAC
AGCTGCCTGGTGCAGGAGGACATGGTGCAGGTGCTGGAGCTGGAGACACAGCTGGCCAAG
GCCACGGTACCCCAGGAGGAGAGACACGACGTCATCGCCTTGTACCACCGGATGGGACTG
GAGGAGCTGCAAAGCCAGTTTGGCCTGAAGGGATTTAACTGGACTCTGTTCATACAAACT
GTGCTATCCTCTGTCAAAATCAAGCTGCTGCCAGATGAGGAAGTGGTGGTCTATGGCATC
CCCTACCTGCAGAACCTTGAAAACATCATCGACACCTACTCAGCCAGGACCATACAGAAC
TACCTGGTCTGGCGCCTGGTGCTGGACCGCATTGGTAGCCTAAGCCAGAGATTCAAGGAC
ACACGAGTGAACTACCGCAAGGCGCTGTTTGGCACAATGGTGGAGGAGGTGCGCTGGCGT
GAATGTGTGGGCTACGTCAACAGCAACATGGAGAACGCCGTGGGCTCCCTCTACGTCAGG
GAGGCGTTCCCTGGAGACAGCAAGAGCATGGTCAGAGAACTCATTGACAAGGTGCGGACA
GTGTTTGTGGAGACGCTGGACGAGCTGGGCTGGATGGACGAGGAGTCCAAGAAGAAGGCG
CAGGAGAAGGCCATGAGCATCCGGGAGCAGATCGGGCACCTGACTACATCCTGGAGGAG
ATGAACAGGCGCCTGGACGAGGAGTACTCCAATCTGAACTTCTCAGAGGACCTGTACTTT
GAGAACAGTCTGCAGAACCTCAAGGTGGGCGCCCAGCGGAGCCTCAGGAAGCTTCGGGAA
AAGGTGGACCCAAATCTCTGGATCATCGGGGCGGCGGTGGTCAATGCGTTCTACTCCCCA
AACCGAAACCAGATTGTATTCCCTGCCGGGATCCTCCAGCCCCCCTTCTTCAGCAAGGAG
CAGCCACAGGCCTTGAACTTTGGAGGCATTGGGATGGTGATCGGGCACGAGATCACGCAC
GGCTTTGACGACAATGGCCGGAACTTCGACAAGAATGGCAACATGATGGATTGGTGGAGT
AACTTCTCCACCCAGCACTTCCGGGAGCAGTCAGAGTGCATGATCTACCAGTACGGCAAC
TACTCCTGGGACCTGGCAGACGAACAGAACGTGAACGGATTCAACACCCTTGGGGAAAAC
ATTGCTGACAACGGAGGGGTGCGGCAAGCCTATAAGGCCTACCTCAAGTGGATGGCAGAG
GGTGGCAAGGACCAGCAGCTGCCCGGCCTGGATCTCACCCATGAGCAGCTCTTCTTCATC
AACTATGCCCAGGTGTGGTGCGGGTCCTACCGGCCCGAGTTCGCCATCCAATCCATCAAG
ACAGACGTCCACAGTCCCCTGAAGTACAGGGTACTGGGGTCGCTGCAGAACCTGGCCGCC
TTCGCAGACACGTTCCACTGTGCCCGGGGCACCCCCATGCACCCAAGGAGCGATGCCGC
GTGTGGTAGCCAAGGCCCTGCCGCGCTGTGCGGCCCACGCCCACCTGCTGCTCGGAGGCA
TCTGTGCGAAGGTGCAGCTAGCGGCGACCCAGTGTACGTCCCGCCCCGGCCAACCATGCC
AAGCCTGCCTGCCAGGCCTCTGCGCCTGGCCTAGGGTGCAGCCACCTGCCTGACACCCAG
GGATGAGCAGTGTCCAGTGCAGTACCTGGACCGGAGCCCCTCCACAGACACCCGCGGGG
CTCAGTGCCCCGTCACAGCTCTGTAGAGACAATCAACTGTGTCCTGCCCACCCTCCAAG
GTGCATTGTCTTCCAGTATCTACAGCTTCAGACTTGAGCTAAGTAAATGCTTCAAAGAAA
AAAAAAAAAAAAAAAAAA
```

Figure 10

SEQ ID NO: 2

```
MGKSEGPVGMVESAGRAGQKRPGFLEGGLLLLLLLVTAALVALGVLYADRRGKQLPRLAS
RLCFLQEERTFVKRKPRGIPEAQEVSEVCTTPGCVIAAARILQNMDPTTEPCDDFYQFAC
GGWLRRHVIPETNSRYSIFDVLRDELEVILKAVLENSTAKDRPAVEKARTLYRSCMNQSV
IEKRGSQPLLDILEVVGGWPVAMDRWNETVGLEWELERQLALMNSQFNRRVLIDLFIWND
DQNSSRHIIYIDQPTLGMPSREYYFNGGSNRKVREAYLQFMVSVATLLREDANLPRDSCL
VQEDMVQVLELETQLAKATVPQEERHDVIALYHRMGLEELQSQFGLKGFNWTLFIQTVLS
SVKIKLLPDEEVVVYGIPYLQNLENIIDTYSARTIQNYLVWRLVLDRIGSLSQRFKDTRV
NYRKALFGTMVEEVRWRECVGYVNSNMENAVGSLYVREAFPGDSKSMVRELIDKVRTVFV
ETLDELGWMDEESKKKAQEKAMSIREQIGHPDYILEEMNRRLDEEYSNLNFSEDLYFENS
LQNLKVGAQRSLRKLREKVDPNLWIIGAAVVNAFYSPNRNQIVFPAGILQPPFFSKEQPQ
ALNFGGIGMVIGHEITHGFDDNGRNFDKNGNMMDWWSNFSTQHFREQSECMIYQYGNYSW
DLADEQNVNGFNTLGENIADNGGVRQAYKAYLKWMAEGGKDQQLPGLDLTHEQLFFINYA
QVWCGSYRPEFAIQSIKTDVHSPLKYRVLGSLQNLAAFADTFHCARGTPMHPKERCRVW
```

Figure 11

SEQ ID NO: 5

```
GGCACCAGCTCAGCCCCAAGCCACTGCTCTCCCATCCCAGTCCCTGGAAATCCAC
CCACTTGGCCCAGCTCACCCCAACTCCAACCCACTGGGACCCAGTCTCCAGGGGCCTGAC
TGTGGGCGGCAGCCACTCCTGAGTGAGCAAAGGTTCCTCCGCGGTGCTCTCCCGTCCAGA
GCCCTGCTGATGGGGAAGTCCGAAGGCCCCGTGGGATGGTGGAGAGCGCTGGCCGTGCA
GGGCAGAAGCGCCCGGGGTTCCTGGAGGGGGGCTGCTGCTGCTGCTGCTGGTGACC
GCTGCCCTGGTGGCCTTGGGTGTCCTCTACGCCGACCGCAGAGGGAAGCAGCTGCCACGC
CTTGCTAGCCGGCTGTGCTTCTTACAGGAGGAGAGGACCTTTGTAAAACGAAAACCCCGA
GGGATCCCAGAGGCCCAAGAGGTGAGCGAGGTCTGCACCACCCCTGGCTGCGTGATAGCA
GCTGCCAGGATCCTCCAGAACATGGACCCGACCACGGAACCGTGTGACGACTTCTACCAG
TTTGCATGCGGAGGCTGGCTGCGGCGCCACGTGATCCCTGAGACCAACTCAAGATACAGC
ATCTTTGACGTCCTCCGCGACGAGCTGGAGGTCATCCTCAAAGCGGTGCTGGAGAATTCG
ACTGCCAAGGACCGGCCGGCTGTGGAGAAGGCCAGGACGCTGTACCGCTCCTGCATGAAC
CAGAGTGTGATAGAGAAGCGAGGCTCTCAGCCCCTGCTGGACATCTTGGAGGTGGTGGGA
GGCTGGCCGGTGGCGATGGACAGGTGGAACGAGACCGTAGGACTCGAGTGGGAGCTGGAG
CGGCAGCTGGCGCTGATGAACTCACAGTTCAACAGGCGCGTCCTCATCGACCTCTTCATC
TGGAACGACGACCAGAACTCCAGCCGGCACATCATCTACATAGACCAGCCCACCTTGGGC
ATGCCCTCCCGAGAGTACTACTTCAACGGCGGCAGCAACCGGAAGGTGCGGGAAGCCTAC
CTGCAGTTCATGGTGTCAGTGGCCACGTTGCTGCGGGAGGATGCAAACCTGCCCAGGGAC
AGCTGCCTGGTGCAGGAGGACATGGTGCAGGTGCTGGAGCTGGAGACACAGCTGGCCAAG
GCCACGGTACCCCAGGAGGAGAGACACGACGTCATCGCCTTGTACCACCGGATGGGACTG
GAGGAGCTGCAAAGCCAGTTTGGCCTGAAGGGATTTAACTGGACTCTGTTCATACAAACT
GTGCTATCCTCTGTCAAAATCAAGCTGCTGCCAGATGAGGAAGTGGTGGTCTATGGCATC
CCCTACCTGCAGAACCTTGAAAACATCATCGACACCTACTCAGCCAGGACCATACAGAAC
TACCTGGTCTGGCGCCTGGTGCTGGACCGCATTGGTAGCCTAAGCCAGAGATTCAAGGAC
ACACGAGTGAACTACCGCAAGGCGCTGTTTGGCACAATGGTGGAGGAGGTGCGCTGGCGT
GAATGTGTGGGCTACGTCAACAGCAACATGGAGAACGCCGTGGGCTCCCTCTACGTCAGG
GAGGCGTTCCCTGGAGACAGCAAGAGCATGGTCAGAGAACTCATTGACAAGGTGCGGACA
GTGTTTGTGGAGACGCTGGACGAGCTGGGCTGGATGGACGAGGAGTCCAAGAAGAAGGCG
CAGGAGAAGGCCATGAGCATCCGGGAGCAGATCGGGCACCCTGACTACATCCTGGAGGAG
ATGAACAGGCGCCTGGACGAGGAGTACTCCAATCTGAACTTCTCAGAGGACCTGTACTTT
GAGAACAGTCTGCAGAACCTCAAGGTGGGCGCCCAGCGGAGCCTCAGGAAGCTTCGGGAA
AAGGTGGACCCAAATCTCTGGATCATCGGGGCGGCGGTGGTCAATGCGTTCTACTCCCCA
AACCGAAACCAGATTGTATTCCCTGCCGGGATCCTCCAGCCCCCCTTCTTCAGCAAGGAG
CAGCCACAGGCCTTGAACTTTGGAGGCATTGGGATGGTGATCGGGCACGAGATCACGCAC
GGCTTTGACGACAATGGCCGGAACTTCGACAAGAATGGCAACATGATGGATTGGTGGAGT
AACTTCTCCACCCAGCACTTCCGGGAGCAGTCAGAGTGCATGATCTACCAGTACGGCAAC
TACTCCTGGGACCTGGCAGACGAACAGAACGTGAACGGATTCAACACCCTTGGGGAAAAC
ATTGCTGACAACGGAGGGGTGCGGCAAGCCTATAAGGCCTACCTCAAGTGGATGGCAGAG
GGTGGCAAGGACCAGCAGCTGCCCGGCCTGGATCTCACCCATGAGCAGCTCTTCTTCATC
AACTATGCCCAGGTGTGGTGCGGGTCCTACCGGCCCGAGTTCGCCATCCAATCCATCAAG
ACAGACGTCCACAGTCCCCTGAAGTACAGGGTACTGGGGTCGCTGCAGAACCTGGCCGCC
TTCGCAGACACGTTCCACTGTGCCCGGGGCACCCCCATGCACCCCAAGGAGCGATGCCGC
GTGTGGTAGCCAAGGCCCTGCCGCGCTGTGCGGCCCACGCCCACCTGCTGCTCGGAGGCA
TCTGTGCGAAGGTGCAGCTAGCGGCGACCCAGTGTACGTCCCGCCCCGGCCAACCATGCC
AAGCCTGCCTGCCAGGCCTCTGCGCCTGGCCTAGGGTGCAGCCACCTGCCTGACACCCAG
GGATGAGCAGTGTCCAGTGCAGTACCTGGACCGGAGCCCCCTCCACAGACACCCGCGGGG
CTCAGTGCCCCGTCACAGCTCTGTAGAGACAATCAACTGTGTCCTGCCCACCCTCCAAG
GTGCATTGTCTTCCAGTATCTACAGCTTCAGACTTGAGCTAAGTAAATGCTTCAAAGAAA
AAAAAAAAAAAAAAAAA
```

COMPOUNDS FOR THE TREATMENT OF SEXUAL DYSFUNCTION

This application claims priority, under 35 U.S.C. § 119(e), from provisional application No. 60/220,908 filed Jul. 26, 2000.

TECHNICAL FIELD

The present invention relates to an enzyme. The present invention also relates to a nucleotide sequence encoding the same.

In particular, the present invention relates to a novel nucleic acid sequence encoding a novel soluble secreted endopeptidase (SEP).

The present invention also relates to the use of the novel nucleic acid and amino acid sequences in the diagnosis and prophylaxis and/or treatment of disease.

The present invention also relates, inter alia, to the use of the novel nucleic acid and amino acid sequences to evaluate and/or screen for agents that can modulate, preferably inhibit, more preferably selectively inhibit endopeptidase activity.

The present invention further relates to compounds and pharmaceutical compositions useful in the prophylaxis and/or treatment of sexual dysfunction, for example female sexual dysfunction (FSD), in particular female sexual arousal disorder (FSAD).

The present invention yet further relates to a method of prophylaxis and/or treatment of FSD, in particular FSAD.

The present invention also relates to assays to screen for compounds useful in the prophylaxis and/or treatment of FSD, in particular FSAD.

The present invention relates to compounds and pharmaceutical compositions for use in the prophylaxis and/or treatment of male sexual dysfunction, in particular male erectile dysfunction (MED). Male sexual dysfunction as referred to herein is meant to include ejaculatory disorders such as premature ejaculation, anorgasmia (unable to achieve orgasm), or desire disorders such as hypoactive sexual desire disorder (lack of interest in sex).

The present invention also relates to a method of prophylaxis and/or treatment of MED.

The present invention further relates to assays to screen for compounds useful in the prophylaxis and/or treatment of male sexual dysfunction, in particular MED.

BACKGROUND OF THE INVENTION

Human Soluble Secreted Endopeptidase (Human SEP)

Proteases form a large family of enzymes that cleave proteins and peptides at the peptide bond that forms the backbone of the peptide or protein chain. Proteases are found in all organisms from bacteria to man. In humans approximately 1% of all genes (400–1000) are predicted to encode protease enzymes. They participate in activation and maturation of nascent polypeptides, the degradation of misfolded and damaged proteins, and the controlled turnover of peptides and proteins both inside, and outside, the cell. Their activities are important for many processes including digestion, normal growth, endocrine function, wound healing, inflammation, angiogenesis, tissue remodelling during embryonic development, tumour metastasis, cardiovascular disease, neurological disease, and bacterial, parasitic, and viral infections.

Proteases can be broadly categorised on the basis of where they cleave their substrate. Exopeptidases, which include aminopeptidases, dipeptidyl peptidases, tripeptidases, carboxypeptidases, peptidyl-di-peptidases, dipeptidases and omega peptidases, cleave residues at the termini of their substrate. Endopeptidases, including serine proteases, cysteine proteases, and metalloendopeptidases, cleave at a sequence within the peptide.

An important group of endopeptidases known as zinc metalloproteases are characterised by having a requirement for the binding of a zinc ion in their catalytic site. Zinc metalloproteases can be subdivided into classes (for review see FEBS Letters 354 (1994) pp. 1–6), with one such class being the neprilysin (NEP)-like zinc metalloproteases (FASEB Journal, Vol 11, 1997 pp. 355–384). The NEP class includes at least 7 enzymes that are structurally related to each other (see later). They are typically membrane-bound, with a large carboxy-terminal extracellular domain, a short membrane-spanning region, and a short intracellular domain at the amino terminus. Known members of this family are neprilysin (also called NEP, CD10, CALLA, enkephalinase or EC 3.4.24.11), endothelin-converting enzymes (ECE-1 and ECE-2), PEX, KELL, X-converting enzyme/damage induced neural endopeptidase (XCE/DINE), and an enzyme identified in rodents called soluble secreted endopeptidase/neprilysin II (SEP/NEPII; Ghaddar, G et al, Biochem Journal, Vol 347, 2000, pp. 419–429; Ikeda, K et al, Journal Biological Chemistry, Vol 274, 1999, pp. 32469–32477; Tanja, O et al, Biochem Biophys Research Communication, Vol 271, 2000, pp. 565–570; International Patent Application WO 99/53077). The functions of the members of this class are thought to be related to peptidergic signalling. This is a process that occurs in most organisms, including humans, in which peptide molecules are used as "messengers" to elicit physiological responses. This typically involves the production and release of the peptide messenger by a specific cell, sometimes as an inactive precursor that is cleaved by a protease to become active. The active form of the peptide then binds a specific receptor on the surface of another cell where it elicits a response. The peptide is then inactivated by degradation by another protease.

NEP was the first member of this class to be discovered. NEP is a promiscuous protease in that it is able to proteolyse and inactivate many biological peptides, e.g. enkephalins, bradykinin and substance P. It usually cleaves the peptide on the amino-terminal side of a hydrophobic residue. NEP can be found in many tissues of the body and is most abundant in kidney. Its physiological functions are not fully understood, but one indication from the phenotype of NEP "knockout" mice is that it is involved in preventing endotoxic shock.

ECE-1 is a protein 37% identical to NEP. ECE-1 is broadly distributed throughout the body and converts the inactive precursor peptide big-endothelin into endothelin, which is a potent vasoconstrictor, important for maintaining vascular tone. The ECE-2 enzyme is derived form a separate gene to ECE-1, but its amino acid sequence is similar, with an overall homology of 59%. The physiological importance of ECE-2 to endothelin production is unclear. ECE-2 mRNA is present at much lower levels then ECE-1 mRNA and it has a different pH optimum to ECE-1, being inactive at neutral pH, and most active at pH 5.5.

The KELL enzyme is a clinically important member of the NEP class found in erythroid tissues. The antigens of the KELL blood group system reside in this protein which can cause haemolytic reaction to blood transfusions.

The PEX gene was identified as being genetically linked to a disorder called X-linked hypophosphatemic rickets, a dominant disorder typified by decreased renal tubular phosphate reabsorbtion. Based on its close homology to the other members of the NEP family (49–60%) it is also predicted to be a membrane-bound metalloprotease, but no substrate has yet been found.

XCE (Valdenaire, O et al, Molecular Brain Research, Vol 64, 1999, pp. 211–221), and its rat equivalent DINE (Kiryu-Seo, S et al, Proceedings of the National Academy of Science USA, 2000, pp. 4345–4350), are expressed predominantly in the central nervous system. DINE expression is up-regulated following neuronal damage, and this is thought to help prevent neuronal apoptosis, possibly as a result of the DINE-mediated proteolytic activation of anti-oxidant enzymes. A physiological substrate of XCE/DINE has also not yet been identified, but from their sequence they are clearly predicted to be proteases, and for DINE, this has been proven using a synthetic peptide substrate.

Rodent SEP and NEPII were discovered most recently. NEPII is likely to be a rat equivalent of SEP, which is a mouse enzyme, as they share 91% amino acid identity. They are the members of this class closest to NEP in their amino acid sequence, both being 54% identical to human NEP. The mRNA of both is highly abundant in the testis and can also be detected at low levels in a broad range of other tissues. In the case of rat NEPII, the mRNA has also been found at comparatively high levels in the brain and pituitary. When produced recombinantly in mammalian cells, both mouse SEP and rat NEPII can be found in the growth media. This suggests they could be secreted proteases that may be able to circulate and hence cleave peptides at other sites in the body. Mouse SEP and rat NEPII, like some other members of this class such as ECE-1, exhibit splice variation. In the case of mouse SEP and rat NEPII, this splice variation results in isoforms with alterations in sequences involved in membrane localisation and secretion. The physiological significance of this is unclear but it is likely there could be membrane-bound, circulating, and intracellular forms of these enzymes. Mouse SEP has been shown to be able to cleave a range of important biological peptides including enkephalin, endothelin, big-endothelin, Bradykinin and substance P. Like NEP, therefore, it has a fairly broad substrate specificity and may have several physiological functions in different tissues.

Enzymes in this NEP class, like other metalloprotease enzymes, have been shown to be amenable to inhibition by small drug-like molecules (for example, thiorphan and phosphoramidon). This, together with the emerging nature of the physiological function of some members of the NEP-like enzymes in modulating peptidergic signalling, makes them attractive targets for pharmaceutical intervention. NEP inhibitors have been developed for indications including cardiovascular disease, and it is likely that, as knowledge of their function increases further, specific inhibitors of NEP-like enzymes may have a role in the prophylaxis and/or treatment of many other indications such as sexual dysfunction (especially male sexual dysfunction, e.g. male erectile dysfunction (MED), and female sexual dysfunction (FSD), e.g. female sexual arousal disorder (FSAD)), preterm labour, pre-eclampsia, endometriosis, reproductive disorders (especially male and female infertility, polycystic ovarian syndrome, implantation failure), hypertension, heart failure, angina, renal insufficiency, cyclical oedema, hyperaldosteroneism, glaucoma, asthma, inflammation, leukemia, pain, epilepsy, affective disorders, dementia and geriatric confusion, obesity and gastrointestinal disorders (especially diarrhoea and irritable bowel syndrome), septic shock, the modulation of gastric acid secretion and the treatment of hyperreninaemia.

Sexual Dysfunction

Sexual dysfunction (SD) is a significant clinical problem which can affect both males and females. The causes of SD may be both organic as well as psychological. Organic aspects of SD are typically caused by underlying vascular diseases, such as those associated with hypertension or diabetes mellitus, by prescription medication and/or by psychiatric disease such as depression. Physiological factors include fear, performance anxiety and interpersonal conflict. SD impairs sexual performance, diminishes self-esteem and disrupts personal relationships thereby inducing personal distress. In the clinic, SD disorders have been divided into female sexual dysfunction (FSD) disorders and male sexual dysfunction (MSD) disorders (Melman et al 1999). FSD is best defined as the difficulty or inability of a woman to find satisfaction in sexual expression. Male sexual dysfunction (MSD) is generally associated with erectile dysfunction, also known as male erectile dysfunction (MED) (Benet et al 1994).

The compounds of the invention are particularly beneficial for the prophylaxis and/or treatment of sexual dysfunction in the male (e.g. male erectile dysfunction—MED) and in the female—female sexual dysfunction (FSD), e.g. female sexual arousal disorder (FSAD).

Female Sexual Dysfunction (FSD)

In accordance with the invention, FSD can be defined as the difficulty or inability of a woman to find satisfaction in sexual expression. FSD is a collective term for several diverse female sexual disorders (Leiblum, S. R. (1998). Definition and classification of female sexual disorders. *Int. J. Impotence Res.*, 10, S104–S106; Berman, J. R., Berman, L. & Goldstein, I. (1999). Female sexual dysfunction: Incidence, pathophysiology, evaluations and treatment options. *Urology*, 54, 385–391.). The woman may have lack of desire, difficulty with arousal or orgasm, pain with intercourse or a combination of these problems. Several types of disease, medications, injuries or psychological problems can cause FSD. Treatments in development are targeted to treat specific subtypes of FSD, predominantly desire and arousal disorders.

The categories of FSD are best defined by contrasting them to the phases of normal female sexual response: desire, arousal and orgasm (Leiblum, S. R. (1998). Definition and classification of female sexual disorders. *Int. J. Impotence Res.*, 10, S104–S106). Desire or libido is the drive for sexual expression. Its manifestations often include sexual thoughts either when in the company of an interested partner or when exposed to other erotic stimuli. Arousal is the vascular response to sexual stimulation, an important component of which is genital engorgement and includes increased vaginal lubrication, elongation of the vagina and increased genital sensation/sensitivity. Orgasm is the release of sexual tension that has culminated during arousal.

Hence, FSD occurs when a woman has an inadequate or unsatisfactory response in any of these phases, usually desire, arousal or orgasm. FSD categories include hypoactive sexual desire disorder, sexual arousal disorder, orgasmic disorders and sexual pain disorders. Although the compounds of the invention will improve the genital response to sexual stimulation (as in female sexual arousal disorder), in doing so it may also improve the associated pain, distress and discomfort associated with intercourse and so treat other female sexual disorders.

Thus, in accordance with a preferred aspect of the invention, there is provided use of a compound of the invention in the preparation of a medicament for the treatment or prophylaxis of hypoactive sexual desire disorder, sexual arousal disorder, orgasmic disorder and sexual pain disorder, more preferably for the treatment or prophylaxis of sexual arousal disorder, orgasmic disorder, and sexual pain disorder, and most preferably in the treatment or prophylaxis of sexual arousal disorder.

Hypoactive sexual desire disorder is present if a woman has no or little desire to be sexual, and has no or few sexual thoughts or fantasies. This type of FSD can be caused by low testosterone levels, due either to natural menopause or to surgical menopause. Other causes include illness, medications, fatigue, depression and anxiety.

Female sexual arousal disorder (FSAD) is characterised by inadequate genital response to sexual stimulation. The genitalia do not undergo the engorgement that characterises normal sexual arousal. The vaginal walls are poorly lubricated, so that intercourse is painful. Orgasms may be impeded. Arousal disorder can be caused by reduced oestrogen at menopause or after childbirth and during lactation, as well as by illnesses, with vascular components such as diabetes and atherosclerosis. Other causes result from treatment with diuretics, antihistamines, antidepressants e.g. selective serotonin re-uptake inhibitors (SSRIs) or antihypertensive agents.

Sexual pain disorders (includes dyspareunia and vaginismus) is characterised by pain resulting from penetration and may be caused by medications which reduce lubrication, endometriosis, pelvic inflammatory disease, inflammatory bowel disease or urinary tract problems.

The prevalence of FSD is difficult to gauge because the term covers several types of problem, some of which are difficult to measure, and because the interest in treating FSD is relatively recent. Many women's sexual problems are associated either directly with the female ageing process or with chronic illnesses such as diabetes and hypertension.

Because FSD consists of several subtypes that express symptoms in separate phases of the sexual response cycle, there is not a single therapy. Current treatment of FSD focuses principally on psychological or relationship issues. Treatment of FSD is gradually evolving as more clinical and basic science studies are dedicated to the investigation of this medical problem. Female sexual complaints are not all psychological in pathophysiology, especially for those individuals who may have a component of vasculogenic dysfunction (e.g. FSAD) contributing to the overall female sexual complaint. There are at present no drugs licensed for the treatment of FSD. Empirical drug therapy includes oestrogen administration (topically or as hormone replacement therapy), androgens or mood-altering drugs such as buspirone or trazodone. These treatment options are often unsatisfactory due to low efficacy or unacceptable side effects.

Since interest is relatively recent in treating FSD pharmacologically, therapy consists of the following: psychological counselling, over-the-counter sexual lubricants, and investigational candidates, including drugs approved for other conditions. These medications consist of hormonal agents, either testosterone or combinations of oestrogen and testosterone and more recently vascular drugs, that have proved effective in male erectile dysfunction (MED). None of these agents has yet been demonstrated to be effective in treating FSD.

As discussed, the compounds of the invention are particularly useful for the prophylaxis and/or treatment of female sexual arousal disorder (FSAD).

The Diagnostic and Statistical Manual (DSM) IV of the American Psychiatric Association defines Female Sexual Arousal Disorder (FSAD) as being:

" . . . a persistent or recurrent inability to attain or to maintain until completion of the sexual activity adequate lubrication-swelling response of sexual excitement. The disturbance must cause marked distress or interpersonal difficulty . . . ".

The arousal response consists of vasocongestion in the pelvis, vaginal lubrication and expansion and swelling of the external genitalia. The disturbance causes marked distress and/or interpersonal difficulty. Studies investigating sexual dysfunction in couples reveals that up to 76% of women have complaints of sexual dysfunction and that 30–50% of women in the USA experience FSD (Berman, J. R., Berman, L. A., Werbin, T. J. et al. (1999). Female sexual dysfunction: Anatomy, physiology, evaluation and treatment options. *Curr Opin Urology*, 9, 563–568).

FSAD is a highly prevalent sexual disorder affecting pre-, peri- and post-menopausal (± hormone replacement therapy (HRT)) women. It is associated with concomitant disorders such as depression, cardiovascular diseases, diabetes and urogenital (UG) disorders.

The primary consequences of FSAD are lack of engorgement/swelling, lack of lubrication and lack of pleasurable genital sensation. The secondary consequences of FSAD are reduced sexual desire, pain during intercourse and difficulty in achieving an orgasm.

It has recently been hypothesised that there is a vascular basis for at least a proportion of patients with symptoms of FSAD (Goldstein et al., Int. J. Impot. Res., 10, S84–S90, 1998) with animal data supporting this view (Park et al., Int. J. Impot. Res., 9, 27–37, 1997).

Drug candidates for treating FSAD, which are under investigation for efficacy, are primarily erectile dysfunction therapies that promote circulation to the male genitalia. They consist of two types of formulation, oral or sublingual medications (Apomorphine, Phentolamine, phosphodiesterase type 5 inhibitors e.g. Sildenafil), and prostaglandin ($PGE_1$) that are injected or administered transurethrally in men, and topically to the genitalia in women. However, none of these therapies have yet been shown to be effective in the treatment of FSAD.

Without being bound by theory, we believe that neuropeptides such as vasoactive intestinal peptide (VIP) are major neurotransmitter candidates in the control of the female sexual arousal response, especially in the control of genital blood flow. VIP and other neuropeptides are degraded/metabolised by SEP. Thus, SEP inhibitors will potentiate the endogenous vasorelaxant effect of VIP released during arousal. This will lead to a prophylaxis and/or treatment of FSAD, such as through enhanced genital blood flow and thence genital engorgement. We have shown that inhibitors of SEP enhance pelvic nerve-stimulated and VIP-induced increases in vaginal and clitoral blood flow. In addition, we have shown that SEP inhibitors enhance VIP and nerve-mediated relaxations of isolated vagina wall.

Thus the present invention is advantageous as it helps provide a means for restoring a normal sexual arousal response—namely increased genital blood flow leading to vaginal, clitoral and labial engorgement. This will result in increased vaginal lubrication via plasma transudation, increased vaginal compliance and increased genital sensitivity. Hence, the present invention provides a means to restore, or potentiate, the normal sexual arousal response.

By female genitalia herein we mean: "The genital organs consist of an internal and external group. The internal organs are situated within the pelvis and consist of ovaries, the uterine tubes, uterus and the vagina. The external organs are superficial to the urogenital diaphragm and below the pelvic arch. They comprise the mons pubis, the labia majora and minora pudendi, the clitoris, the vestibule, the bulb of the vestibule, and the greater vestibular glands" (Gray's Anatomy, C.D. Elemente, 13$^{th}$ American Edition).

R. J. Levin teaches us that because " . . . male and female genitalia develop embryologically from the common tissue anlagen, [that] male and female genital structures are argued to be homologues of one another. Thus the clitoris is the penile homologue and the labia homologues of the scrotal sac . . . ." (Levin, R. J. (1991), *Exp. Clin. Endocrinol.*, 98, 61–69).

Male Erectile Dysfunction (MED)

It is known that some individuals can suffer from male erectile dysfunction (MED).

Male erectile dysfunction (MED) is defined as:
" . . . the inability to achieve and/or maintain a penile erection for satisfactory sexual performance (NIH Consensus Development Panel on Impotence, 1993) . . . ".

It has been estimated that the prevalence of erectile dysfunction (ED) of all degrees (minimal, moderate and complete impotence) is 52% in men 40 to 70 years old, with higher rates in those older than 70 (Melman et al 1999). The condition has a significant negative impact on the quality of life of the patient and their partner, often resulting in increased anxiety and tension which leads to depression and low self esteem. Whereas two decades ago, MED was primarily considered to be a psychological disorder (Benet et al 1994), it is now known that for the majority of patients there is an underlying organic cause. As a result, much progress has been made in identifying the mechanism of normal penile erection and the pathophysiology of MED.

Penile erection is a haemodynamic event which is dependent upon the balance of contraction and relaxation of the corpus cavernosal smooth muscle and vasculature of the penis (Lerner et al 1993). Corpus cavernosal smooth muscle is also referred to herein as corporal smooth muscle or in the plural sense corpus cavernosa. Relaxation of the corpus cavernosal smooth muscle leads to an increased blood flow into the trabecular spaces of the corpus cavernosa, causing them to expand against the surrounding tunica and compress the draining veins. This produces a vast elevation in blood pressure which results in an erection (Naylor, 1998).

The changes that occur during the erectile process are complex and require a high degree of co-ordinated control involving the peripheral and central nervous systems, and the endocrine system (Naylor, 1998). Corporal smooth muscle contraction is modulated by sympathetic noradrenergic innervation via activation of postsynaptic $\alpha_1$ adrenoceptors. MED may be associated with an increase in the endogenous smooth muscle tone of the corpus cavernosum. However, the process of corporal smooth muscle relaxation is mediated partly by non-adrenergic, non-cholinergic (NANC) neurotransmission. There are a number of other NANC neurotransmitters found in the penis, other than nitric oxide (NO), such as calcitonin gene related peptide (CGRP) and vasoactive intestinal peptide (VIP). The main relaxing factor responsible for mediating this relaxation is NO, which is synthesised from L-arginine by nitric oxide synthase (NOS) (Taub et al 1993; Chuang et al 1998). It is thought that reducing corporal smooth muscle tone may aid NO to induce relaxation of the corpus cavernosum. During sexual arousal in the male, NO is released from neurones and the endothelium and binds to and activates soluble guanylate cyclase (sGC) located in the smooth muscle cells and endothelium, leading to an elevation in intracellular cyclic guanosine 3',5'-monophosphate (cGMP) levels. This rise in cGMP leads to a relaxation of the corpus cavernosum due to a reduction in the intracellular calcium concentration ($[Ca^{2+}]_i$), via unknown mechanisms thought to involve protein kinase G activation (possibly due to activation of $Ca^{2+}$ pumps and $Ca^{2+}$-activated $K^+$ channels; Chuang et al., 1998).

Sildenafil citrate (also known as Viagra™) has recently been developed by Pfizer as the first oral drug treatment for MED. Sildenafil acts by inhibiting cGMP breakdown in the corpus cavernosa by selectively inhibiting phosphodiesterase 5 (PDE5), thereby limiting the hydrolysis of cGMP to 5'GMP (Boolel et al., 1996; Jeremy et al., 1997) and thereby increasing the intracellular concentrations of cGMP and facilitating corpus cavernosal smooth muscle relaxation.

Currently, all other available MED therapies on the market, such as treatment with prostaglandin based compounds i.e. alprostadil which can be administered intraurethrally (available from Vivus Inc., as Muse™) or via small needle injection (available from Pharmacia & Upjohn, as Caverject™), are either inconvenient and/or invasive. Other treatments include vacuum constriction devices, vasoactive drug injection or penile prostheses implantation (Montague et al., 1996). Although injectable vasoactive drugs show high efficacy, side effects such as penile pain, fibrosis and priapism are common, and injection therapy is not as convenient as oral therapy therefore sildenafil currently represents the most preferred therapy on the market.

There is no prior documented evidence for the expression or a functional role of SEP in the penis or corpus cavernosum or in the erectile mechanism/process.

There is also no prior documented evidence for a functional or biochemical effect for SEP inhibitors on the penis or corpus cavernosum or alternatively in the erectile mechanism/process.

There is no prior documented evidence for the expression or a functional role of SEP in the vagina or clitoral corpus cavernosum or in the female sexual arousal mechanism/process.

There is also no prior documented evidence for a functional or biochemical effect for SEP inhibitors in the vagina or clitoral corpus cavernosum or in the female sexual arousal mechanism/process.

Thus, a seminal finding of the present invention is the ability to treat an male or a female suffering from sexual dysfunction, in particular MED or FSAD, with use of a soluble secreted endopeptidase inhibitor (SEPi). Surprisingly the applicants have also found that inhibition of SEP with a SEPi significantly enhances the nerve-stimulated arousal process.

The present invention is advantageous as it provides a means for restoring a normal sexual arousal response—namely increased penile blood flow leading to erection of the penis in males and a increased vaginal clitoral blood flow leading to genital engorgement in females. Hence, the present invention provides a means to restore, or potentiate, the normal sexual arousal response.

References

Argiolas, A. et al (1995), Neuromodulation of penile erection. *Prog Neurobiol*. 47: 235–255.

Benet, A. E. et al (1994), Male erectile dysfunction assessment and treatment options. *Comp. Ther*. 20: 669–673.

Boolel, M. et al (1996). Sildenafil, a novel effective oral therapy for male erectile dysfunction. *Br. J. of Urology* 78: 257–261.

Carter A J. et al (1998). Effect of the selective phosphodiesterase type 5 inhibitor sildenafil on erectile dysfunction in the anesthetized dog. *J. Urol*. 160: 242–6.

Chiou, W. F. et al (1998). Relaxation of corpus cavernosum and raised intracavernous pressure by berberine in rabbit. *Br. J. Pharmacol*. 125: 1677–1684.

Jeremy, J. Y. et al (1997). Effects of sildenafil, a type-5 cGMP phosphodiesterase inhibitor, and papaverine on cyclic GMP and cyclic AMP levels in the rabbit corpus cavernosum in vitro. *Br. J. Urology* 79: 958–963.

Lerner, S. E. et al (1993). A review of erectile dysfunction: new insights and more questions. *J. Urology* 149: 1246–1255.

Melman, A. & Gingell, J. C. (1999). The epidemiology and pathophysiology of erectile dysfunction. *J. Urology* 161: 5–11.

Montague, D. et al (1996). Clinical guidelines panel on erectile dysfunction: Summary report on the treatment of organic erectile dysfunction. *J. Urology* 156: 2007–2011.

Naylor, A. M. (1998). Endogenous neurotransmitters mediating penile erection. *Br. J. Urology* 81: 424–431.

NIH Consensus Development Panel on Impotence (1993). NIH Consensus Conference *Impotence. J.A.M.A.* 270: 83.

Omote M. (1999). Pharmacological profiles of sildenafil (VIAGRA) in the treatment of erectile dysfunction: efficacy and drug interaction with nitrate. *Nippon Yakurigaku Zasshi.* 114:213–8.

Taub, H. C. et al (1993). Relationship between contraction and relaxation in human and rabbit corpus cavernosum. *Urology* 42: 698–704.

Traish A M, et al (1999). Effects of castration and androgen replacement on erectile function in a rabbit model. *Endocrinology.* 140: 1861–8.

SUMMARY OF THE INVENTION

In a broad aspect, the present invention relates to novel amino acid sequences. In this regard, a specific novel amino acid sequence has been identified and it is to be understood that the invention covers that sequence as well as novel variants, fragments, derivatives and homologues thereof.

In another broad aspect, the present invention relates to novel nucleic acid sequences. In this regard, a specific novel nucleic acid sequence has been identified and it is to be understood that the invention covers that sequence as well as novel variants, fragments, derivatives and homologues thereof.

Thus, in brief, some aspects of the present invention relate to:
1. Novel amino acids.
2. Novel nucleotide sequences.
3. Assays using said novel sequences.
4. Compounds/compositions identified by use of said assays.
5. Expression systems comprising or expressing said novel sequences.
6. Methods of prophylaxis and/or treatment based on said novel sequences.
7. Pharmaceutical compositions based on said novel sequences.

Other aspects concerning the amino acid sequence of the present invention and/or the nucleotide sequence of the present invention include: a construct comprising or capable of expressing the sequences of the present invention; a vector comprising or capable of expressing the sequences of the present invention; a plasmid comprising or capable of expressing the sequences of the present invention; a tissue comprising or capable of expressing the sequences of the present invention; an organ comprising or capable of expressing the sequences of the present invention; a transformed host comprising or capable of expressing the sequences of the present invention; and a transformed organism comprising or capable of expressing the sequences of the present invention. The present invention also encompasses methods of expressing the same, such as expression in a micro-organism; including methods for transferring the same.

In the following commentary references to "nucleotide sequence of the present invention" and "amino acid sequence of the present invention" refer respectively to any one or more of the nucleotide sequences presented or discussed herein and to any one or more of the amino acid sequences presented or discussed herein. Also, and as used herein, "amino acid sequence" refers to peptide or protein sequences and may refer to portions thereof. In addition, the term "amino acid sequence of the present invention" is synonymous with the phrase "polypeptide sequence of the present invention". Also, the term "nucleotide sequence of the present invention" is synonymous with the phrase "polynucleotide sequence of the present invention".

Other features and advantages of the invention will be apparent from the following detailed description and from the claims. While the invention is described in connection with specific embodiments, it will be understood that other changes and modifications that may be practiced are also part of this invention and are also within the scope of the appendant claims. This application is intended to cover any equivalents, variations, uses, or adaptations of the invention that follow, in general, the principles of the invention, including departures from the present disclosure that come within known or customary practice within the art, and that are able to be ascertained without undue experimentation. Additional guidance with respect to making and using nucleic acids and polypeptides is found in standard textbooks of molecular biology, protein science, and immunology (see, e.g., Davis et al., Basic Methods in Molecular Biology, Elsevir Sciences Publishing, Inc., New York, N.Y., 1986; Hames et al., Nucleic Acid Hybridization, IL Press, 1985; Molecular Cloning, Sambrook et al., Current Protocols in Molecular Biology, Eds. Ausubel et al., John Wiley and Sons; Current Protocols in Human Genetics, Eds. Dracopoli et al., John Wiley and Sons; Current Protocols in Protein Science, Eds. John E. Coligan et al., John Wiley and Sons; and Current Protocols in Immunology, Eds. John E. Coligan et al., John Wiley and Sons). All publications mentioned herein are incorporated by reference in their entireties.

DESCRIPTION OF THE FIGURES

FIGS. 1A–1J show an analysis of open reading frames (ORFs) of human SEP cDNA sequence (SEQ ID NOS:1 and 9–62).

FIG. 2 shows a comparison of human SEP to most closely related human proteins by pairwise alignment from the blastp algorithm.

FIG. 3 shows a comparison of human, rat and mouse sequences for SEP by pairwise alignment from blastp (protein) and fasta (coding nucleotide) algorithms.

FIGS. 4A–4C show multiple alignment of human SEP (SEQ ID NOS: 2) and related human proteins (SEQ ID NOS: 63–68) showing catalytic domain.

FIGS. 5A–5B show multiple alignment of human (SEQ ID NOS:2), rat (SEQ ID NOS:69) and mouse (SEQ ID NOS:70) SEP proteins showing catalytic domain.

FIGS. 6A–6C show multiple alignment of human (SEQ ID NOS: 71), rat (SEQ ID NOS: 72) and mouse (SEQ ID NOS:73) SEP coding sequence showing catalytic domain.

FIG. 9 shows the nucleotide sequence (cDNA) coding for human SEP (SEQ ID NO:1).

FIG. 10 shows the predicted human SEP protein sequence (SEQ ID NO: 2) based upon translation of SEQ ID NO: 1 sequence in +1 open reading frame.

FIG. 11 shows the nucleotide sequence (cDNA) coding for human SEP including highlighted (gray) 5' and 3' partial vector sequences (SEQ ID NO: 5).

DETAILED DESCRIPTION

Figure 7:
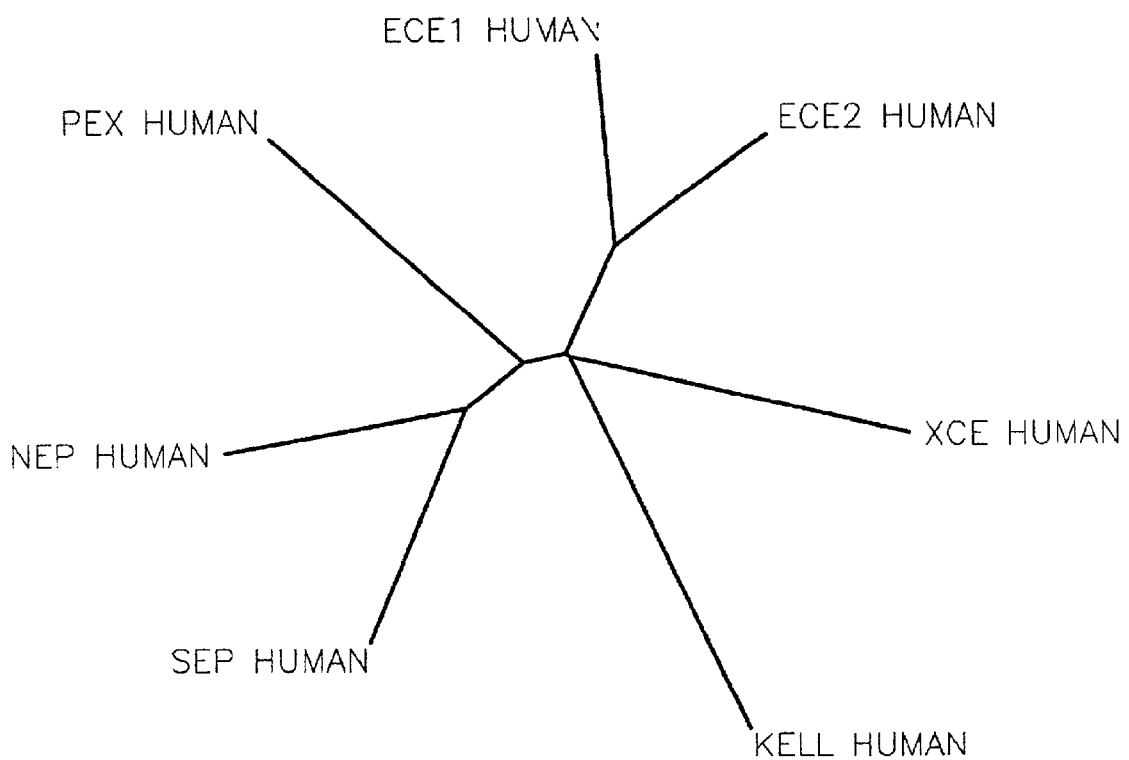
FIG. 7 shows a phylogenetic analysis by Neighbour-Joining Distance method expressed as a radial tree derived from multiple alignment of whole SEP-like proteins.
Figure 8:
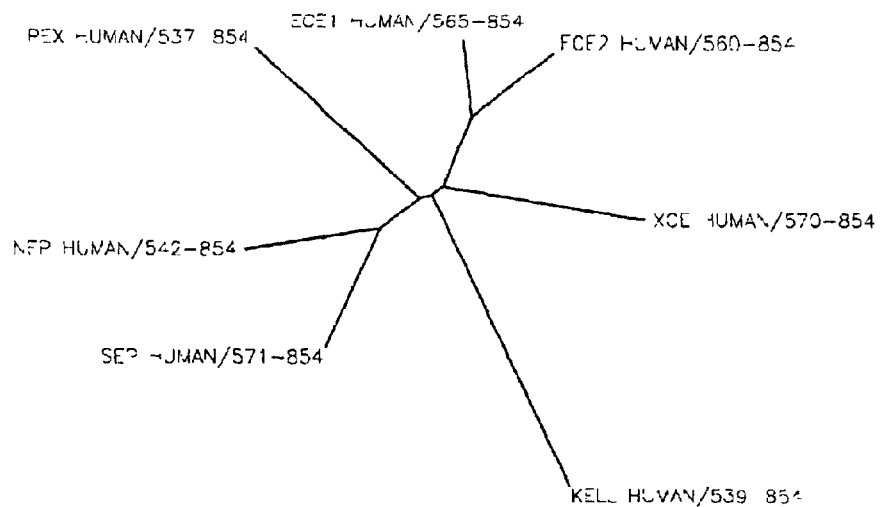
FIG. 8 shows a phylogenetic analysis by Neighbour-Joining Distance method expressed as a radial tree derived from the catalytic domain region of the multiple alignment.

According to one aspect of the present invention, there is provided an isolated and/or purified polynucleotide comprising one or more of:

(a) a polynucleotide encoding the polypeptide as set forth in SEQ ID NO: 2;

(b) a polynucleotide comprising a nucleotide sequence of SEQ ID NO: 1 or SEQ ID NO: 5;

(c) a polynucleotide encoding the polypeptide expressed by the DNA contained in NCIMB 41110;

(d) a polynucleotide comprising a nucleotide sequence that has at least 83% identity to the polynucleotide of any one of (a) to (c);

(e) a polynucleotide comprising a nucleotide sequence which is capable of hybridising to the polynucleotide of any one of (a) to (d);

(f) a complement to the polynucleotide of any one of (a) to (e); or (g) a polynucleotide fragment of the polynucleotide of any one of (a) to (f).

For the polypeptide of SEQ ID NO: 2, any one or more of the amino acids may be an analogue thereof.

The term "analogue" as used herein means a sequence having a sequence similar to that of SEQ ID NO: 2 but wherein non-detrimental (i.e. not detrimental to enzymatic activity) amino acid substitutions or deletions have been made.

Preferably, the polynucleotide comprises a nucleotide sequence that has at least 85% identity to the polynucleotide of any one of (a) to (c) above. More preferably, the polynucleotide comprises a nucleotide sequence that has at least 87% identity to the polynucleotide of any one of (a) to (c) above. Even more preferably, the polynucleotide comprises a nucleotide sequence that has at least 89% identity to the polynucleotide of any one of (a) to (c) above. Yet more preferably, the polynucleotide comprises a nucleotide sequence that has at least 90% identity to the polynucleotide of any one of (a) to (c) above. Most preferably, the polynucleotide comprises a nucleotide sequence that has at least 95% identity to the polynucleotide of any one of (a) to (c) above.

Preferably, the polynucleotide described above encodes a polypeptide which comprises the amino acid sequence MGKSEGPVG (SEQ ID NO: 6). Preferably said amino acid sequence MGKSEGPVG (SEQ ID NO: 6) is at or near the amino terminus of the polypeptide.

Preferably, the polynucleotide described above comprises the nucleotide sequence ATGGGGAAGTCCGAAGGC-CCCGTGGGG (SEQ ID NO: 7). Preferably said nucleotide sequence ATGGGGAAGTCCGAAGGCCCCGTGGGG (SEQ ID NO: 7) is at or near the 5' end of the polynucleotide.

The polynucleotide described above preferably encodes a soluble secreted endopeptidase (SEP), preferably human SEP.

The present invention also provides a polynucleotide probe or primer comprising at least 15 contiguous nucleotides of the polynucleotide described above, or the complement thereof. Preferably, the probe or primer can specifically distinguish said SEP coding sequence from other sequences.

The present invention yet further provides a vector comprising the polynucleotide described above.

According to a further aspect of the present invention, there is provided a host cell transformed or transfected with the vector described above. Preferably, the host cell is a mammalian, bacterial or yeast cell.

Further provided by the present invention is the transcribed RNA product of the polynucleotide described above.

Also provided by the present invention is an RNA molecule or a fragment thereof which is antisense in relation to said RNA product described above and is capable of hybridising thereto.

A ribozyme or zinc finger protein capable of binding to the polynucleotide described above is also provided by the present invention.

According to yet a further aspect of the present invention, there is provided a process for producing a polypeptide or fragment thereof comprising transforming or transfecting a host cell with the vector described above and culturing said transformed/transfected host cell in culture medium under conditions sufficient for the expression of said polypeptide or fragment. Preferably, said polypeptide or fragment is secreted into the culture medium. The process preferably further includes recovering the polypeptide or fragment from the culture.

There is also provided by the present invention a process for producing cells capable of expressing a polypeptide or fragment thereof comprising transforming or transfecting cells with the vector described above.

According to a further embodiment of the present invention, there are provided cells produced by the process described above. There is also provided the polypeptide or fragment thereof as described above produced by the above process.

According to another aspect of the present invention, there is provided a polypeptide having SEP activity comprising one or more of:

(a) a polypeptide having the deduced amino acid sequence translated from the polynucleotide sequence in SEQ ID NO: 1 or SEQ ID NO: 5 and variants, fragments, homologues, analogues and derivatives thereof;

(b) a polypeptide of SEQ ID NO: 2 and variants, fragments, homologues, analogues and derivatives thereof;

(c) a polypeptide encoded by the cDNA of NCIMB 41110 and variants, fragments, homologues, analogues and derivatives thereof; or (d) a polypeptide which has at least 78% identity to (i) the polypeptide encoded by the polynucleotide of SEQ ID NO: 1 or SEQ ID NO: 5, (ii) the polypeptide of SEQ ID NO: 2, or (iii) the polypeptide encoded by the cDNA of NCIMB 41110.

Preferably, the polypeptide comprises a polypeptide sequence that has at least 85%, preferably at least 90%, more preferably at least 95%, most preferably at least 98% identity to (i) the polypeptide encoded by the polynucleotide of SEQ ID NO: 1 or SEQ ID NO: 5, (ii) the polypeptide of SEQ ID NO: 2, or (iii) the polypeptide encoded by the cDNA of NCIMB 41110.

Preferably, the polypeptide described above comprises the amino acid sequence MGKSEGPVG. Preferably said amino acid sequence MGKSEGPVG (SEQ ID NO: 6) is at or near the amino terminus of the polypeptide.

Preferably, the polynucleotide which encodes the polypeptide described above comprises the nucleotide sequence ATGGGGAAGTCCGAAGGCCCCGTGGGG (SEQ ID NO: 7). Preferably said nucleotide sequence ATGGGGAAGTCCGAAGGCCCCGTGGGG (SEQ ID NO: 7) is at or near the 5' end of the polynucleotide.

There is also provided by the present invention an antibody against the polypeptide described above.

The present invention yet further provides a compound, which modulates the polypeptide described above. Preferably, the compound inhibits or selectively inhibits the polypeptide.

Also provided by the present invention is a pharmaceutical composition comprising the antibody or compound described above and one or more pharmaceutically acceptable carriers, diluents or excipients.

According to another aspect of the present invention, there is provided a method for identifying a candidate modulator, which binds to and/or modulates the polypeptide described above comprising contacting said polypeptide with a candidate modulator and determining whether modulation occurs.

Preferably, said method comprises:
  (a) contacting (i) a substrate peptide of the polypeptide described above with (ii) the polypeptide described above, in the presence of (iii) a candidate modulator of the polypeptide described above, wherein said substrate peptide is capable of providing a detectable signal in response to cleavage of said substrate peptide by the polypeptide described above; and
  (b) determining whether the cleavage of said substrate peptide by the polypeptide described above has been modulated or not by said candidate modulator by detecting the presence or absence of said detectable signal associated with said substrate peptide.

Preferably, said candidate modulator is a candidate inhibitor. More preferably, said substrate peptide is labelled with at least one fluorescent donor dye and at least one fluorescent acceptor dye and the assay used to detect candidate inhibitors of the polypeptide described above is a fluorescence resonance energy transfer (FRET) assay. Most preferably, said labelled substrate peptide is Rhodamine green-Gly-Gly-dPhe-Leu-Arg-Arg-Val-Cys(QSY™-7)-βAla-NH$_2$ (SEQ ID NO: 8).

Thus, according to a preferred aspect of the present invention, there is provided a method for identifying a candidate inhibitor which binds to and/or inhibits the polypeptide described above, which comprises:
  (a) contacting (i) a substrate peptide of the polypeptide described above with (ii) the polypeptide described above, in the presence of (iii) a candidate inhibitor of the polypeptide described above, wherein said substrate peptide is capable of providing a detectable signal in response to cleavage of said substrate peptide by the polypeptide described above; and
  (b) determining whether the cleavage of said substrate peptide by the polypeptide described above has been inhibited or not by said candidate inhibitor by detecting the presence or absence of said detectable signal associated with said substrate peptide.

Preferably, said substrate peptide is labelled with at least one fluorescent donor dye and at least one fluorescent acceptor dye and the assay used to detect candidate inhibitors of the polypeptide described above is a fluorescence resonance energy transfer (FRET) assay. Most preferably, said labelled substrate peptide is Rhodamine green-Gly-Gly-dPhe-Leu-Arg-Arg-Val-Cys(QSY™-7)-βAla-NH$_2$ (SEQ ID NO: 8).

The SEP FRET assay is based on an assay developed by Carvalho et al. for use with NEP (Carvalho et al., Annal. Biochem. 237, pp. 167–173 (1996)). The SEP FRET assay utilises a similar intramolecularly quenched fluorogenic peptide substrate, but with a novel combination of fluorogenic donor/acceptor dyes, specifically Rhodamine green (Molecular Probes, Inc., Eugene, Oreg., USA) and QSY™-7 (abbreviated hereafter as "QSY-7" or "QSY7"; Molecular Probes, Inc.).

The preparation of the synthetic labelled substrate peptide Rhodamine green-Gly-Gly-dPhe-Leu-Arg-Arg-Val-Cys (QSY7)-βAla-NH$_2$ (SEQ ID NO: 8) is detailed in the Experimental section (infra).

According to an alternative aspect of the present invention, there is provided a method for identifying a candidate modulator, which binds to and/or modulates the polypeptide described above comprising contacting said polypeptide with a candidate modulator and determining whether modulation occurs; wherein said method comprises:
  (a) contacting a candidate modulator with cells secreting the polypeptide described above, said polypeptide being associated with a second component capable of providing a detectable signal in response to the binding of a candidate modulator to said polypeptide; said contacting being under conditions sufficient to permit binding of candidate modulators to the polypeptide; and
  (b) identifying a candidate modulator capable of polypeptide binding by detecting the signal produced by said second component.

In addition, said method comprises:
  (a) contacting (i) a detectable first component known to bind to the polypeptide described above and (ii) a candidate modulator, with cells secreting the above polypeptide, said polypeptide being associated with a second component capable of providing a detectable signal in response to the binding of a candidate modulator to said polypeptide; said contacting being under conditions sufficient to permit binding of candidate modulators to the polypeptide; and
  (b) determining whether the first component binds to the polypeptide by detecting the absence or otherwise of a signal generated from the interaction of the first component with the polypeptide.

The candidate modulator identified by any of the above methods preferably binds to and/or inhibits the polypeptide described above, i.e. is preferably a candidate inhibitor.

In a further aspect, the present invention relates to an assay method for identifying an agent (hereinafter referred to as a SEP inhibitor or SEPi) that can be used to treat female sexual dysfunction, in particular FSAD, or male sexual dysfunction, in particular MED, the assay method comprising: determining whether a test agent can directly enhance the endogenous genital engorgement process or erectile process; wherein said enhancement is defined as a potentiation of genital blood flow or intracavernosal pressure (ICP) (and/or cavernosal blood flow) in the presence of a test agent as defined herein; such potentiation by a test agent is indicative that the test agent may be useful in the prophylaxis and/or treatment of female sexual dysfunction, in particular FSAD, or male sexual dysfunction, in particular MED and wherein said test agent is a SEPi.

By way of example, the present invention relates to an assay method for identifying an agent that can directly enhance the endogenous genital arousal or erectile process in order to treat female sexual dysfunction, in particular FSAD, or male sexual dysfunction, in particular MED, the assay method comprising: contacting a test agent which has a moiety capable of inhibiting the metabolic breakdown of a peptide (preferably a fluorescent labelled peptide, such as Rhodamine green-Gly-Gly-dPhe-Leu-Arg-Arg-Val-Cys (QSY7)-βAla-NH$_2$) (SEQ ID NO: 8), said peptide being normally metabolised by SEP; and measuring the activity and/or levels of peptide remaining after a fixed time (for example via fluorometric analysis); wherein the change in the level of the peptide measured by fluorescence is indicative of the potency (IC$_{50}$) of the test agent and is indicative that the test agent may be useful in the prophylaxis and/or treatment of female sexual dysfunction, in particular FSAD, or male sexual dysfunction, in particular MED; and wherein said agent is a SEPi.

In a further aspect, the present invention relates to a process comprising the steps of: (a) performing the assay according to the present invention; (b) identifying one or more agents that can directly enhance the endogenous genital arousal process or erectile process; and (c) preparing a quantity of those one or more identified agents; and wherein said agent is a SEPi.

With this aspect, the agent identified in step (b) may be modified so as to, for example, maximise activity and then step (a) may be repeated. These steps may be repeated until the desired activity or pharmacokinetic profile has been achieved.

Thus, in a further aspect, the present invention relates to a process comprising the steps of: (a1) performing the assay according to the present invention; (b1) identifying one or more agents that can directly enhance the endogenous genital arousal process or erectile process; (b2) modifying one or more of said identified agents; (a2) optionally repeating step (a1); and (c) preparing a quantity of those one or more identified agents (i.e. those that have been modified); and wherein said agent is a SEPi.

It is to be understood that any candidate modulator, candidate inhibitor, candidate selective inhibitor, agent (hereinafter referred to as a SEP inhibitor or SEPi), etc. that is identified using any assay (or modification thereof) described above is also deemed an aspect of the present invention.

Thus, the present invention provides a candidate modulator, candidate inhibitor, candidate selective inhibitor or agent identifed by any one of the methods (assays) described above.

As endopeptidases are involved in, inter alia, regulating bioactive peptide activity (e.g. peptidergic signalling processes), modulators (e.g. inhibitors, including selective inhibitors) of endopeptidases can find use in modulating such activity.

Some endopeptidases, such as ECE-1, are involved in proteolysis of biologically inactive peptides into their active form. Therefore, modulators (e.g. inhibitors, including selective inhibitors) of endopeptidases can find use in modulating such activity.

Human SEP may therefore be involved in regulating bioactive peptide activity and/or in proteolysis of biologically inactive peptides into their active form.

Consequently, the present invention provides an antibody, compound or composition which modulates the polypeptide described above for use as a pharmaceutical. Such antibodies, compounds or compositions, which can act as inhibitors or selective inhibitors of the polypeptide, can therefore find use in the therapeutic areas that concern aspects of regulating bioactive peptide activity, such as modulating peptidergic signalling processes and/or in proteolysis of biologically inactive peptides into their active form. Such therapeutically usefully areas include, but are not limited to, sexual dysfunction (e.g. female sexual dysfunction, in particular FSAD, or male sexual dysfunction, in particular MED), fertility disorders, neurodegenerative disorders such as Alzheimer's disease and stroke, cardiovascular diseases such as hypertension, wound healing/tissue repair, etc.

Accordingly, there is also provided the antibody, compound or composition described above for use as a pharmaceutical.

There is also provided the use of the above compound in the manufacture of a medicament in the prophylaxis and/or treatment of a patient having need to modulate the polypeptide described above.

There is also provided the use of the above compound in the manufacture of a medicament in the prophylaxis and/or treatment of a patient having need to inhibit or selectively inhibit the polypeptide described above. Preferably, said use of the above compound is in the manufacture of a medicament for the prophylaxis and/or treatment of sexual dysfunction. More preferably, said sexual dysfunction is male erectile dysfunction (MED) or female sexual dysfunction (FSD). Most preferably, said female sexual dysfunction (FSD) is female sexual arousal disorder (FSAD).

According to yet a further aspect of the invention, there is provided a method for the prophylaxis and/or treatment of a patient having need to modulate the polypeptide described above comprising administering to the patient a therapeutically effective amount of the above-described compound.

There is also provided a method for the prophylaxis and/or treatment of a patient having need to inhibit or selectively inhibit the polypeptide described above comprising administering to the patient a therapeutically effective amount of the above-described compound.

There is yet further provided a method for the prophylaxis and/or treatment of sexual dysfunction in a patient comprising administering to the patient a therapeutically effective amount of the above-described compound. Preferably, said sexual dysfunction is male erectile dysfunction (MED) or female sexual dysfunction (FSD). More preferably, said female sexual dysfunction (FSD) is female sexual arousal disorder (FSAD).

Preferably, said compound is a polypeptide and a therapeutically effective amount of the compound is administered by providing to the patient DNA encoding said compound and expressing said compound in vivo. More preferably, the compound is a polypeptide inhibitor and the modulation is inhibition or selective inhibition of the polypeptide described above.

Further provided by the present invention is use of the antibody described above in the manufacture of a medicament for the prophylaxis and/or treatment of a patient having need to modulate the polypeptide described above. Preferably, said modulation is inhibition or selective inhibition of the polypeptide described above. Preferably, said prophylaxis and/or treatment is for sexual dysfunction. More preferably, said sexual dysfunction is male erectile dysfunction (MED) or female sexual dysfunction (FSD). Most preferably, said female sexual dysfunction (FSD) is female sexual arousal disorder (FSAD).

There is also provided by the present invention a method for the prophylaxis and/or treatment of a patient having need to modulate the polypeptide described above, comprising administering to the patient a therapeutically effective amount of the antibody described above. Preferably, said modulation is inhibition or selective inhibition of the polypeptide described above. Preferably, said prophylaxis and/or treatment is for sexual dysfunction. More preferably, said sexual dysfunction is male erectile dysfunction (MED) or female sexual dysfunction (FSD). Most preferably, said female sexual dysfunction (FSD) is female sexual arousal disorder (FSAD).

A preferred aspect of the present invention relates to SEPi compounds and pharmaceutical compositions including SEPi compounds for use (or when in use) in the prophylaxis and/or treatment of female sexual dysfunction, in particular FSAD, or male sexual dysfunction, in particular MED. In said pharmaceutical compositions the SEPi is optionally admixed with a pharmaceutically acceptable carrier, diluent or excipient. Here, the composition (like any of the other compositions mentioned herein) may be packaged for subsequent use in the prophylaxis and/or treatment of male sexual dysfunction, in particular MED, or female sexual dysfunction, in particular FSAD.

In another aspect, the present invention relates to the use of an agent in the manufacture of a medicament (such as a pharmaceutical composition) for the prophylaxis and/or treatment of female sexual dysfunction, in particular FSAD, or male sexual dysfunction, in particular MED.

In a further aspect, the present invention relates to a method of treating a female suffering from female sexual dysfunction, in particular FSAD, or a male suffering from male sexual dysfunction, in particular MED; the method comprising delivering to the female or male a SEPi that is capable of enhancing the endogenous genital arousal/engorgement response in the clitoris and vagina or erectile process in the corpus cavernosum; wherein the SEPi is present in an amount to enhance the endogenous arousal/erectile process as defined hereinbefore; wherein the SEPi is optionally admixed with a pharmaceutically acceptable carrier, diluent or excipient; and wherein said SEPi is as herein defined.

In a further aspect, the present invention relates to a method of treating female sexual dysfunction, in particular FSAD, or male sexual dysfunction, in particular MED, by potentiating the nerve stimulated endogenous genital arousal process or erectile process in vivo (e.g. in rabbit) by measuring the vaginal/clitoral blood flow, ICP or cavernosal blood flow with an agent; wherein the agent is capable of directly inhibiting the metabolic breakdown of a fluorescent peptide (as mentioned hereinbefore and as detailed hereinafter) in an in vitro assay method; wherein the in vitro assay method is the assay method according to the present invention; and wherein said agent is a SEPi.

In a further aspect, the present invention relates to the use of an agent in the preparation of a pharmaceutical composition for the prophylaxis and/or treatment of female sexual dysfunction, in particular FSAD, or male sexual dysfunction, in particular MED, wherein the agent is capable of directly inhibiting the metabolic breakdown of a fluorescent peptide when assayed in vitro by the assay method according to the present invention; and wherein said agent is a SEPi.

Preferably, the SEP inhibitors (SEPi) for use in the prophylaxis and/or treatment of male and female sexual dysfunction, in particular MED and FSAD, according to the present invention have an $IC_{50}$ at less than 100 nanomolar, more preferably, at less than 50 nanomolar.

Preferably, the SEP inhibitors according to the present invention have greater than 30-fold, more preferably greater than 50-fold selectivity for SEP over neutral endopeptidase NEP EC 3.4.24.11 and angiotensin converting enzyme (ACE). This reduces the prospect of cardiovascular events (e.g. drop in blood pressure) when the SEPi is administered systemically (e.g. by mouth). Preferably the SEPi also has a greater than 100-fold selectivity over endothelin converting enzyme (ECE).

SEPi compounds are prepared according to the teachings presented in the Experimental section (infra). They are tested as agents and are found to be useful for enhancing the endogenous erectile process, and thereby being useful in the prophylaxis and/or treatment of MED and FSAD.

Without being limited to any particular theory it is proposed herein that by inhibiting SEP, other neuronally released vasoactive agents (most likely vasoactive intestinal protein (VIP)), that are released during sexual arousal, are enhanced. It is believed that use of the SEPi potentiates the effects of neuropeptides (most likely VIP) that are released during sexual stimulation, and hence potentiates the male erectile mechanism by increasing cavernosal blood flow and thus intracavernosal pressure and female engorgement by increasing genital blood flow.

It is further proposed that the use of the compounds according to the present invention acts via enhancing a non-NO-dependant NANC pathway to treat MED and FSAD, and to potentiate or facilitate the nitrergic signalling in the penis and vagina/clitoris.

Thus according to a preferred aspect of the invention, there is provided the use of a SEPi by systemic administration (preferably by mouth e.g. swallowable tablet or capsule, or a sublingual or buccal formulation) in the preparation of a medicament for the prophylaxis and/or treatment of male sexual dysfunction, in particular MED, or female sexual dysfunction, in particular FSAD.

In our studies we have developed a robust reproducible model of the physiology of male and female sexual arousal. This model uses an anaesthetised rabbit and employs Laser Doppler technologies to monitor intracavernosal pressure and genital blood flow whilst routinely recording cardiovascular parameters. We are capable of measuring small changes in intracavernosal pressure within the penis and vaginal (and even clitoral) blood flow induced by pelvic nerve stimulation or infusion of VIP in the absence and presence of test agents.

We believe that our animal model directly reflects the clinical data. Hence, this model can be used to study candidate agents for the prophylaxis and/or treatment of e.g. MED and FSAD, such as measuring enhancement of penile erection via increases in intracavernosal pressure and enhancement vaginal or clitoral blood flow. Thus, according to a further aspect, the present invention relates to an animal model used to identify agents capable of treating female sexual dysfunction, in particular FSAD, or male sexual dysfunction, in particular MED, said model comprising an anaesthetised female or male animal including means to measure changes in vaginal/clitoral blood flow, intracavernosal pressure and/or cavernosal blood flow of said animal following stimulation of the pelvic nerve thereof; and wherein said agent is a SEPi.

In a further aspect, the present invention relates to an assay method for identifying an agent that can directly enhance the endogenous genital arousal process or erectile process in order to treat FSAD or MED, the assay method comprising: administering an agent to the animal model of the present invention; and measuring the change in the endogenous genital arousal process or erectile process; wherein said change is defined as a potentiation of vaginal/clitoral blood flow, intracavernosal pressure (ICP) (and/or cavernosal blood flow) in the animal model in the presence of a test agent as defined; and wherein said agent is a SEPi.

In a further aspect, the present invention relates to a diagnostic method, the method comprising isolating a sample from a female or male; determining whether the sample contains an entity present in such an amount as to cause female sexual dysfunction, preferably FSAD, or male sexual dysfunction, preferably MED; wherein the entity has a direct effect on the endogenous genital arousal process in the female or erectile process in the corpus cavernosum of the male; and wherein said entity can be modulated to achieve a beneficial effect by use of an agent; and wherein said agent is a SEPi.

In a further aspect, the present invention relates to a diagnostic composition or kit comprising means for detecting an entity in an isolated female or male sample; wherein the means can be used to determine whether the sample contains the entity and in such an amount to cause female sexual dysfunction, preferably FSAD, or male sexual dysfunction, preferably MED, or is in an amount so as to cause sexual dysfunction, preferably FSAD or MED; wherein the entity has a direct effect on the endogenous genital arousal process or erectile process and wherein said entity can be modulated to achieve a beneficial effect by use of an agent; and wherein said agent is a SEPi.

According to yet a further aspect of the present invention, there are provided cells genetically engineered ex vivo or in vivo to overexpress, underexpress or to exhibit targeted insertion or deletion of the polypeptide of the present invention. Preferably, said cells genetically engineered in vivo are comprised within a non-human animal.

The present invention also provides cells deposited under Accession Number NCIMB 41110 and variants and mutants derivable therefrom capable of producing the polypeptide described above.

Also provided by the present invention is a method of elucidating the three-dimensional structure of the polypeptide described above, comprising the steps of: (a) purifying the polypeptide; (b) crystallising it, and (c) elucidating the structure, in particular by X-ray crystallography.

In a further aspect, the present invention also relates to a method of modelling the structure of the polypeptide described above, comprising the steps of: (a) aligning the sequence with a sequence of a protein of known three-dimensional structure, in particular rhodopsin; (b) mapping the detected sequence differences of the polypeptide described above onto the known structure, (c) deriving a homology model of the polypeptide described above. For ease of reference, these and further aspects of the present invention are now discussed under appropriate section headings. However, the teachings under each section are not necessarily limited to each particular section.

Human SEP Enzyme

As explained above, the present invention relates to a novel endopeptidase enzyme—which has been designated human soluble secreted endopeptidase (human SEP)—and to a nucleotide sequence encoding same. The present invention also relates to the use of the novel nucleic acid and amino acid sequences in the diagnosis and prophylaxis and/or treatment of disease. The present invention also relates to the use of the novel nucleic acid and amino acid sequences to evaluate and/or to screen for agents that can modulate (preferably inhibit or selectively inhibit) endopeptidase activity. The present invention further relates to genetically engineered host cells that comprise or express the novel nucleic acid and amino acid sequences to evaluate and/or to screen for agents that can modulate (preferably inhibit or selectively inhibit) endopeptidase activity.

Human SEP is believed to be present in, and obtainable from, a variety of sources.

By way of example, human SEP is found in any one or more of the cardiovascular system, the neurological system, the endocrine system and the testis.

We also believe that SEP is also present in a number of other sources—such as, for example: rodent (murine (Ikeda et al., Journal Biological Chemistry, Vol 274, 1999, pp. 32469–32477) and rat (NEP II—International Patent Application WO 99/53077)), bovine, ovine, porcine, and equine.

The human SEP may be the same as the naturally occurring form—for this aspect, preferably the human SEP is the non-native amino acid sequence (i.e. it is not present in its natural environment)—or is a variant, homologue, fragment or derivative thereof. In addition, or in the alternative, the human SEP is isolated human SEP and/or purified human SEP. The human SEP can be obtainable from, or produced by, any suitable source, whether natural or not, or it may be synthetic, semi-synthetic or recombinant.

The human SEP coding sequence may be the same as the naturally occurring form—for this aspect, preferably the human SEP coding sequence is the non-native nucleotide sequence (i.e. it is not present in its natural environment)—or is a variant, homologue, fragment or derivative thereof. In addition, or in the alternative, the human SEP coding sequence is an isolated human SEP coding sequence and/or a purified human SEP coding sequence. The human SEP coding sequence can be obtainable from, or produced by, any suitable source, whether natural or not, or it may be synthetic, semi-synthetic or recombinant.

Human SEP Activity and Screening

Human SEP and/or its coding sequence and/or a sequence capable of hybridising thereto is/are useful for testing the selectivity of drug candidates between different SEPs.

Human SEP is believed to be able to hydrolyse (proteolyse) various bioactive peptides.

It has been demonstrated (herein) that human SEP mRNA is most abundant in the testis compared to other tissues. This is in line with data published for mouse SEP (Ghaddar et al., Biochemical Journal, Vol 347, 2000, pp. 419–429), where the mRNA has been further localised to round and elongated spermatids.

Multiple different proteolytic activities have been identified in the testis previously, and in some cases they have been shown to be essential for testis function (e.g. ACE activity). It is likely from its abundance in this tissue that one possible physiological role of SEP will be related to a function of the testis (e.g. fertility).

Human SEP may hydrolyse a particular physiologically important biological peptide within the testis that is involved in an aspect of fertility or another function of the testis to either activate, or inactivate the peptide. The exact nature of this (predicted) physiological peptide has yet to be determined. However SEP can hydrolyse many biological peptides including big-endothelin, endothelin-1, angiotensin-I, substance P, bradykinin, enkephalins, and atrial natriuretic peptide (ANP). Several of these are known to function in the testis. Endothelin-1, for example, is found in the testis where it is involved in promoting seminiferous tubule contractility. Interestingly, the enzyme activity (ECE) detected within the testis that is thought to generate the endothelin-1 from big-endothelin is sensitive to the inhibitors phosphoramidon and thiorphan. Since mouse SEP and most probably human SEP are also sensitive to these inhibitors, this activity may be related to SEP rather than ECE. Compounds that inhibit human SEP activity may therefore lead to altered (increased or decreased) levels of endothelin within the testis, and this could potentially be useful for the prophylaxis and/or treatment of infertility or as a male contraceptive.

Vasoactive intestinal peptide (VIP) is another potential human SEP substrate that plays a role in the testis. VIP has been shown to increase blood flow in the testis and also to promote testicular steroidogenesis, as well as human sperm motility (Siow et al, Archives of Andrology, Vol 43, 1999, p. 6771). It is possible that drugs inhibiting human SEP activity could be useful in modulating VIP levels in the testis and hence testicular bloodflow, steroidogenesis or sperm motility.

Although human SEP mRNA is most abundant in testis, it can also be detected at lower levels in a variety of tissues using the sensitive method of reverse transcriptase-polymerase chain reaction (RT-PCR). In the mouse, SEP has been detected in heart, brain, spleen, lungs, kidney, intestine, and adrenal gland. The cDNA library screening approach that was used herein to isolate the full length human SEP cDNA sequence also identified human SEP cDNAs in libraries derived from human brain, placenta, small intestine and kidney tissue.

Human SEP enzyme can also be secreted from the cell. It is likely therefore that the human SEP protein, in addition to being abundant in the testis, will also be found at moderate levels in a wide range of other tissues throughout the body. In these tissues it is likely that human SEP will hydrolyse the biological peptide substrates mentioned above.

Drugs that inhibit the enzyme activity of SEP will therefore be likely to lead to changes in the levels of many of the human SEP substrates mentioned above in a variety of different tissues. As these human SEP substrates are usually biologically active molecules or their precursors which are often associated with peptidergic signalling processes, it is likely that human SEP inhibitors may be useful for the prophylaxis and/or treatment of many different disorders associated with peptidergic signalling that will most likely include, but is not limited to, sexual dysfunction (e.g. female sexual dysfunction, in particular FSAD, or male sexual dysfunction, in particular MED) and reproductive disorders, as well as other diseases/disorders such as neurodegenerative disorders (e.g. Alzheimer's disease and stroke), and cardiovascular diseases such as hypertension, etc.

Thus, human SEP and/or its coding sequence and/or a sequence capable of hybridising thereto may be useful for screening drug candidates for the prophylaxis and/or treatment of diseases associated with peptidergic signalling. In addition, it is believed that human SEP and/or its coding sequence and/or a sequence capable of hybridising thereto may be useful for screening drug candidates for the prophylaxis and/or treatment of diseases such as those described above.

Either or both of the nucleotide sequences coding for human SEP or the human SEP enzyme itself may be used to screen for agents that can affect SEP activity. In particular, the nucleotide sequence coding for human SEP itself may be used to screen for agents that can inhibit SEP activity. In addition, the nucleotide sequence coding for human SEP or the human SEP enzyme itself may be used to screen for agents that selectively affect SEP activity, such as selectively inhibit SEP activity.

Measurement of Human SEP Activity—Human SEP Assays

The enzymatic (proteolytic) activity of human SEP protein can be measured in an assay involving, for example, mixing a sample of the human SEP enzyme with a substrate peptide in a buffer solution (for example 50 mM HEPES; pH 7.4), incubating the mixture for a period of time (such as 1–3 hours) enough for human SEP to act to cleave a measurable portion of the peptide substrate to a product at a temperature suitable for SEP activity (typically 30–37° C.). Thereafter, the substrate and/or products of the proteolysis can be analysed to demonstrate that the substrate has been cleaved by the SEP enzyme.

The effect of candidate human SEP inhibitor compounds or control test compounds such as phosphoramidon and thiorphan that may alter the activity of human SEP can be measured in this type of assay by including them in the initial mixture at a range of suitable test concentrations, typically 0.1 nM to 50 $\mu$M.

Samples of SEP enzyme suitable for use in the above type of assay can be produced using a recombinant expression system. This will typically involve introducing an expression plasmid containing the human SEP cDNA or gene (e.g. the expression vector obtainable from NCIMB 41110) into a host organism or cell where the human SEP protein is then expressed. SEP protein may be released (i.e. secreted extracellularly) from the host into the growth media (e.g. if artificially expressed in mammalian cells), or retained in the cell (e.g. if artificially expressed in yeast or insect cells—where possible improper expression could result in the failure of human SEP to be secreted from the cell, therefore necessitating isolation from its intracellular location). Typically the host can be a yeast, insect cell, mammalian cell, or bacteria. The SEP enzyme can then be recovered from the culture media or host cell (e.g. by lysing the cells) which may necessitate using protein purification methods.

Human SEP enzyme for the aforementioned assay may also be purified from a suitable tissue source (if a sufficient quantity is obtainable). This tissue can include testis or brain.

Substrates suitable for use in the human SEP assay can be any peptide that SEP is able to cleave at a rate which is measurable in a useful period of time, e.g. 5 hours. Such substrate peptides can include, but are not limited to, peptides which are the same as, or similar to, biological peptides such as enkephalin, VIP, bradykinin, substance P, big endothelin, endothelin, angiotensin-I or ANP. The peptide can be modified to include a fluorescent, coloured, radioactive, or other chemical group that will facilitate measurement of the substrate and/or products before, during, or after the assay.

Preferred substrates suitable for use in the human SEP assay are SEP-cleavable synthetic peptides labelled with at least one fluorescent donor dye and at least one fluorescent acceptor dye and the assay used to detect inhibition of said SEP cleavage (proteolysis) is a fluorescence resonance energy transfer (FRET) assay. Most preferably, said labelled substrate peptide is a small fluorogenic peptide, preferably Rhodamine green-Gly-Gly-dPhe-Leu-Arg-Arg-Val-Cys (QSY7)-$\beta$Ala-NH$_2$ (SEQ ID NO: 8).

Such a FRET-based SEP assay is based on an assay developed by Carvalho et al. for use with NEP (Carvalho et al., Annal. Biochem. 237, pp. 167–173 (1996)). The SEP FRET assay utilises a similar intramolecularly quenched fluorogenic peptide substrate, but with a novel combination of fluorogenic donor/acceptor dyes, specifically Rhodamine green (Molecular Probes, Inc.) and QSY7 (Molecular Probes, Inc.).

The preparation of the synthetic labelled substrate peptide Rhodamine green-Gly-Gly-dPhe-Leu-Arg-Arg-Val-Cys (QSY7)-$\beta$Ala-NH$_2$ (SEQ ID NO: 8) is detailed in the Experimental section (infra).

Suitable buffers for use in human SEP assays can be any in which human SEP is found to be active and that does not otherwise interfere with the end result of the assays. Normally this will be a buffer that maintains a neutral pH. An example of such a buffer is 50 mM Tris Cl; pH 7.4. However, such a buffer is not preferred for use in a human SEP FRET assay as Tris is very prone to changes in pH due to temperature fluctuations. Therefore, a preferred buffer for use in a human SEP FRET assay is 50 mM HEPES; pH 7.4.

The method of measurement of the substrate and/or products in the human SEP assay will depend on the peptide substrate chosen and the nature of its modification. For example, if the substrate chosen contains a fluorescent group, a fluorimeter can be used. Similarly, if the substrate is radiolabelled, a scintillation counter may be used. Most substrates and products can be measured using high pressure liquid chromatography (HPLC) or mass spectrometry, and these would be the methods of choice if the substrate was not modified to include a radiolabel or fluorescence label.

Furthermore, the nucleotide sequence coding for human SEP or a sequence that is complementary thereto may also be used in assays to detect the presence of human SEP coding sequences in human cells. These assays would provide information regarding the tissue distribution of this enzyme and its biological relevance with respect to particular disease states.

The present invention also covers antibodies to human SEP (including a derivative, fragment, homologue or variant thereof). The antibodies for human SEP may be used in assays to detect the presence of human SEP in human cells. These assays would provide information regarding the tissue distribution of this enzyme and its biological relevance with respect to particular disease states.

The present invention also covers splice variants (isoenzymes) of the human SEP sequence. In particular, any one or more of the human SEP isoenzymes, the nucleotide sequences coding for same, the nucleotide sequences that are complementary to same, and the antibodies directed to same may be used in assays to screen for agents that selectively affect one of the isoenzymes. These assays would provide information regarding the tissue distribution of each of the isoenzymes and to provide information regarding the biological relevance of each of the isoenzymes with respect to particular disease states. These assays would also allow one of skill in the art to test for and identify agents that are useful to affect the expression of or activity of human SEP—such as in a particular tissue or in a particular disease state.

Polypeptide of the Present Invention

The term "polypeptide"—which is interchangeable with the term "protein"—includes single-chain polypeptide molecules as well as multiple-polypeptide complexes where individual constituent polypeptides are linked by covalent or non-covalent means.

Preferably, the polypeptide of the present invention is a single-chain polypeptide.

Polypeptides of the present invention may be in a substantially isolated form. It will be understood that the polypeptide may be mixed with carriers or diluents which will not interfere with the intended purpose of the polypeptide and still be regarded as substantially isolated. A polypeptide of the present invention may also be in a substantially purified form, in which case it will generally comprise the polypeptide in a preparation in which more than 90%, e.g. 95%, 98% or 99% of the polypeptide in the preparation is a polypeptide of the present invention. Polypeptides of the present invention may be modified for example by the addition of histidine residues to assist their purification.

Polypeptides of the present invention may be produced by synthetic means (e.g. as described by Geysen et al., 1996) or recombinantly, as described below.

In a preferred embodiment, the amino acid sequence per se of the present invention does not cover the native human SEP according to the present invention when it is in its natural environment and when it has been expressed by its native nucleotide coding sequence which is also in its natural environment and when that nucleotide sequence is under the control of its native promoter which is also in its natural environment. For ease of reference, we have called this preferred embodiment the "non-native amino acid sequence".

The terms "variant", "homologue", "derivative" or "fragment" in relation to the amino acid sequence for the enzyme of the present invention include any substitution of, variation of, modification of, replacement of, deletion of or addition of one (or more) amino acid from or to the sequence providing the resultant enzyme has SEP activity, preferably being at least as biologically active as the enzyme shown in attached SEQ ID NO: 2. In particular, the term "homologue" covers homology with respect to structure and/or function. With respect to sequence homology, preferably there is at least 78%, more preferably at least 85%, more preferably at least 90% homology to the sequence shown in SEQ ID NO: 2. More preferably there is at least 95%, more preferably at least 98%, homology to the sequence shown in SEQ ID NO: 2.

Typically, for the variant, homologue, derivative or fragment of the present invention, the types of amino acid substitutions that could be made should maintain the hydrophobicity/hydrophilicity of the amino acid sequence. Amino acid substitutions may be made, for example from 1, 2 or 3 to 10, 20 or 30 substitutions provided that the modified sequence retains the ability to act as a SEP enzyme in accordance with present invention. Amino acid substitutions may include the use of non-naturally occurring analogues, for example to increase blood plasma half-life.

The amino acid sequence of the present invention may be produced by expression of a nucleotide sequence coding for same in a suitable expression system.

In addition, or in the alternative, the protein itself could be produced using chemical methods to synthesize a human SEP amino acid sequence, in whole or in part. For example, peptides can be synthesized by solid phase techniques, cleaved from the resin, and purified by preparative high performance liquid chromatography (e.g. Creighton (1983) Proteins Structures and Molecular Principles, WH Freeman and Co., New York, N.Y., USA). The composition of the synthetic peptides may be confirmed by amino acid analysis or sequencing (e.g. the Edman degradation procedure).

Direct peptide synthesis can be performed using various solid-phase techniques (Roberge J Y et al, Science, Vol 269, 1995, pp. 202–204) and automated synthesis may be achieved, for example, using the ABI 431 A Peptide Synthesizer (Perkin Elmer, Boston, Mass., USA) in accordance with the instructions provided by the manufacturer. Additionally, the amino acid sequence of human SEP, or any part thereof, may be altered during direct synthesis and/or combined using chemical methods with a sequence from other subunits, or any part thereof, to produce a variant polypeptide.

In another embodiment of the invention, a human SEP natural, modified or recombinant sequence may be ligated to a heterologous sequence to encode a fusion protein. For example, for screening of peptide libraries for inhibitors of SEP activity, it may be useful to encode a chimeric SEP protein expressing a heterologous epitope that is recognised by a commercially available antibody. A fusion protein may also be engineered to contain a cleavage site located between a SEP sequence and the heterologous protein sequence, so that the SEP may be cleaved and purified away from the heterologous moiety.

Human SEP may also be expressed as a recombinant protein with one or more additional polypeptide domains added to facilitate protein purification. Such purification facilitating domains include, but are not limited to, metal chelating peptides such as histidine-tryptophan modules that allow purification on immobilised metals (Porath J, Protein Expr. Purif., Vol 3, 1992, pp. 263–281), protein A domains that allow purification on immobilised immunoglobulin, and the domain utilised in the FLAGS extension/affinity purification system (Immunex Corp, Seattle, Wash., USA). The inclusion of a cleavable linker sequence such as Factor XA or enterokinase (Invitrogen, San Diego, Calif., USA) between the purification domain and SEP is useful to facilitate purification.

A specific amino acid sequence of human SEP is shown in SEQ ID NO: 2. However, the present invention encompasses amino acid sequences encoding other members from the SEP family which would include amino acid sequences having at least 78% identity (more preferably at least 85% identity) to that specific amino acid sequence.

Polypeptides of the present invention also include fragments of the present amino acid sequence and variants thereof. Suitable fragments will be at least 5, e.g. at least 10, 12, 15 or 20 amino acids in size.

Polypeptides of the present invention may also be modified to contain one or more (e.g. at least 2, 3, 5 or 10) substitutions, deletions or insertions, including conserved substitutions. These aspects are discussed in a later section.

Nucleotide Sequence of the Present Invention

The term "nucleotide sequence" as used herein refers to an oligonucleotide sequence or polynucleotide sequence, and variants, homologues, fragments and derivatives thereof (such as portions thereof). The nucleotide sequence may be DNA or RNA which may be of genomic or synthetic or recombinant origin which may be double-stranded or single-stranded whether representing the sense or antisense strand.

Preferably, the term "nucleotide sequence" means DNA.

More preferably, the term "nucleotide sequence" means DNA prepared by use of recombinant DNA techniques (i.e. recombinant DNA).

In a preferred embodiment, the nucleotide sequence per se of the present invention does not cover the native nucleotide coding sequence according to the present invention in its natural environment when it is under the control of its native promoter which is also in its natural environment. For ease of reference, we have called this preferred embodiment the "non-native nucleotide sequence".

The nucleotide sequences of the present invention may include within them synthetic or modified nucleotides. A number of different types of modification to oligonucleotides are known in the art. These include methylphosphonate and phosphorothioate backbones, addition of acridine or polylysine chains at the 3' and/or 5' ends of the molecule. For the purposes of the present invention, it is to be understood that the nucleotide sequences described herein may be modified by any method available in the art. Such modifications may be carried out in to enhance the in vivo activity or life span of nucleotide sequences of the present invention.

The present invention also encompasses nucleotide sequences that are complementary to the sequences presented herein, or any derivative, fragment or variant thereof. If the sequence is complementary to a fragment thereof then that sequence can be used a probe to identify similar coding sequences in other organisms, etc.

The present invention also encompasses nucleotide sequences that are capable of hybridising to the sequences presented herein, or any derivative, fragment or variant thereof.

The present invention also encompasses nucleotide sequences that are capable of hybridising to the sequences that are complementary to the sequences presented herein, or any derivative, fragment or variant thereof.

The term "variant" also encompasses sequences that are complementary to sequences that are capable of hybridising to the nucleotide sequences presented herein.

Preferably, the term "variant" encompasses sequences that are complementary to sequences that are capable of hybridising under stringent conditions (e.g. 65° C. and 0.1×SSC {1×SSC=0.15 M NaCl, 0.015 Na$_3$ citrate pH 7.0}) to the nucleotide sequences presented herein.

The present invention also relates to nucleotide sequences that can hybridise to the nucleotide sequences of the present invention (including complementary sequences of those presented herein).

The present invention also relates to nucleotide sequences that are complementary to sequences that can hybridise to the nucleotide sequences of the present invention (including complementary sequences of those presented herein).

Also included within the scope of the present invention are polynucleotide sequences that are capable of hybridising to the nucleotide sequences presented herein under conditions of intermediate to maximal stringency.

In a preferred aspect, the present invention covers nucleotide sequences that can hybridise to the nucleotide sequence of the present invention, or the complement thereof, under stringent conditions (e.g. 65° C. and 0.1× SSC).

Exemplary nucleic acids can alternatively be characterised as those nucleotide sequences which encode a human SEP protein and hybridise to the DNA sequence shown in SEQ ID NO: 1 or SEQ ID NO: 5. Preferred are such sequences encoding human SEP which hybridise under high-stringency conditions to the sequence shown in SEQ ID NO: 1 or SEQ ID NO: 5 or the complement thereof.

Advantageously, the invention provides nucleic acid sequences which are capable of hybridising, under stringent conditions, to a fragment of the sequence shown in the SEQ ID NO: 1 or SEQ ID NO: 5 or the complement thereof. Preferably, the fragment is between 15 and 50 bases in length. Advantageously, it is about 25 bases in length.

The terms "variant", "homologue", "derivative" or "fragment" in relation to the nucleotide sequence coding for the preferred enzyme of the present invention include any substitution of, variation of, modification of, replacement of, deletion of or addition of one (or more) nucleic acid from or to the sequence providing the resultant nucleotide sequence codes for or is capable of coding for an enzyme having SEP activity, preferably being at least as biologically active as the enzyme encoded by the sequence shown in SEQ ID NO: 1 or SEQ ID NO: 5. In particular, the term "homologue" covers homology with respect to structure and/or function providing the resultant nucleotide sequence codes for or is capable of coding for an enzyme having SEP activity. With respect to sequence homology, preferably there is at least 83%, more preferably at least 85%, more preferably at least 90% homology to a nucleotide sequence coding for the amino acid sequence shown in SEQ ID NO: 2. More preferably there is at least 95%, more preferably at least 98% homology to a nucleotide sequence coding for the amino acid sequence shown in SEQ ID NO: 2. With respect to sequence homology, preferably there is at least 83%, more preferably at least 87%, more preferably at least 90% homology to the sequence shown in SEQ ID NO: 1 or SEQ ID NO: 5. More preferably there is at least 95%, more preferably at least 98%, homology to the sequence shown in SEQ ID NO: 1 or SEQ ID NO: 5.

As indicated, the present invention relates to a DNA sequence (preferably a cDNA sequence) encoding human SEP. In particular, the present invention relates to cDNA sequences encoding human SEP.

The present invention also relates to DNA segments comprising the DNA sequence shown in SEQ ID NO: 1 or SEQ ID NO: 5 or allelic variations thereof.

The present invention also relates to polypeptides produced by expression in a host cell into which has been incorporated the foregoing DNA sequences or allelic variations thereof.

The present invention also relates provides DNA comprising the DNA sequence shown in SEQ ID NO: 1 or SEQ ID NO: 5 or allelic variations thereof.

The present invention also relates to non-native DNA comprising the DNA sequence shown in SEQ ID NO: 1 or SEQ ID NO: 5 or allelic variations thereof.

A highly preferred aspect of the present invention relates to recombinant DNA comprising the DNA sequence shown in SEQ ID NO: 1 or SEQ ID NO: 5 or allelic variations thereof.

Polynucleotides of the present invention include nucleic acid sequences encoding the polypeptides of the present invention. It will be appreciated that a range of different polynucleotides encode a given amino acid sequence as a consequence of the degeneracy of the genetic code.

By knowledge of the amino acid sequences set out herein it is possible to devise partial and full-length nucleic acid sequences such as cDNA and/or genomic clones that encode the polypeptides of the present invention. For example, polynucleotides of the present invention may be obtained using degenerate polymerase chain reaction (PCR) which will use primers designed to target sequences encoding the amino acid sequences presented herein. The primers will typically contain multiple degenerate positions. However, to minimise degeneracy, sequences will be chosen that encode regions of the amino acid sequences presented herein containing amino acids such as methionine which are coded for by only one triplet. In addition, sequences will be chosen to take into account codon usage in the organism whose nucleic acid is used as the template DNA for the PCR procedure. PCR will be used at stringency conditions lower than those used for cloning sequences with single sequence (non-degenerate) primers against known sequences.

Nucleic acid sequences obtained by PCR that encode polypeptide fragments of the present invention may then be used to obtain larger sequences using hybridisation library screening techniques. For example a PCR clone may be labelled with radioactive atoms and used to screen a cDNA or genomic library from other species, preferably other mammalian species. Hybridisation conditions will typically be conditions of medium to high stringency (for example 0.03M sodium chloride and 0.03M sodium citrate at from about 50° C. to about 60° C.).

Degenerate nucleic acid probes encoding all or part of the amino acid sequence may also be used to probe cDNA and/or genomic libraries from other species, preferably other mammalian species. However, it is preferred to carry out PCR techniques initially to obtain a single sequence for use in further screening procedures.

In accordance with the present invention, polynucleotide sequences which encode human SEP, fragments of the polypeptide, fusion proteins or functional equivalents thereof, may be used to generate recombinant DNA molecules that direct the expression of human SEP in appropriate host cells. Due to the inherent degeneracy of the genetic code, other DNA sequences which encode substantially the same or a functionally equivalent amino acid sequence, may be used to clone and express human SEP. As will be understood by those of skill in the art, it may be advantageous to produce human SEP-encoding nucleotide sequences possessing non-naturally occurring codons. Codons preferred by a particular prokaryotic or eukaryotic host (Murray E et al, (1989), Nuc. Acids Res., 17:477–508) can be selected, for example, to increase the rate of human SEP expression or to produce recombinant RNA transcripts having desirable properties, such as a longer half-life, than transcripts produced from naturally occurring sequence. Polynucleotide sequences of the present invention obtained using the techniques described above may be used to obtain further homologous sequences and variants using the techniques described above. They may also be modified for use in expressing the polypeptides of the present invention in a variety of host cells systems, for example to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

Altered human SEP polynucleotide sequences which may be used in accordance with the invention include deletions, insertions or substitutions of different nucleotide residues resulting in a polynucleotide that encodes the same or a functionally equivalent SEP. The protein may also have deletions, insertions or substitutions of amino acid residues which produce a silent change and result in a functionally equivalent SEP. Deliberate amino acid substitutions may be made on the basis of similarity in polarity, charge, solubility, hydrophobicity, hydrophilicity, and/or the amphipathic nature of the residues as long as the biological activity of SEP is retained. For example, negatively charged amino acids include aspartic acid and glutamic acid; positively charged amino acids include lysine and arginine; and amino acids with uncharged polar head groups having similar hydrophilicity values include leucine, isoleucine, valine, glycine, alanine, asparagine, glutamine, serine, threonine, phenylalanine, and tyrosine.

Included within the scope of the present invention are alleles of human SEP. As used herein, an "allele" or "allelic sequence" is an alternative form of human SEP. Alleles result from a mutation, i.e. a change in the nucleic acid sequence, and generally produce altered mRNAs or polypeptides whose structure or function may or may not be altered. Any given gene may have none, one or many allelic forms. Common mutational changes which give rise to alleles are generally ascribed to deletions, additions or substitutions of amino acids. Each of these types of changes may occur alone, or in combination with the others, one or more times in a given sequence.

The nucleotide sequences of the present invention may be engineered in order to alter a human SEP coding sequence for a variety of reasons, including but not limited to, alterations which modify the cloning, processing and/or expression of the gene product. For example, mutations may be introduced using techniques which are well known in the art, e.g. site-directed mutagenesis to insert new restriction sites, to alter glycosylation patterns or to change codon preference.

Polynucleotides of the present invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the present invention as used herein.

Polynucleotides or primers of the present invention may carry a revealing label. Suitable labels include radioisotopes such as $^{32}$P or $^{35}$S, enzyme labels, or other protein labels such as biotin. Such labels may be added to polynucleotides or primers of the present invention and may be detected using by techniques known in the art.

Polynucleotides such as a DNA polynucleotide and primers according to the present invention may be produced recombinantly, synthetically, or by any means available to those of skill in the art. They may also be cloned by standard techniques.

In general, primers will be produced by synthetic means, involving a step wise manufacture of the desired nucleic acid sequence one nucleotide at a time. Techniques for accomplishing this using automated techniques are readily available in the art.

Longer polynucleotides will generally be produced using recombinant means, for example using PCR cloning techniques. This will involve making a pair of primers (e.g. of about 15–30 nucleotides) to a region of the nucleotide sequence which it is desired to clone, bringing the primers into contact with mRNA or cDNA obtained from, e.g., a fungal, plant or prokaryotic cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

DNA molecules may be modified to increase intracellular stability and half-life. Possible modifications include, but are not limited to, the addition of flanking sequences of the 5' and/or 3' ends of the molecule or the use of phosphorothioate or 2' O-methyl rather than phosphodiesterase linkages within the backbone of the molecule.

As mentioned earlier, the present invention also relates to nucleotide sequences that are capable of hybridising to all or part of the sequence shown in SEQ ID NO: 1 or SEQ ID NO: 5 or an allelic variation thereof. These nucleotide sequences may be used in antisense techniques to modify human SEP expression. Alternatively, these sequences (or portions thereof) can be used as a probe, or for amplifying all or part of such sequence when used as a PCR primer.

In addition to the recombinant DNA sequences, genomic sequences are also of utility in the context of drug discovery. It may be valuable to inhibit the mRNA transcription of a particular isoform rather than to inhibit its translated protein. This may be true with human SEP, if there are splice variants and wherein those different splice variants may be transcribed from different promoters.

Another utility of the invention is that the DNA sequences, once known, give the information needed to design assays to specifically detect isoenzymes or splice variants. Isoenzyme-specific PCR primer pairs are but one example of an assay that depends completely on the knowledge of the specific DNA sequence of the isoenzyme or splice variant. Such an assay allows detection of mRNA for the isoenzyme to access the tissue distribution and biological relevance of each isoenzyme to a particular disease state. It also allows identification of cell lines that may naturally express only one isoenzyme—a discovery that might obviate the need to express recombinant genes. If specific human SEP isoenzymes are shown to be associated with a particular disease state, the invention would be valuable in the design of diagnostic assays to detect the presence of isoenzyme mRNA.

An abnormal level of nucleotide sequences encoding a human SEP enzyme in a biological sample may reflect a chromosomal aberration, such as a nucleic acid deletion or mutation. Accordingly, nucleotide sequences encoding a human SEP enzyme provide the basis for probes which can be used diagnostically to detect chromosomal aberrations such as deletions, mutations or chromosomal translocations in the gene encoding human SEP. Human SEP gene expression may be altered in such disease states or there may be a chromosomal aberration present in the region of the gene encoding a human SEP.

In an alternative embodiment of the invention, the coding sequence of human SEP could be synthesized, in whole or in part, using chemical methods well known in the art (see Caruthers M H et al, (1980), Nuc. Acids Res. Symp. Ser., pp. 215–223; Horn T et al, (1980), Nuc. Acids Res. Symp. Ser., pp. 225–232).

Naturally Occurring

As used herein "naturally occurring" refers to a human SEP with an amino acid sequence found in nature.

Isolated/Purified

As used herein, the terms "isolated" and "purified" refer to molecules, either nucleic or amino acid sequences, that are removed from their natural environment and isolated or separated from at least one other component with which they are naturally associated. By "isolated or purified" is meant changed from the natural state "by the hand of man." If a polynucleotide or polypeptide exists in nature, then it is "isolated or purified" if it is changed and/or removed from its original environment. For example, an "isolated Ior purified" polynucleotide is separated from other polynucleotide sequence with which it is associated in nature. For example, a cDNA sequence that is removed from intronic sequence normally associated with the coding sequence is "isolated or purified." An "isolated or purified" polynucleotide sequence may be introduced into host cells in culture or in whole organisms and still be "isolated and purified," because the polynucleotide would not be in its naturally occurring form or environment. However, polynucleotide sequences as found in cDNA libraries are excluded from what is meant by "isolated or purified." An "isolated or purified" polypeptide is separated from at least one cellular component with which it is associated in nature. Preferably, the polypeptide is at least 60% free, more preferably, at least 75% free, and, most preferably, at least 90% from other components.

Biologically Active

As used herein "biologically active" refers to a human SEP according to the present invention—such as a recombinant human SEP—having a similar structural function (but not necessarily to the same degree), and/or similar regulatory function (but not necessarily to the same degree), and/or similar biochemical function (but not necessarily to the same degree) and/or immunological activity (but not necessarily to the same degree) of the naturally occurring human SEP. Specifically, a human SEP of the present invention has the ability to proteolytically cleave certain peptide substrates, which is one of the characteristic activities of the human SEP enzyme of the present invention.

Immunological Activity

As used herein, "immunological activity" is defined as the capability of the natural, recombinant or synthetic human SEP or any oligopeptide thereof, to induce a specific immune response in appropriate animals or cells and to bind with specific antibodies.

Derivative

The term "derivative" as used herein in relation to the amino acid sequence includes chemical modification of a human SEP. Illustrative of such modifications would be replacement of hydrogen by an alkyl, acyl, or amino group.

Deletion

As used herein a "deletion" is defined as a change in either nucleotide or amino acid sequence in which one or more nucleotides or amino acid residues, respectively, are absent.

Insertion/Addition

As used herein an "insertion" or "addition" is a change in a nucleotide or amino acid sequence which has resulted in the addition of one or more nucleotides or amino acid residues, respectively, as compared to the naturally occurring human SEP.

Substitution

As used herein "substitution" results from the replacement of one or more nucleotides or amino acids by different nucleotides or amino acids, respectively.

Homologue

The term "homologue" with respect to the nucleotide sequence of the present invention and the amino acid sequence of the present invention may be synonymous with allelic variations of the sequences.

In particular, the term "homology" as used herein may be equated with the term "identity". Here, sequence homology with respect to the nucleotide sequence of the present invention and the amino acid sequence of the present invention can be determined by a simple "eyeball" comparison (i.e. a strict comparison) of any one or more of the sequences with another sequence to see if that other sequence has at least 83% identity to the nucleotide sequence and at least 78% identity to the amino acid sequences. Relative sequence homology (i.e. sequence identity) can also be determined by commercially available computer programs that can calculate percentage (%) homology between two or more sequences. Typical examples of such computer programs are CLUSTAL or BLAST.

Percentage (%) homology may be calculated over contiguous sequences, i.e. one sequence is aligned with the other sequence and each amino acid in one sequence directly compared with the corresponding amino acid in the other sequence, one residue at a time. This is called an "ungapped" alignment. Typically, such ungapped alignments are performed only over a relatively short number of residues (for example less than 50 contiguous amino acids).

Although this is a very simple and consistent method, it fails to take into consideration that, for example, in an otherwise identical pair of sequences, one insertion or deletion will cause the following amino acid residues to be put out of alignment, thus potentially resulting in a large reduction in % homology when a global alignment is performed. Consequently, most sequence comparison methods are designed to produce optimal alignments that take into consideration possible insertions and deletions without penalising unduly the overall homology score. This is achieved by inserting "gaps" in the sequence alignment to try to maximise local homology.

However, these more complex methods assign "gap penalties" to each gap that occurs in the alignment so that, for the same number of identical amino acids, a sequence alignment with as few gaps as possible—reflecting higher relatedness between the two compared sequences—will achieve a higher score than one with many gaps. "Affine gap costs" are typically used that charge a relatively high cost for the existence of a gap and a smaller penalty for each subsequent residue in the gap. This is the most commonly used gap scoring system. High gap penalties will of course produce optimised alignments with fewer gaps. Most alignment programs allow the gap penalties to be modified. However, it is preferred to use the default values when using such software for sequence comparisons. For example when using the GCG Wisconsin Bestfit package (see below) the default gap penalty for amino acid sequences is -12 for a gap and -4 for each extension.

Calculation of maximum % homology therefore firstly requires the production of an optimal alignment, taking into consideration gap penalties. A suitable computer program for carrying out such an alignment is the GCG Wisconsin Bestfit package (University of Wisconsin, U.S.A.; Devereux et al., 1984, Nucleic Acids Research 12:387). Examples of other software that can perform sequence comparisons include, but are not limited to, the BLAST package (see Ausubel et al., 1999 ibid—Chapter 18), FASTA (Altschul et al., 1990, J. Mol. Biol., 403–410) and the GENEWORKS suite of comparison tools. Both BLAST and FASTA are available for off-line and on-line searching (see Ausubel et al., 1999 ibid, pages 7–58 to 7–60). However, for some applications it is preferred to use the GCG Bestfit program.

Although the final % homology can be measured in terms of identity, in some cases, the alignment process itself is typically not based on an all-or-nothing pair comparison. Instead, a scaled similarity score matrix is generally used that assigns scores to each pairwise comparison based on chemical similarity or evolutionary distance. An example of such a matrix commonly used is the BLOSUM62 matrix—the default matrix for the BLAST suite of programs. GCG Wisconsin programs generally use either the public default values or a custom symbol comparison table if supplied (see user manual for further details). It is preferred to use the public default values for the GCG package, or in the case of other software, the default matrix, such as BLOSUM62.

Once the software has produced an optimal alignment, it is possible to calculate % homology, preferably % sequence identity. The software typically does this as part of the sequence comparison and generates a numerical result.

As indicated, for some applications, sequence homology (or identity) may be determined using any suitable homology algorithm, using for example default parameters. For a discussion of basic issues in similarity searching of sequence databases, see Altschul et al. (1994) Nature Genetics 6:119–129. For some applications, the BLAST algorithm is employed, with parameters set to default values. The BLAST algorithm is described in detail at http://www.ncbi.nih.gov/BLAST/blast_help.html. Advantageously, "substantial homology" when assessed by BLAST equates to sequences which match with an EXPECT value of at least about e-7, preferably at least about e-9 and most preferably e-10 or lower. The default threshold for EXPECT in BLAST searching is usually 10.

Should Gap Penalties be used when determining sequence identity, then preferably the following parameters are used:

| FOR BLAST | |
| --- | --- |
| GAP OPEN | 5 |
| GAP EXTENSION | 2 |

| FOR CLUSTAL | DNA | PROTEIN | |
|---|---|---|---|
| WORD SIZE | 2 | 1 | K triple |
| GAP PENALTY | 10 | 10 | |
| GAP EXTENSION | 0.1 | 0.1 | |

Other computer program methods to determine identify and similarity between the two sequences include but are not limited to the GCG program package (Devereux et al., 1984, Nucleic Acids Research, 12: 387) and FASTA (Atschul et al, 1990, J. Molec. Biol., pp. 403–410).

Polypeptide Variants and Derivatives

The terms "variant" or "derivative" in relation to the amino acid sequences of the present invention includes any substitution of, variation of, modification of, replacement of, deletion of or addition of one (or more) amino acids from or to the sequence providing the resultant amino acid sequence has human SEP activity, preferably having at least the same activity as the polypeptide presented in SEQ ID NO: 2.

The sequences of the present invention may be modified for use in the present invention. Typically, modifications are made that maintain the human SEP activity of the sequence. Amino acid substitutions may be made, for example from 1, 2 or 3 to 10, 20 or 30 substitutions provided that the modified sequence retains the human SEP activity. Amino acid substitutions may include the use of non-naturally occurring analogues, for example to increase blood plasma half-life of a therapeutically administered polypeptide.

Conservative substitutions may be made, for example, according to the Table below. Amino acids in the same block in the second column and preferably in the same line in the third column may be substituted for each other:

| | | |
|---|---|---|
| ALIPHATIC | Non-polar | G A P |
| | | I L V |
| | Polar-uncharged | C S T M |
| | | N Q |
| | Polar-charged | D E |
| | | K R |
| AROMATIC | | H F W Y |

As indicated above, proteins of the invention are typically made by recombinant means, for example as described herein, and/or by using synthetic means using techniques well known to the skilled person such as solid phase synthesis. Variants and derivatives of such sequences include fusion proteins, wherein the fusion proteins comprise at least the amino acid sequence of the present invention being linked (directly or indirectly) to another amino acid sequence. These other amino acid sequences—which are sometimes referred to as fusion protein partners—will typically impart a favourable functionality—such as to aid extraction and purification of the amino acid sequence of the present invention. Examples of fusion protein partners include glutathione-S-transferase (GST), 6xHis, GAL4 (DNA binding and/or transcriptional activation domains) and β-galactosidase. It may also be convenient to include a proteolytic cleavage site between the fusion protein partner and the protein sequence of the present invention so as to allow removal of the latter. Preferably the fusion protein partner will not hinder the function of the protein of the present invention.

Polynucleotide Variants and Derivatives

The terms "variant" or "derivative" in relation to the nucleotide sequence of the present invention include any substitution of, variation of, modification of, replacement of, deletion of or addition of one (or more) nucleic acid from or to the sequence providing the resultant nucleotide sequence codes for a polypeptide having human SEP activity, preferably having at least the same activity as the polypeptide encoded by the sequence presented in SEQ ID NO: 1 or SEQ ID NO: 5.

As indicated above, with respect to sequence homology, preferably there is at least 83%, more preferably at least 85%, more preferably at least 90% homology to the sequence shown in SEQ ID NO: 1 or SEQ ID NO: 5. More preferably there is at least 95%, more preferably at least 98%, homology. Nucleotide homology comparisons may be conducted as described above. For some applications, a preferred sequence comparison program is the GCG Wisconsin Bestfit program described above. The default scoring matrix has a match value of 10 for each identical nucleotide and −9 for each mismatch. The default gap creation penalty is −50 and the default gap extension penalty is −3 for each nucleotide.

As used herein, the terms "variant", "homologue", "fragment" and "derivative" embrace allelic variations of the sequences.

The term "variant" also encompasses sequences that are complementary to sequences that are capable of hydridising to the nucleotide sequences presented herein.

Hybridisation

The term "hybridisation" as used herein shall include "the process by which a strand of nucleic acid joins with a complementary strand through base pairing" (Coombs J (1994) Dictionary of Biotechnology, Stockton Press, New York N.Y.) as well as the process of amplification as carried out in PCR technologies as described in Dieffenbach C W and G S Dveksler (1995, PCR Primer, a Laboratory Manual, Cold Spring Harbor Press, Plainview, N.Y., USA).

Hybridisation conditions are based on the melting temperature (Tm) of the nucleic acid binding complex, as taught in Berger and Kimmel (1987, Guide to Molecular Cloning Techniques, Methods in Enzymology, Vol 152, Academic Press, San Diego, Calif., USA), and confer a defined "stringency" as explained below.

Stringency of hybridisation refers to conditions under which polynucleic acids hybrids are stable. Such conditions are evident to those of ordinary skill in the field. As known to those of skill in the art, the stability of hybrids is reflected in the melting temperature (Tm) of the hybrid which decreases approximately 1 to 1.5° C. with every 1% decrease in sequence homology. In general, the stability of a hybrid is a function of sodium ion concentration and temperature. Typically, the hybridisation reaction is performed under conditions of higher stringency, followed by washes of varying stringency.

As used herein, high stringency refers to conditions that permit hybridisation of only those nucleic acid sequences that form stable hybrids in 1 M Na$^+$ at 65–68° C.

Maximum stringency typically occurs at about Tm-5° C. (5° C. below the Tm of the probe).

High stringency occurs at about 5° C. to 10° C. below the Tm of the probe. High stringency conditions can be provided, for example, by hybridisation in an aqueous solution containing 6xSSC, 5xDenhardt's, 1% SDS (sodium dodecyl sulphate), 0.1 Na$^+$ pyrophosphate and 0.1 mg/ml denatured salmon sperm DNA as non specific competitor. Following hybridisation, high stringency washing may be done in several steps, with a final wash (about 30 min) at the hybridisation temperature in 0.2–0.1xSSC, 0.1% SDS.

Moderate, or intermediate, stringency typically occurs at about 10° C. to 20° C. below the Tm of the probe.

Low stringency typically occurs at about 20° C. to 25° C. below the Tm of the probe.

As will be understood by those of skill in the art, a maximum stringency hybridisation can be used to identify or detect identical polynucleotide sequences while an intermediate (or low) stringency hybridisation can be used to identify or detect similar or related polynucleotide sequences.

Moderate stringency refers to conditions equivalent to hybridisation in the above-described solution but at about 60–62° C. In that case the final wash is performed at the hybridisation temperature in 1×SSC, 0.1% SDS.

Low stringency refers to conditions equivalent to hybridisation in the above-described solution at about 50–52° C. In that case, the final wash is performed at the hybridisation temperature in 2×SSC, 0.1% SDS.

It is understood that these conditions may be adapted and duplicated using a variety of buffers, e.g. formamide-based buffers, and temperatures. Denhardt's solution and SSC are well known to those of skill in the art as are other suitable hybridisation buffers (see, e.g., Sambrook, et al., eds. (1989) Molecular Cloning: A Laboratory Manual, Cold Spring Harbor Laboratory Press, New York; or Ausubel, et al., eds. (1990) Current Protocols in Molecular Biology, John Wiley & Sons, Inc.). Optimal hybridisation conditions have to be determined empirically, as the length and the GC content of the probe also play a role.

Polynucleotides of the invention capable of selectively hybridising to the nucleotide sequences presented herein, or to their complement, will be generally at least 83%, preferably at least 85% or 90% and more preferably at least 95% or 98% homologous to the corresponding nucleotide sequences presented herein over a region of at least 20, preferably at least 25 or 30, for instance at least 40, 60 or 100 or more contiguous nucleotides.

The term "selectively hybridisable" means that the polynucleotide used as a probe is used under conditions where a target polynucleotide of the invention is found to hybridize to the probe at a level significantly above background. The background hybridization may occur because of other polynucleotides present, for example, in the cDNA or genomic DNA library being screened. In this event, background implies a level of signal generated by interaction between the probe and a non-specific DNA member of the library which is less than 10-fold, preferably less than 100-fold as intense as the specific interaction observed with the target DNA. The intensity of interaction may be measured, for example, by radiolabelling the probe, e.g. with $^{32}P$.

In a preferred aspect, the present invention covers nucleotide sequences that can hybridise to any one or more of the nucleotide sequences of the present invention under stringent conditions (e.g. 65° C. and 0.1×SSC {1×SSC=0.15 M NaCl, 0.015 M $Na_3$ Citrate pH 7.0}).

Where the polynucleotide of the present invention is double-stranded, both strands of the duplex, either individually or in combination, are encompassed by the present invention. Where the polynucleotide is single-stranded, it is to be understood that the complementary sequence of that polynucleotide is also included within the scope of the present invention.

Polynucleotides which are not 100% homologous to the sequences of the present invention but fall within the scope of the invention can be obtained in a number of ways. Other variants of the sequences described herein may be obtained, for example, by probing DNA libraries made from a range of individuals, for example individuals from different populations. In addition, other viral/bacterial, or cellular homologues particularly cellular homologues found in mammalian cells (e.g. bovine, ovine, porcine, equine and primate cells), may be obtained and such homologues and fragments thereof in general will be capable of selectively hybridising to the sequence shown in SEQ ID NO: 1 or SEQ ID NO: 5. Such sequences may be obtained by probing cDNA libraries made from, or genomic DNA libraries derived from, other animal species, and probing such libraries with probes comprising all or part of the sequence shown in SEQ ID NO: 1 or SEQ ID NO: 5 under conditions of medium to high stringency. Similar considerations apply to obtaining species homologues and allelic variants of the polypeptide or nucleotide sequences of the invention.

Variants and strain/species homologues may also be obtained using degenerate PCR which will use primers designed to target sequences within the variants and homologues encoding conserved amino acid sequences within the sequences of the present invention. Conserved sequences can be predicted, for example, by aligning the amino acid sequences from several variants/homologues. Sequence alignments can be performed using computer software known in the art. For example the GCG Wisconsin PileUp program is widely used.

The primers used in degenerate PCR will contain one or more degenerate positions and will be used at stringency conditions lower than those used for cloning sequences with single sequence primers against known sequences.

Alternatively, such polynucleotides may be obtained by site-directed mutagenesis of characterised sequences. This may be useful where, for example, silent codon changes are required to sequences to optimise codon preferences for a particular host cell in which the polynucleotide sequences are being expressed. Other sequence changes may be desired in order to introduce restriction enzyme recognition sites, or to alter the property or function of the polypeptides encoded by the polynucleotides.

Polynucleotides of the invention may be used to produce a primer, e.g. a PCR primer, a primer for an alternative amplification reaction, a probe e.g. labelled with a revealing label by conventional means using radioactive or non-radioactive labels, or the polynucleotides may be cloned into vectors. Such primers, probes and other fragments will be at least 15, preferably at least 20, for example at least 25, 30 or 40 nucleotides in length, and are also encompassed by the term polynucleotides of the invention as used herein.

Polynucleotides such as a DNA polynucleotides and probes according to the invention may be produced recombinantly, synthetically, or by any means available to those of skill in the art. They may also be cloned by standard techniques.

In general, primers will be produced by synthetic means, involving a step wise manufacture of the desired nucleic acid sequence one nucleotide at a time. Techniques for accomplishing this using automated techniques are readily available in the art. Longer polynucleotides will generally be produced using recombinant means, for example using a PCR cloning techniques. This will involve making a pair of primers (e.g. of about 15 to 30 nucleotides) flanking a region of the sequence which it is desired to clone, bringing the primers into contact with mRNA or cDNA obtained from an animal or human cell, performing a polymerase chain reaction under conditions which bring about amplification of the desired region, isolating the amplified fragment (e.g. by purifying the reaction mixture on an agarose gel) and recovering the amplified DNA. The primers may be designed to contain suitable restriction enzyme recognition sites so that the amplified DNA can be cloned into a suitable cloning vector.

Regulatory Sequences

Preferably, the polynucleotide of the present invention is operably linked to a regulatory sequence which is capable of providing for the expression of the coding sequence, such as by the chosen host cell. By way of example, the present invention covers a vector comprising the polynucleotide of the present invention operably linked to such a regulatory sequence, i.e. the vector is an expression vector.

The term "operably linked" refers to a juxtaposition wherein the components described are in a relationship permitting them to function in their intended manner. A regulatory sequence "operably linked" to a coding sequence is ligated in such a way that expression of the coding sequence is achieved under condition compatible with the control sequences.

The term "regulatory sequences" includes promoters and enhancers and other expression regulation signals.

The term "promoter" is used in the normal sense of the art, e.g. an RNA polymerase binding site.

Enhanced expression of the polynucleotide encoding the polypeptide of the present invention may also be achieved by the selection of heterologous regulatory regions, e.g. promoter, secretion leader and terminator regions, which serve to increase expression and, if desired, secretion levels of the protein of interest from the chosen expression host and/or to provide for the inducible control of the expression of the polypeptide of the present invention.

Preferably, the nucleotide sequence of the present invention may be operably linked to at least a promoter.

Aside from the promoter native to the gene encoding the polypeptide of the present invention, other promoters may be used to direct expression of the polypeptide of the present invention. The promoter may be selected for its efficiency in directing the expression of the polypeptide of the present invention in the desired expression host.

In another embodiment, a constitutive promoter may be selected to direct the expression of the desired polypeptide of the present invention. Such an expression construct may provide additional advantages since it circumvents the need to culture the expression hosts on a medium containing an inducing substrate.

Examples of strong constitutive and/or inducible promoters which are preferred for use in fungal expression hosts are those which are obtainable from the fungal genes for xylanase (xlnA), phytase, ATP-synthetase, subunit 9 (oliC), triose phosphate isomerase (tpi), alcohol dehydrogenase (AdhA), α-amylase (amy), amyloglucosidase (AG—from the glaA gene), acetamidase (amdS) and glyceraldehyde-3-phosphate dehydrogenase (gpd) promoters.

Examples of strong yeast promoters are those obtainable from the genes for alcohol dehydrogenase, lactase, 3-phosphoglycerate kinase and triosephosphate isomerase.

Examples of strong bacterial promoters are the α-amylase and SP02 promoters as well as promoters from extracellular protease genes.

Hybrid promoters may also be used to improve inducible regulation of the expression construct.

The promoter can additionally include features to ensure or to increase expression in a suitable host. For example, the features can be conserved regions such as a Pribnow Box or a TATA box. The promoter may even contain other sequences to affect (such as to maintain, enhance, decrease) the levels of expression of the nucleotide sequence of the present invention. For example, suitable other sequences include the Sh1-intron or an ADH intron. Other sequences include inducible elements—such as temperature, chemical, light or stress inducible elements. Also, suitable elements to enhance transcription or translation may be present. An example of the latter element is the TMV 5' signal sequence (see Sleat, Gene, 217, [1987], pp. 217–225; and Dawson, Plant Mol. Biol., 23, [1993], p. 97).

Secretion

The human SEP of the present invention is naturally secreted from source cells, e.g. in the testis. However, it is possible that mutation of the polynucleotide sequence encoding human SEP or alterations in, or absence of, post-translational modifications within cells expressing human SEP could lead to non-extracellular secretion of human SEP (e.g. intracellular deposition). In such cases, it is desirable for the polypeptide of the present invention to be secreted from the expression host into the culture medium from where the polypeptide of the present invention may be more easily recovered. According to the present invention, a secretion leader sequence may be selected on the basis of the desired expression host. Hybrid signal sequences may also be used with the context of the present invention.

Typical examples of heterologous secretion leader sequences are those originating from the fungal amyloglucosidase (AG) gene (glaA—both 18 and 24 amino acid versions e.g. from *Aspergillus*), the a-factor gene (yeasts e.g. *Saccharomyces* and *Kluyveromyces*) or the α-amylase gene (*Bacillus*).

Constructs

The term "construct"—which is synonymous with terms such as "conjugate", "cassette" and "hybrid"—includes the nucleotide sequence according to the present invention directly or indirectly attached to a promoter. An example of an indirect attachment is the provision of a suitable spacer group such as an intron sequence, such as the Sh1-intron or the ADH intron, intermediate the promoter and the nucleotide sequence of the present invention. The same is true for the term "fused" in relation to the present invention which includes direct or indirect attachment. In each case, the terms do not cover the natural combination of the nucleotide sequence coding for the protein ordinarily associated with the wild type gene promoter and when they are both in their natural environment.

The construct may even contain or express a marker which allows for the selection of the genetic construct in, for example, a bacterium, preferably of the genus *Bacillus*, such as *Bacillus subtilis*, or plants into which it has been transferred. Various markers exist which may be used, such as, for example, those encoding mannose-6-phosphate isomerase (especially for plants) or those markers that provide for antibiotic resistance—e.g. resistance to G418, hygromycin, bleomycin, kanamycin and gentamycin.

Preferably the construct of the present invention comprises at least the nucleotide sequence of the present invention operably linked to a promoter.

Vectors

The term "vector" includes expression vectors and transformation vectors and shuttle vectors.

The term "expression vector" means a construct capable of in vivo or in vitro expression.

The term "transformation vector" means a construct capable of being transferred from one entity to another entity—which may be of the same species or may be of a different species. If the construct is capable of being transferred from one species to another—such as from an *E. coli* plasmid to a bacterium, such as of the genus *Bacillus*, then the transformation vector is sometimes called a "shuttle vector". It may even be a construct capable of being transferred from an *E. coli* plasmid to an *Agrobacterium* to a plant.

The vectors of the present invention may be transformed into a suitable host cell as described below to provide for expression of a polypeptide of the present invention. Thus, in a further aspect the invention provides a process for preparing polypeptides according to the present invention which comprises cultivating a host cell transformed or transfected with an expression vector as described above under conditions to provide for expression by the vector of a coding sequence encoding the polypeptides, and recovering the expressed polypeptides.

The vectors may be, for example, plasmid, virus or bacteriophage (phage) vectors provided with an origin of replication, optionally a promoter for the expression of the polynucleotide and optionally a regulator of the promoter.

The vectors of the present invention may contain one or more selectable marker genes. The most suitable selection systems for industrial micro-organisms are those formed by the group of selection markers which do not require a mutation in the host organism. Examples of fungal selection markers are the genes for acetamidase (amdS), ATP synthetase, subunit 9 (oliC), orotidine-5'-phosphate-decarboxylase (pvrA), phleomycin and benomyl resistance (benA). Examples of non-fungal selection markers are the bacterial G418 resistance gene (this may also be used in yeast, but not in filamentous fungi), the ampicillin resistance gene (*E. coli*), the neomycin resistance gene (*Bacillus*) and the *E. coli* uidA gene, coding for β-glucuronidase (GUS).

Vectors may be used in vitro, for example for the production of RNA or used to transfect or transform a host cell.

Thus, polynucleotides of the present invention can be incorporated into a recombinant vector (typically a replicable vector), for example a cloning or expression vector. The vector may be used to replicate the nucleic acid in a compatible host cell. Thus, in a further embodiment, the invention provides a method of making polynucleotides of the present invention by introducing a polynucleotide of the present invention into a replicable vector, introducing the vector into a compatible host cell, and growing the host cell under conditions which bring about replication of the vector. The vector may be recovered from the host cell. Suitable host cells are described below in connection with expression vectors.

The present invention also relates to the use of genetically engineered host cells expressing a human SEP or variant, homologue, fragment or derivative thereof in screening methods for the identification of modulators (e.g. inhibitors) of human SEP. Such genetically engineered host cells could be used to screen peptide libraries or organic molecules capable of modulating human SEP activity. Inhibitors of human SEP, such as antibodies, peptides or small organic molecules will provide the basis for pharmaceutical compositions for the prophylaxis and/or treatment of diseases associated with, for example, human SEP. Such inhibitors can be administered alone or in combination with other therapeutics for the prophylaxis and/or treatment of such diseases.

The present invention also relates to expression vectors and host cells comprising polynucleotide sequences encoding human SEP or a variant, homologue, fragment or derivative thereof for the in vivo or in vitro production of human SEP protein or to screen for agents that can affect human SEP expression or activity.

Tissue

The term "tissue" as used herein includes tissue per se and organ.

Host Cells

The term "host cell"—in relation to the present invention—includes any cell that could comprise the nucleotide sequence coding for the recombinant protein according to the present invention and/or products obtained therefrom, wherein a promoter can allow expression of the nucleotide sequence according to the present invention when present in the host cell.

Thus, a further embodiment of the present invention provides host cells transformed or transfected with a polynucleotide of the present invention. Preferably said polynucleotide is carried in a vector for the replication and expression of said polynucleotide. The cells will be chosen to be compatible with the said vector and may, for example, be prokaryotic (for example, bacterial cells), or eukaryotic (i.e. mammalian, fungal, insect, protozoan, yeast or plant cells).

The gram-negative bacterium *E. coli* is widely used as a host for heterologous gene expression. However, large amounts of heterologous protein tend to accumulate inside the cell. Subsequent purification of the desired protein from the bulk of *E. coli* intracellular proteins can sometimes be difficult.

In contrast to *E. coli*, bacteria from the genus *Bacillus* are very suitable as heterologous hosts because of their capability to secrete proteins into the culture medium. Other bacteria suitable as hosts are those from the genera *Streptomyces* and *Pseudomonas*.

Introduction of polynucleotides into host cells can be effected by methods as described in Sambrook, et al., eds. (1989) Molecular Cloning: A Laboratory Manual, Cold Spring Harbor Laboratory Press, New York, N.Y., USA. These methods include, but are not limited to, calcium phosphate transfection, DEAE-dextran-mediated transfection, cationic lipid-mediated transfection, electroporation, transvection, microinjection, transduction, scrape loading, and ballistic introduction.

Examples of representative hosts include, bacterial cells (e.g. *E. coli, Steptomyces*); fungal cells such as yeast cells and *Aspergillus*; insect cells such as *Drosophila* S2 and *Spodoptera* SF9 cells; animal cells such as CHO, COS, HEK, HeLa, and 3T3 cells. The selection of the appropriate host is deemed to be within the scope of those skilled in the art.

Depending on the nature of the polynucleotide encoding the polypeptide of the present invention, and/or the desirability for further processing of the expressed protein, eukaryotic hosts such as yeasts or other fungi may be preferred. In general, yeast cells are preferred over fungal cells because they are easier to manipulate. However, some proteins are either poorly expressed or secreted from the yeast cell, or in some cases are not processed properly (e.g. hyperglycosylation in yeast). In these instances, a different fungal host organism should be selected.

Examples of suitable expression hosts within the scope of the present invention are fungi such as *Aspergillus* species (such as those described in EP-A-0184438 and EP-A-0284603) and *Trichoderma* species; bacteria such as *Escherichia* species or *Bacillus* species (such as those described in EP-A-0134048 and EP-A-0253455), *Streptomyces* species and *Pseudomonas* species; and yeasts such as *Kluyveromyces* species (such as those described in EP-A-0096430 and EP-A-0301670) and *Saccharomyces* species. By way of example, typical expression hosts may be selected from *Aspergillus niger, Aspergillus niger* var. *tubigenis, Aspergillus niger* var. *awamori, Aspergillus aculeatis, Aspergillus nidulans, Aspergillus orvzae, Trichoderma reesei, Kluyveromyces lactis, Bacillus subtilis, Bacillus licheniformis, Bacillus amyloliquefaciens, Schizosaccharomyces pombe, Pichia pastoris* and *Saccharomyces cerevisiae.*

The use of suitable host cells—such as mammalian, yeast, insect, plant and fungal host cells—may provide for post-translational modifications (e.g. myristoylation, glycosylation, truncation, lapidation and tyrosine, serine or threonine phosphorylation) as may be needed to confer optimal biological activity on recombinant expression products of the present invention.

Organism

The term "organism" in relation to the present invention includes any organism, except man, that could comprise the nucleotide sequence coding for the recombinant protein according to the present invention and/or products obtained therefrom, wherein a promoter can allow expression of the nucleotide sequence according to the present invention when present in the organism. Examples of organisms may include a fungus, yeast, plant or protozoan.

The term "transgenic organism" in relation to the present invention includes any organism, except man, that comprises the nucleotide sequence coding for the protein according to the present invention and/or products obtained therefrom, wherein the promoter can allow expression of the nucleotide sequence according to the present invention within the organism. Preferably the nucleotide sequence is incorporated in the genome of the organism.

The term "transgenic organism" does not cover the native nucleotide coding sequence according to the present invention in its natural environment when it is under the control of its native promoter which is also in its natural environment. In addition, the present invention does not cover the native protein according to the present invention when it is in its natural environment and when it has been expressed by its native nucleotide coding sequence which is also in its natural environment and when that nucleotide sequence is under the control of its native promoter which is also in its natural environment.

Therefore, the transgenic organism of the present invention includes an organism comprising any one of, or combinations of, the nucleotide sequence coding for the amino acid sequence according to the present invention, constructs according to the present invention (including combinations thereof), vectors according to the present invention, plasmids according to the present invention, cells according to the present invention, and tissues according to the present invention or the products thereof. The transformed cell or organism could prepare acceptable quantities of the desired compound which would be easily retrievable from the cell or organism.

Transformation of Host Cells/Host Organisms

As indicated earlier, the host organism can be a prokaryotic or a eukaryotic organism. Examples of suitable prokaryotic hosts include *E. coli* and *Bacillus subtilis*. Teachings on the transformation of prokaryotic hosts are well documented in the art, for example see Sambrook et al. (Molecular Cloning: A Laboratory Manual, 2nd edition, 1989, Cold Spring Harbor Laboratory Press, New York, N.Y., USA) and Ausubel et al. (Current Protocols in Molecular Biology (1995), John Wiley & Sons, Inc.).

In one embodiment, the transformed host is a mammalian cell or, for example, an insect cell, wherein introduction of polynucleotides into said host cells can be effected by methods as described in, for example, Sambrook et al. (Molecular Cloning: A Laboratory Manual, 2nd edition, 1989, Cold Spring Harbor Laboratory Press, New York, N.Y., USA). These methods include, but are not limited to, calcium phosphate transfection, DEAE-dextran-mediated transfection, cationic lipid-mediated transfection, electroporation, transvection, microinjection, transduction, scrape loading, and ballistic introduction.

In another embodiment the transgenic organism can be a yeast. In this regard, yeast have also been widely used as a vehicle for heterologous gene expression. The species *Saccharomyces cerevisiae* has a long history of industrial use, including its use for heterologous gene expression. Expression of heterologous genes in *Saccharomyces cerevisiae* has been reviewed by Goodey et al. (1987, Yeast Biotechnology, D R Berry et al, eds, pp 401–429, Allen and Unwin, London) and by King et al. (1989, Molecular and Cell Biology of Yeasts, E F Walton and G T Yarronton, eds, pp 107–133, Blackie, Glasgow).

For several reasons *Saccharomyces cerevisiae* is well suited for heterologous gene expression. First, it is non-pathogenic to humans and it is incapable of producing certain endotoxins. Second, it has a long history of safe use following centuries of commercial exploitation for various purposes. This has led to wide public acceptability. Third, the extensive commercial use and research devoted to the organism has resulted in a wealth of knowledge about the genetics and physiology as well as large-scale fermentation characteristics of *Saccharomyces cerevisiae*.

A review of the principles of heterologous gene expression in *Saccharomyces cerevisiae* and secretion of gene products is given by E Hinchcliffe and E Kenny ("Yeast as a vehicle for the expression of heterologous genes", 1993, Yeasts, Vol 5, Anthony H Rose and J Stuart Harrison, eds, 2nd edition, Academic Press Ltd.).

Several types of yeast vectors are available, including integrative vectors, which require recombination with the host genome for their maintenance, and autonomously replicating plasmid vectors.

In order to prepare the transgenic *Saccharomyces*, expression constructs are prepared by inserting the nucleotide sequence of the present invention into a construct designed for expression in yeast. Several types of constructs used for heterologous expression have been developed. The constructs contain a promoter active in yeast fused to the nucleotide sequence of the present invention, usually a promoter of yeast origin, such as the GAL1 promoter, is used. Usually a signal sequence of yeast origin, such as the sequence encoding the SUC2 signal peptide, is used. A terminator active in yeast ends the expression system.

For the transformation of yeast several transformation protocols have been developed. For example, a transgenic *Saccharomyces* according to the present invention can be prepared by following the teachings of Hinnen et al. (1978, Proceedings of the National Academy of Sciences of the USA, 75: 1929); Beggs, J D (1978, Nature, London, 275:104); and Ito, H et al. (1983, J. Bacteriology 153:163–168).

The transformed yeast cells are selected using various selective markers. Among the markers used for transformation are a number of auxotrophic markers such as LEU2, HIS4 and TRP1, and dominant antibiotic resistance markers such as aminoglycoside antibiotic markers, e.g. G418.

Another host organism is a plant. The basic principle in the construction of genetically modified plants is to insert genetic information in the plant genome so as to obtain a stable maintenance of the inserted genetic material.

Several techniques exist for inserting the genetic information, the two main principles being direct introduction of the genetic information and introduction of the genetic information by use of a vector system. A review of the general techniques may be found in articles by Potrykus (Annu Rev Plant Physiol Plant Mol Biol [1991] 42:205–225) and Christou (Agro-Food-Industry Hi-Tech, March/April 1994, 17–27). Further teachings on plant transformation may be found in EP-A-0449375.

Thus, the present invention also provides a method of transforming a host cell with a nucleotide sequence shown in SEQ ID NO: 1 or SEQ ID NO: 5 or a derivative, homologue, variant or fragment thereof.

Host cells transformed with a human SEP nucleotide coding sequence may be cultured under conditions suitable for the expression and recovery of the encoded protein from cell culture. The protein produced by a recombinant cell may be secreted or may be contained intracellularly depending on the sequence and/or the vector used. As will be understood by those of skill in the art, expression vectors containing human SEP coding sequences can be designed with signal sequences which direct secretion of human SEP coding sequences through a particular prokaryotic or eukaryotic cell membrane (if the human SEP is not secreted in the absence of such signal sequences). Other recombinant constructions may join human SEP coding sequence to nucleotide sequence encoding a polypeptide domain which will facilitate purification of soluble proteins (Kroll D J et al (1993) DNA Cell Biol., Vol 12, pp. 441–53; see also above discussion of vectors containing fusion proteins).

Genetically Engineered or Genetically Modified

A cell, preferably an animal cell, that is "genetically modified" is heterozygous or homozygous for a modification that is introduced into the cell, or into a progenitor cell, by genetic engineering. The standard methods of genetic engineering that are available for introducing the modification include homologous recombination, viral vector gene trapping, irradiation, chemical mutagenesis, and the transgenic expression of a nucleotide sequence encoding antisense RNA alone or in combination with catalytic ribozymes. Preferred methods for genetic modification are homologous recombination and viral vector gene trapping which both modify an endogenous gene by inserting a foreign nucleic acid sequence into the gene locus. A nucleic acid sequence that is foreign to the gene is an exogenous sequence that is non-naturally occurring in the gene. This insertion of foreign DNA can occur within any region of the human SEP gene, e.g., in an enhancer, promoter, regulator region, non-coding region, coding region, intron, or exon. The most preferred method of genetic engineering is homologous recombination, in which the foreign nucleic acid sequence is inserted in a targeted manner either alone or in combination with a deletion of a portion of the endogenous gene sequence.

Functionally Disrupted

By a human SEP gene that is "functionally disrupted" is meant a human SEP gene that is genetically modified such that the cellular activity of the human SEP polypeptide encoded by the disrupted gene is decreased in cells that normally express the wild-type version of the human SEP gene. When the genetic modification effectively eliminates all wild-type copies of the human SEP gene in a cell (e.g., the genetically modified cell, preferably an animal cell, is homozygous for the human SEP gene disruption or the only wild-type copy of human SEP gene originally present is now disrupted), then the genetic modification results in a reduction in human SEP polypeptide activity as compared to an appropriate control cell that expresses the wild-type human SEP gene. This reduction in human SEP polypeptide activity results from either reduced human SEP gene expression (i.e., human SEP mRNA levels are effectively reduced and produce reduced levels of human SEP polypeptide) and/or because the disrupted human SEP gene encodes a mutated polypeptide with reduced function or stability as compared to a wild-type human SEP polypeptide. Preferably, the activity of human SEP polypeptide in the genetically modified cell is reduced to 50% or less of wild-type levels, more preferably, to 25% or less, and, even more preferably, to 10% or less of wild-type levels. Most preferably, the human SEP gene disruption results in a null mutation.

Genetically Modified Animal Cell

By a "genetically modified animal cell" containing a functionally disrupted human SEP gene is meant an animal cell, including a human cell, created by genetic engineering to contain a functionally disrupted human SEP gene, as well as daughter cells that inherit the disrupted human SEP gene. These cells may be genetically modified in culture according to any standard method known in the art. As an alternative to genetically modifying the cells in culture, non-human mammalian cells may also be isolated from a genetically modified, non-human mammal that contains a human SEP gene disruption. The animal cells of the invention may be obtained from primary cell or tissue preparations as well as culture-adapted, tumorigenic, or transformed cell lines. These cells and cell lines are derived, for example, from endothelial cells, epithelial cells, islets, neurons and other neural tissue-derived cells, mesothelial cells, osteocytes, lymphocytes, chondrocytes, hematopoietic cells, immune cells, cells of the major glands or organs (e.g., liver, lung, heart, stomach, pancreas, kidney, and skin), muscle cells (including cells from skeletal muscle, smooth muscle, and cardiac muscle), exocrine or endocrine cells, fibroblasts, and embryonic and other totipotent or pluripotent stem cells (e.g., embryonic stem (ES) cells, ES-like cells, and embryonic germline (EG) cells, and other stem cells, such as progenitor cells and tissue-derived stem cells). The preferred genetically modified cells are ES cells, more preferably, mouse or rat ES cells, and, most preferably, human ES cells.

A "homology region" used in a targeting vector for homologous recombination with a human SEP gene is related (i.e., complementary) to a portion of the human SEP gene or a sequence flanking the human SEP gene to a degree sufficient to allow hybridization to occur between the homology region and the human SEP gene sequence under standard low stringency conditions known in the art (e.g., as described in Current Protocols in Human Genetics, unit 4.1, John Wiley & Sons, New York, N.Y., 2000).

By an "ES cell" or an "ES-like cell" is meant a pluripotent stem cell derived from an embryo, from a primordial germ cell, or from a teratocarcinoma, that is capable of indefinite self renewal as well as differentiation into cell types that are representative of all three embryonic germ layers.

By "reduced" is meant a statistically significant decrease (i.e., $p<0.1$).

The genetically modified animal cells, including human cells, of the invention are heterozygous or homozygous for a modification that functionally disrupts the human SEP gene. The animal cells may be derived by genetically engineering cells in culture, or, in the case of non-human mammalian cells, the cells may be isolated from genetically modified, non-human mammals.

The human SEP gene locus is functionally disrupted by one of the several techniques for genetic modification known in the art, including chemical mutagenesis (Rinchik, Trends in Genetics 7: 15–21, 1991, Russell, Environmental & Molecular Mutagenesis 23 (Suppl. 24) 23–29, 1994), irradiation (Russell, supra), transgenic expression of human SEP gene antisense RNA, either alone or in combination with a catalytic RNA ribozyme sequence (Luyckx et al., Proc. Natl. Acad. Sci. 96: 12174–79, 1999; Sokol et al., Transgenic Research 5: 363–71, 1996; Efrat et al., Proc. Natl. Acad. Sci. USA 91: 2051–55, 1994; Larsson et al., Nucleic Acids Research 22: 2242–48, 1994) and, as further discussed below, the disruption of the human SEP gene by the insertion of a foreign nucleic acid sequence into the human SEP gene locus. Preferably, the foreign sequence is inserted by homologous recombination or by the insertion of a viral vector. Most preferably, the method of human SEP gene disruption is homologous recombination and includes a deletion of a portion of the endogenous human SEP gene sequence.

The integration of the foreign sequence functionally disrupts the human SEP gene through one or more of the following mechanisms: by interfering with the human SEP gene transcription or translation process (e.g., by interfering with promoter recognition, or by introducing a transcription termination site or a translational stop codon into the human SEP gene); or by distorting the human SEP gene coding sequence such that it no longer encodes a human SEP polypeptide with normal enzyme function (e.g., by inserting a foreign coding sequence into the human SEP gene coding sequence, by introducing a frameshift mutation or amino acid(s) substitution, or, in the case of a double crossover event, by deleting a portion of the human SEP gene coding sequence that is required for expression of a functional enzyme).

To insert a foreign sequence into a human SEP gene locus in the genome of a cell, the foreign DNA sequence is introduced into the cell according to a standard method known in the art such as electroporation, calcium-phosphate precipitation, retroviral infection, microinjection, biolistics, liposome transfection, DEAE-dextran transfection, or transferrinfection (see, e.g., Neumann et al., EMBO J. 1: 841–845, 1982; Potter et al., Proc. Natl. Acad. Sci USA 81: 7161–65, 1984; Chu et al., Nucleic Acids Res. 15: 1311–26, 1987; Thomas and Capecchi, Cell 51: 503–12, 1987; Baum et al., Biotechniques 17: 1058–62, 1994; Biewenga et al., J. Neuroscience Methods 71: 67–75, 1997; Zhang et al., Biotechniques 15: 868–72, 1993; Ray and Gage, Biotechniques 13: 598–603, 1992; Lo, Mol. Cell. Biol. 3: 1803–14, 1983; Nickoloff et al., Mol. Biotech. 10: 93–101, 1998; Linney et al., Dev. Biol. (Orlando) 213: 207–16, 1999; Zimmer and Gruss, Nature 338: 150–153, 1989; and Robertson et al., Nature 323: 445–48, 1986). The preferred method for introducing foreign DNA into a cell is electroporation.

Homologous Recombination

The method of homologous recombination targets the human SEP gene for disruption by introducing a human SEP gene targeting vector into a cell containing a human SEP gene. The ability of the vector to target the human SEP gene for disruption stems from using a nucleotide sequence in the vector that is homologous to the human SEP gene. This homology region facilitates hybridization between the vector and the endogenous sequence of the human SEP gene. Upon hybridization, the probability of a crossover event between the targeting vector and genomic sequences greatly increases. This crossover event results in the integration of the vector sequence into the human SEP gene locus and the functional disruption of the human SEP gene.

General principles regarding the construction of vectors used for targeting are reviewed in Bradley et al. (Biotechnol. 10: 534, 1992). Two different exemplary types of vector can be used to insert DNA by homologous recombination: an insertion vector or a replacement vector. An insertion vector is circular DNA which contains a region of human SEP gene homology with a double stranded break. Following hybridization between the homology region and the endogenous human SEP gene, a single crossover event at the double stranded break results in the insertion of the entire vector sequence into the endogenous gene at the site of crossover.

The more preferred vector to use for homologous recombination is a replacement vector, which is colinear rather than circular. Replacement vector integration into the human SEP gene requires a double crossover event, i.e. crossing over at two sites of hybridization between the targeting vector and the human SEP gene. This double crossover event results in the integration of vector sequence that is sandwiched between the two sites of crossover into the human SEP gene and the deletion of the corresponding endogenous human SEP gene sequence that originally spanned between the two sites of crossover (see, e.g., Thomas and Capecchi et al., Cell 51: 503–12, 1987; Mansour et al., Nature 336: 348–52, 1988; Mansour et al., Proc. Natl. Acad. Sci. USA 87: 7688–7692, 1990; and Mansour, GATA 7: 219–227, 1990).

A region of homology in a targeting vector is generally at least 100 nucleotides in length. Most preferably, the homology region is at least 1–5 kilobases (Kb) in length. Although there is no demonstrated minimum length or minimum degree of relatedness required for a homology region, targeting efficiency for homologous recombination generally corresponds with the length and the degree of relatedness between the targeting vector and the human SEP gene locus. In the case where a replacement vector is used, and a portion of the endogenous human SEP gene is deleted upon homologous recombination, an additional consideration is the size of the deleted portion of the endogenous human SEP gene. If this portion of the endogenous human SEP gene is greater than 1 Kb in length, then a targeting cassette with regions of homology that are longer than 1 Kb is recommended to enhance the efficiency of recombination. Further guidance regarding the selection and use of sequences effective for homologous recombination is described in the literature (see, e.g., Deng and Capecchi, Mol. Cell. Biol. 12: 3365–3371, 1992; Bollag et al., Annu. Rev. Genet. 23: 199–225, 1989; and Waldman and Liskay, Mol. Cell. Biol. 8: 5350–5357, 1988).

A wide variety of cloning vectors may be used as vector backbones in the construction of human SEP gene targeting vectors, including pBluescript-related plasmids (e.g., Bluescript KS+11), pQE70, pQE60, pQE-9, pBS, pD10, phagescript, phiX174, pBK Phagemid, pNH8A, pNH16a, pNH18Z, pNH46A, ptrc99a, pKK223-3, pKK233-3, pDR540, and pRIT5 PWLNEO, pSV2CAT, pXT1, pSG (Stratagene), pSVK3, PBPV, PMSG, and pSVL, pBR322 and pBR322-based vectors, pBM9, pBR325, pKH47, pBR328, pHC79, phage Charon 28, pKB11, pKSV-10, pK19 related plasmids, pUC plasmids, and the pGEM series of plasmids. These vectors are available from a variety of commercial sources (e.g., Boehringer Mannheim Biochemicals, Indianapolis, Ind.; Qiagen, Valencia, Calif.; Stratagene, La Jolla, Calif.; Promega, Madison, Wis.; and New England Biolabs, Beverly, Mass.; all in USA). However, any other vectors, e.g. plasmids, viruses, or parts thereof, may be used as long as they are replicable and viable in the desired host. The vector may also comprise sequences which enable it to replicate in the host whose genome is to be modified. The use of such a vector can expand the interaction period during which recombination can occur, increasing the efficiency of targeting (see Molecular Biology, ed. Ausubel et al, Unit 9.16, FIG. 9.16.1).

The specific host employed for propagating the targeting vectors described above is not critical. Examples include *E. coli* K12 RR1 (Bolivar et al., Gene 2: 95, 1977), *E. coli* K12 HB101 (ATCC No. 33694), *E. coli* MM21 (ATCC No. 336780), *E. coli* DH1 (ATCC No. 33849), *E. coli* strain DH5a, and *E. coli* STBL2. Alternatively, hosts such as *C.*

*cerevisiae* can be used. The above-mentioned hosts are available commercially (e.g., Stratagene, La Jolla, Calif., USA; and Life Technologies, Rockville, Md., USA).

To create the targeting vector, a human SEP gene targeting construct is added to an above-described vector backbone. The human SEP gene targeting constructs described above have at least one human SEP gene homology region. To make the human SEP gene homology regions, a human SEP gene-related sequence is used as a basis for producing polymerase chain reaction (PCR) primers. These primers are used to amplify the desired region of the human SEP sequence by high fidelity PCR amplification (Mattila et al., Nucleic Acids Res. 19: 4967, 1991; Eckert and Kunkel 1: 17, 1991; and U.S. Pat. No. 4,683,202). The genomic sequence is obtained from a genomic clone library or from a preparation of genomic DNA, preferably from the animal species that is to be targeted for human SEP gene disruption.

Preferably, the targeting constructs described above also include an exogenous nucleotide sequence encoding a positive marker protein. The stable expression of a positive marker after vector integration confers an identifiable characteristic on the cell without compromising cell viability. Therefore, in the case of a replacement vector, the marker gene is positioned between two flanking homology regions so that it integrates into the human SEP gene following the double crossover event.

It is preferred that the positive marker protein is a selectable protein; the stable expression of such a protein in a cell confers a selectable phenotypic characteristic, i.e., the characteristic enhances the survival of the cell under otherwise lethal conditions. Thus, by imposing the selectable condition, one can isolate cells that stably express the positive selectable marker from other cells that have not successfully integrated the vector sequence on the basis of viability. Examples of positive selectable marker proteins (and their agents of selection) include Neo (G418 or kanomycin), Hyg (hygromycin), HisD (histidinol), Gpt (xanthine), Ble (bleomycin), and Hprt (hypoxanthine) (see, e.g., Capecchi and Thomas, U.S. Pat. No. 5,464,764, and Capecchi, Science 244: 1288–92, 1989). Other positive markers that may also be used as an alternative to a selectable marker include reporter proteins such as β-galactosidase, firefly luciferase, or green fluorescent protein (see, e.g., Current Protocols in Cytometry, Unit 9.5, and Current Protocols in Molecular Biology, Unit 9.6, John Wiley & Sons, New York, N.Y., 2000).

The above-described positive selection scheme does not distinguish between cells that have integrated the vector by targeted homologous recombination at the human SEP gene locus versus random, non-homologous integration of vector sequence into any chromosomal position. Therefore, when using a replacement vector for homologous recombination, it is also preferred to include a nucleotide sequence encoding a negative selectable marker protein. Expression of a negative selectable marker causes a cell expressing the marker to lose viability when exposed to a certain agent (i.e., the marker protein becomes lethal to the cell under certain selectable conditions). Examples of negative selectable markers (and their agents of lethality) include herpes simplex virus thymidine kinase (gancyclovir or 1,2-deoxy-2-fluoro-α-d-arabinofuransyl-5-iodouracil), Hprt (6-thioguanine or 6-thioxanthine), and diphtheria toxin, ricin toxin, and cytosine deaminase (5-fluorocytosine).

The nucleotide sequence encoding the negative selectable marker is positioned outside of the two homology regions of the replacement vector. Given this positioning, cells will only integrate and stably express the negative selectable marker if integration occurs by random, non-homologous recombination; homologous recombination between the human SEP gene and the two regions of homology in the targeting construct excludes the sequence encoding the negative selectable marker from integration. Thus, by imposing the negative condition, cells that have integrated the targeting vector by random, non-homologous recombination lose viability.

The above-described combination of positive and negative selectable markers is preferred because a series of positive and negative selection steps can be designed to more efficiently select only those cells that have undergone vector integration by homologous recombination, and, therefore, have a potentially disrupted human SEP gene. Further examples of positive-negative selection schemes, selectable markers, and targeting constructs are described, for example, in U.S. Pat. No. 5,464,764, WO 94/06908, and Valancius and Smithies, Mol. Cell. Biol. 11: 1402, 1991.

In order for a marker protein to be stably expressed upon vector integration, the targeting vector may be designed so that the marker coding sequence is operably linked to the endogenous human SEP gene promoter upon vector integration. Expression of the marker is then driven by the human SEP gene promoter in cells that normally express human SEP gene. Alternatively, each marker in the targeting construct of the vector may contain its own promoter that drives expression independent of the human SEP gene promoter. This latter scheme has the advantage of allowing for expression of markers in cells that do not typically express the human SEP gene (Smith and Berg, Cold Spring Harbor Symp. Quant. Biol. 49: 171, 1984; Sedivy and Sharp, Proc. Natl. Acad. Sci. (USA) 86: 227: 1989; Thomas and Capecehi, Cell 51: 503, 1987).

Exogenous promoters that can be used to drive marker gene expression include cell-specific or stage-specific promoters, constitutive promoters, and inducible or regulatable promoters. Non-limiting examples of these promoters include the herpes simplex thymidine kinase promoter, cytomegalovirus (CMV) promoter/enhancer, SV40 promoters, PGK promoter, PMC1-neo, metallothionein promoter, adenovirus late promoter, vaccinia virus 7.5K promoter, avian beta globin promoter, histone promoters (e.g., mouse histone H3-614), beta actin promoter, neuron-specific enolase, muscle actin promoter, and the cauliflower mosaic virus 35S promoter (see, generally, Sambrook et al., Molecular Cloning, Vols. I–III, Cold Spring Harbor Laboratory Press, Cold Spring Harbor, N.Y., 1989, and *Current Protocols in Molecular Biology*, John Wiley & Sons, New York, N.Y., 2000; Stratagene, La Jolla, Calif., USA).

To confirm whether cells have integrated the vector sequence into the targeted human SEP gene locus, primers or genomic probes that are specific for the desired vector integration event can be used in combination with PCR or Southern blot analysis to identify the presence of the desired vector integration into the human SEP gene locus (Erlich et al., Science 252: 1643–51, 1991; Zimmer and Gruss, Nature 338: 150, 1989; Mouellic et al., Proc. Natl. Acad. Sci. (USA) 87: 4712, 1990; and Shesely et al., Proc. Natl. Acad. Sci. (USA) 88: 4294, 1991).

Gene Trapping

Another method available for inserting a foreign nucleic acid sequence into the human SEP gene locus to functionally disrupt the human SEP gene is gene trapping. This method takes advantage of the cellular machinery present in all mammalian cells that splices exons into mRNA to insert a gene trap vector coding sequence into a gene in a random fashion. Once inserted, the gene trap vector creates a mutation that may functionally disrupt the trapped human SEP gene. In contrast to homologous recombination, this system for mutagenesis creates largely random mutations. Thus, to obtain a genetically modified cell that contains a functionally disrupted human SEP gene, cells containing this particular mutation must be identified and selected from a pool of cells that contain random mutations in a variety of genes.

Gene trapping systems and vectors have been described for use in genetically modifying murine cells and other cell types (see, e.g., Allen et al., Nature 333: 852–55, 1988; Bellen et al., Genes Dev. 3: 1288–1300, 1989; Bier et al., Genes Dev. 3: 1273–1287, 1989; Bonnerot et al., J. Virol. 66: 4982–91, 1992; Brenner et al., Proe. Nat. Acad. Sci. USA 86: 5517–21, 1989; Chang et al., Virology 193: 737–47, 1993; Friedrich and Soriano, Methods Enzymol. 225: 681–701, 1993; Friedrich and Soriano, Genes Dev. 5: 1513–23, 1991; Goff, Methods Enzymol. 152: 469–81, 1987; Gossler et al., Science 244: 463–65, 1989; Hope, Develop. 113: 399–408, 1991; Kerr et al., Cold Spring Harb. Symp. Quant. Biol. 2: 767–776, 1989; Reddy et al., J. Virol. 65: 1507–1515, 1991; Reddy et al., Proc. Natl. Acad. Sci. U.S.A. 89: 6721–25, 1992; Skarnes et al., Genes Dev. 6: 903–918, 1992; von Melchner and Ruley, J. Virol. 63: 3227–3233, 1989; and Yoshida et al., Transgen. Res. 4: 277–87, 1995).

Promoter trap (5' trap) vectors contain, in 5' to 3' order, a splice acceptor sequence followed by an exon, which is typically characterized by a translation initiation codon and open reading frame (ORF) and/or an internal ribosome entry site. In general, these promoter trap vectors do not contain promoters or operably linked splice donor sequences. Consequently, after integration into the cellular genome of the host cell, the promoter trap vector sequence intercepts the normal splicing of the upstream gene and acts as a terminal exon. Expression of the vector coding sequence is dependent upon the vector integrating into an intron of the disrupted gene in the proper reading frame. In such a case, the cellular splicing machinery splices exons from the trapped gene upstream of the vector coding sequence (Zambrowicz et al., WO 99/50426).

An alternative method for producing an effect similar to the above-described promoter trap vector is a vector that incorporates a nested set of stop codons present in, or otherwise engineered into, the region between the splice acceptor of the promoter trap vector and the translation initiation codon or polyadenylation sequence. The coding sequence can also be engineered to contain an independent ribosome entry site (IRES) so that the coding sequence will be expressed in a manner largely independent of the site of integration within the host cell genome. Typically, but not necessarily, an IRES is used in conjunction with a nested set of stop codons.

Another type of gene trapping scheme uses a 3' gene trap vector. This type of vector contains, in operative combination, a promoter region, which mediates expression of an adjoining coding sequence, the coding sequence, and a splice donor sequence that defines the 3' end of the coding sequence exon. After integration into a host cell genome, the transcript expressed by the vector promoter is spliced to a splice acceptor sequence from the trapped gene that is located downstream of the integrated gene trap vector sequence. Thus, the integration of the vector results in the expression of a fusion transcript comprising the coding sequence of the 3' gene trap cassette and any downstream cellular exons, including the terminal exon and its polyadenylation signal. When such vectors integrate into a gene, the cellular splicing machinery splices the vector coding sequence upstream of the 3' exons of the trapped gene. One advantage of such vectors is that the expression of the 3' gene trap vectors is driven by a promoter within the gene trap cassette and does not require integration into a gene that is normally expressed in the host cell (Zambrowicz et al., WO 99/50426). Examples of transcriptional promoters and enhancers that may be incorporated into the 3' gene trap vector include those discussed above with respect to targeting vectors.

The viral vector backbone used as the structural component for the promoter or 3' gene trap vector may be selected from a wide range of vectors that can be inserted into the genome of a target cell. Suitable backbone vectors include, but are not limited to, herpes simplex virus vectors, adenovirus vectors, adeno-associated virus vectors, retroviral vectors, lentiviral vectors, pseudorabies virus, alpha-herpes virus vectors, and the like. A thorough review of viral vectors, in particular, viral vectors suitable for modifying non-replicating cells and how to use such vectors in conjunction with the expression of an exogenous polynucleotide sequence, can be found in *Viral Vectors: Gene Therapy and Neuroscience Applications*, Eds. Caplitt and Loewy, Academic Press, San Diego, 1995.

Preferably, retroviral vectors are used for gene trapping. These vectors can be used in conjunction with retroviral packaging cell lines such as those described in U.S. Pat. No. 5,449,614. Where non-murine mammalian cells are used as target cells for genetic modification, amphotropic or pantropic packaging cell lines can be used to package suitable vectors (Ory et al., Proc. Natl. Acad. Sci., USA 93: 11400–11406, 1996). Representative retroviral vectors that can be adapted to create the presently described 3' gene trap vectors are described, for example, in U.S. Pat. No. 5,521, 076.

The gene trapping vectors may contain one or more of the positive marker genes discussed above with respect to targeting vectors used for homologous recombination. Similar to their use in targeting vectors, these positive markers are used in gene trapping vectors to identify and select cells that have integrated the vector into the cell genome. The marker gene may be engineered to contain an independent ribosome entry site (IRES) so that the marker will be expressed in a manner largely independent of the location in which the vector has integrated into the target cell genome.

Given that gene trap vectors will integrate into the genome of infected host cells in a fairly random manner, a genetically modified cell having a disrupted human SEP gene must be identified from a population of cells that have undergone random vector integration. Preferably, the genetic modifications in the population of cells are of sufficient randomness and frequency such that the population represents mutations in essentially every gene found in the cell's genome, making it likely that a cell with a disrupted human SEP gene will be identified from the population (see Zambrowicz et al., WO 99/50426; Sands et al., WO 98/14614).

Individual mutant cell lines containing a disrupted human SEP gene are identified in a population of mutated cells using, for example, reverse transcription and PCR (RT-PCR) to identify a mutation in a human SEP gene sequence. This process can be streamlined by pooling clones. For example, to find an individual clone containing a disrupted human SEP gene, RT-PCR is performed using one primer anchored in the gene trap vector and the other primer located in the human SEP gene sequence. A positive RT-PCR result indicates that the vector sequence is encoded in the human SEP gene transcript, indicating that human SEP gene has been disrupted by a gene trap integration event (see, e.g., Sands et al., WO 98/14614).

Temporal, Spatial, and Inducible Gene Disruptions

A functional disruption of the endogenous human SEP gene can occur at specific developmental or cell cycle stages (temporal disruption) or in specific cell types (spatial disruption). The human SEP gene disruption can also be inducible when certain conditions are present. A recombinase excision system, such as a Cre-Lox system, may be used to activate or inactivate the human SEP gene at a specific developmental stage, in a particular tissue or cell type, or under particular environmental conditions. Generally, methods utilizing Cre-Lox technology are carried out as described by Torres and Kuhn, *Laboratory Protocols for Conditional Gene Targeting*, Oxford University Press, 1997. Methodology similar to that described for the Cre-Lox system can also be employed utilizing the FLP-FRT system. Further guidance regarding the use of recombinase excision systems for conditionally disrupting genes by homologous recombination or viral insertion is provided, for example, in U.S. Pat. No. 5,626,159, U.S. Pat. No. 5,527,695, U.S. Pat. No. 5,434,066, WO 98/29533, Orban et al., Proc. Nat. Acad. Sci. USA 89: 6861–65, 1992; O'Gorman et al., Science 251: 1351–55, 1991; Sauer et al., Nucleic Acids Research 17: 147–61, 1989; Barinaga, Science 265: 26–28, 1994; and Akagi et al., Nucleic Acids Res. 25: 1766–73, 1997. More than one recombinase system can be used to genetically modify an animal cell.

When using homologous recombination to disrupt the human SEP gene in a temporal, spatial, or inducible fashion, using a recombinase system such as the Cre-Lox system, a portion of the human SEP gene coding region is replaced by a targeting construct comprising the human SEP gene coding region flanked by loxP sites. Animal cells carrying this genetic modification contain a functional, loxP-flanked human SEP gene. The temporal, spatial, or inducible aspect of the human SEP gene disruption is caused by the expression pattern of an additional transgene, a Cre recombinase transgene, that is expressed in the animal cell under the control of the desired spatially-regulated, temporally-regulated, or inducible promoter, respectively. A Cre recombinase targets the loxP sites for recombination. Therefore, when Cre expression is activated, the LoxP sites undergo recombination to excise the sandwiched human SEP gene coding sequence, resulting in a functional disruption of the human SEP gene (Rajewski et al., J. Clin. Invest. 98: 600–03, 1996; St.-Onge et al., Nucleic Acids Res. 24: 3875–77, 1996; Agah et al., J. Clin. Invest. 100: 169–79, 1997; Brocard et al., Proc. Natl. Acad. Sci. USA 94: 14559–63, 1997; Feil et al., Proc. Natl. Acad. Sci. USA 93: 10887–90, 1996; and Kühn et al., Science 269: 1427–29, 1995).

A cell containing both a Cre recombinase transgene and loxP-flanked human SEP gene can be generated through standard transgenic techniques. Further guidance regarding the use of recombinase systems specific promoters to temporally, spatially, or conditionally disrupt the human SEP gene is found, for example, in Sauer, Meth. Enz. 225: 890–900, 1993, Gu et al., Science 265: 103–06, 1994, Araki et al., J. Biochem. 122: 977–82, 1997, Dymecki, Proc. Natl. Acad. Sci. 93: 6191–96, 1996, and Meyers et al., Nature Genetics 18: 136–41, 1998.

An inducible disruption of the human SEP gene can also be achieved by using a tetracycline responsive binary system (Gossen and Bujard, Proc. Natl. Acad. Sci. USA 89: 5547–51, 1992). This system involves genetically modifying a cell to introduce a Tet promoter into the endogenous human SEP gene regulatory element and a transgene expressing a tetracycline-controllable repressor (TetR). In such a cell, the administration of tetracycline activates the TetR which, in turn, inhibits human SEP gene expression and, therefore, functionally disrupts the human SEP gene (St.-Onge et al., Nucleic Acids Res. 24: 3875–77, 1996, U.S. Pat. No. 5,922,927).

The above-described systems for temporal, spatial, and inducible disruptions of the human SEP gene can also be adopted when using gene trapping as the method of genetic modification as described, for example, in WO 98/29533.

Creating Genetically Modified Animal Cells

The above-described methods for genetic modification can be used to functionally disrupt a human SEP gene in virtually any type of somatic or stem cell derived from an animal. Genetically modified animal cells of the invention include, but are not limited to, mammalian cells, including human cells, and avian cells. These cells may be derived from genetically engineering any animal cell line, such as culture-adapted, tumorigenic, or transformed cell lines, or they may be isolated from a genetically modified, non-human mammal carrying the desired human SEP genetic modification.

The cells may be heterozygous or homozygous for the disrupted human SEP gene. To obtain cells that are homozygous for the human SEP gene disruption (human SEP–/–), direct, sequential targeting of both alleles can be performed. This process can be facilitated by recycling a positive selectable marker. According to this scheme the nucleotide sequence encoding the positive selectable marker is removed following the disruption of one allele using the Cre-Lox P system. Thus, the same vector can be used in a subsequent round of targeting to disrupt the second human SEP gene allele (Abuin and Bradley, Mol. Cell. Biol. 16: 1851–56, 1996; Sedivy et al., T.I.G. 15: 88–90, 1999; Cruz et al., Proc. Natl. Acad. Sci. (USA) 88: 7170–74, 1991; Mortensen et al., Proc. Natl. Acad. Sci. (USA) 88: 7036–40, 1991; te Riele et al., Nature (London) 348: 649–651, 1990).

An alternative strategy for obtaining ES cells that are human SEP–/– is the homogenotization of cells from a population of cells that is heterozygous for the human SEP gene disruption (human SEP+/–). The method uses a scheme in which human SEP+/– targeted clones that express a selectable drug resistance marker are selected against a very high drug concentration; this selection favours cells that express two copies of the sequence encoding the drug resistance marker and are, therefore, homozygous for the human SEP gene disruption (Mortensen et al., Mol. Cell. Biol. 12: 2391–95, 1992).

Following the genetic modification of the desired cell or cell line, the human SEP gene locus can be confirmed as the site of modification by PCR analysis according to standard PCR or Southern blotting methods known in the art (see, e.g., U.S. Pat. No. 4,683,202; and Erlich et al., Science 252: 1643, 1991). Further verification of the functional disruption of the human SEP gene may also be made if human SEP gene messenger RNA (mRNA) levels and/or human SEP polypeptide levels are reduced in cells that normally express the human SEP gene. Measures of human SEP gene mRNA levels may be obtained by using reverse transcriptase mediated polymerase chain reaction (RT-PCR), Northern blot analysis, or in situ hybridization. The quantification of human SEP polypeptide levels produced by the cells can be made, for example, by standard immunoassay methods known in the art. Such immunoassays include, but are not limited to, competitive and non-competitive assay systems using techniques such as radioimmunoassays, ELISA (enzyme-linked immunosorbent assay), "sandwich" immunoassays, immunoradiometric assays, gel diffusion precipitin reactions, immunodiffusion assays, in situ immunoassays (using colloidal gold, enzymatic, or radioisotope labels, for example), Western blots, 2-dimensional gel analysis, precipitation reactions, immunofluorescence assays, protein A assays, and immunoelectrophoresis assays.

Preferred genetically modified animal cells are embryonic stem (ES) cells and ES-like cells. These cells are derived from the preimplantation embryos and blastocysts of various species, such as mice (Evans et al., Nature 129:154–156, 1981; Martin, Proc. Natl. Acad. Sci., USA, 78: 7634–7638, 1981), pigs and sheep (Notanianni et al., J. Reprod. Fert. Suppl., 43: 255–260, 1991; Campbell et al., Nature 380: 64–68,1996) and primates, including humans (Thomson et al., U.S. Pat. No. 5,843,780, Thomson et al., Science 282: 1145–1147, 1995; and Thomson et al., Proc. Natl. Acad. Sci. USA 92: 7844–7848, 1995).

These types of cells are pluripotent. That is, under proper conditions, they differentiate into a wide variety of cell types derived from all three embryonic germ layers: ectoderm, mesoderm and endoderm. Depending upon the culture conditions, a sample of ES cells can be cultured indefinitely as stem cells, allowed to differentiate into a wide variety of different cell types within a single sample, or directed to differentiate into a specific cell type, such as macrophage-like cells, neuronal cells, cardiomyocytes, adipocytes, smooth muscle cells, endothelial cells, skeletal muscle cells, keratinocytes, and hematopoietic cells, such as eosinophils, mast cells, erythroid progenitor cells, or megakaryocytes. Directed differentiation is accomplished by including specific growth factors or matrix components in the culture conditions, as further described, for example, in Keller et al., Curr. Opin. Cell Biol. 7: 862–69, 1995, Li et al., Curr. Biol. 8: 971, 1998, Klug et al., J. Clin. Invest. 98: 216–24, 1996, Lieschke et al., Exp. Hematol. 23: 328–34, 1995, Yamane et al., Blood 90: 3516–23, 1997, and Hirashima et al., Blood 93: 1253–63, 1999.

The particular embryonic stem cell line that is used for genetic modification is not critical; exemplary murine ES cell lines include AB-1 (McMahon and Bradley, Cell 62:1073–85, 1990), E14 (Hooper et al., Nature 326: 292–95, 1987), D3 (Doetschman et al., J. Embryol. Exp. Morph. 87: 27–45, 1985), CCE (Robertson et al, Nature 323: 445–48, 1986), RW4 (Genome Systems, St. Louis, Mo.), and DBA/1lacJ (Roach et al., Exp. Cell Res. 221: 520–25, 1995).

Production of the Polypeptide

According to the present invention, the production of the polypeptide of the present invention can be effected by the culturing of, for example, microbial expression hosts, which have been transformed with one or more polynucleotides of the present invention, in a conventional nutrient fermentation medium. The selection of the appropriate medium may be based on the choice of expression hosts and/or based on the regulatory requirements of the expression construct. Such media are well-known to those skilled in the art. The medium may, if desired, contain additional components favouring the transformed expression hosts over other potentially contaminating micro-organisms.

Thus, the present invention also provides a method for producing a polypeptide having human SEP activity, the method comprising the steps of (a) transforming a host cell with a nucleotide sequence shown in SEQ ID NO: 1 or SEQ ID NO: 5 or a derivative, homologue, variant or fragment thereof; and (b) culturing the transformed host cell under conditions suitable for the expression of said polypeptide.

The present invention also relates to a method for producing a polypeptide having human SEP activity, the method comprising the steps of (a) culturing a host cell that has been transformed with a nucleotide sequence shown in SEQ ID NO: 1 or SEQ ID NO: 5 or a derivative, homologue, variant or fragment thereof under conditions suitable for the expression of said polypeptide; and (b) recovering said polypeptide from the host cell culture.

The present invention also relates to a method for producing a polypeptide having human SEP activity, the method comprising the steps of (a) transforming a host cell with a nucleotide sequence shown in SEQ ID NO: 1 or SEQ ID NO: 5 or a derivative, homologue, variant or fragment thereof; (b) culturing the transformed host cell under conditions suitable for the expression of said polypeptide; and (c) recovering said polypeptide from the host cell culture.

Ribozymes

Ribozymes are enzymatic RNA molecules capable of catalysing the specific cleavage of RNA. The mechanism of ribozyme action involves sequence specific hybridisation of the ribozyme molecule to complementary target RNA, followed by a endonucleolytic cleavage. Within the scope of the invention are engineered hammerhead motif ribozyme molecules that specifically and efficiently catalyse endonucleolytic cleavage of human SEP RNA sequences.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide sequence inoperable. The suitability of candidate targets may also be evaluated by testing accessibility to hybridisation with complementary oligonucleotides using ribonuclease protection assays.

Both antisense RNA and DNA molecules and ribozymes of the invention may be prepared by any method known in the art for the synthesis of RNA molecules. These include techniques for chemically synthesising oligonucleotides such as solid phase phosphoramidite chemical synthesis. Alternatively, RNA molecules may be generated by in vitro or in vivo transcription of DNA sequences encoding the antisense RNA molecule. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

Detection

The presence of the human SEP polynucleotide coding sequence can be detected by DNA-DNA or DNA-RNA hybridisation or amplification using probes, portions or fragments of the sequence presented in SEQ ID NO: 1 or SEQ ID NO: 5. Nucleic acid amplification-based assays involve the use of oligonucleotides or oligomers based on the human SEP coding sequence to detect transformants containing human SEP DNA or RNA. As used herein "oligonucleotides" or "oligomers" may refer to a nucleic acid sequence of at least about 10 nucleotides and as many as about 60 nucleotides, preferably about 15 to 30 nucleotides, and more preferably about 20–25 nucleotides which can be used as a probe or amplimer. Preferably, oligonucleotides are derived from the 3' region of the nucleotide sequence shown in SEQ ID NO: 1 or SEQ ID NO: 5.

A variety of protocols for detecting and measuring the expression of human SEP polypeptide, such as by using either polyclonal or monoclonal antibodies specific for the protein, are known in the art. Examples include enzyme-linked immunosorbent assay (ELISA), radioimmunoassay (RIA) and fluorescent activated cell sorting (FACS). A two-site, monoclonal-based immunoassay utilising monoclonal antibodies reactive to two non-interfering epitopes on human SEP polypeptides is preferred, but a competitive binding assay may be employed. These and other assays are described, among other places, in Hampton R et al. (1990, Serological Methods, A Laboratory Manual, APS Press, St Paul, Minn., USA) and Maddox DE et al. (1983, J. Exp. Med., 158:1211).

A wide variety of labels and conjugation techniques are known by those skilled in the art and can be used in various nucleic and amino acid assays. Means for producing labelled hybridisation or PCR probes for detecting human SEP polynucleotide sequences include oligolabelling, nick translation, end-labelling or PCR amplification using a labelled nucleotide. Alternatively, the human SEP coding sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labelled nucleotides.

A number of companies such as Pharmacia Biotech (Piscataway, N.J., USA), Promega (Madison, Wis., USA), and US Biochemical Corporation (Cleveland, Ohio, USA) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. No. 3,817,837; U.S. Pat. No. 3,850,752; U.S. Pat. No. 3,939,350; U.S. Pat. No. 3,996,345; U.S. Pat. No. 4,277,437; U.S. Pat. No. 4,275,149 and U.S. Pat. No. 4,366,241. Also, recombinant immunoglobulins may be produced as shown in U.S. Pat. No. 4,816,567.

Additional methods to quantify the expression of a particular molecule include radiolabelling (Melby P C et al., 1993, J. Immunol. Methods, Vol 159, pp. 235–244) or biotinylating (Duplaa C et al., 1993, Annal Biochem., Vol 229, p. 36) nucleotides, co-amplification of a control nucleic acid, and standard curves onto which the experimental results are interpolated. Quantification of multiple samples may be speeded up by running the assay in an ELISA format where the oligomer of interest is presented in various dilutions and a spectrophotometric or calorimetric response gives rapid quantification.

Although the presence/absence of marker gene expression suggests that the gene of interest is also present, its presence and expression should be confirmed. For example, if the human SEP coding sequence is inserted within a marker gene sequence, recombinant cells containing human SEP coding regions can be identified by the absence of marker gene function. Alternatively, a marker gene can be placed in tandem with a human SEP coding sequence under the control of a single promoter. Expression of the marker gene in response to induction or selection usually indicates expression of human SEP as well.

Alternatively, host cells which contain the coding sequence for human SEP and express human SEP coding regions may be identified by a variety of procedures known to those of skill in the art. These procedures include, but are not limited to, DNA-DNA or DNA-RNA hybridisation and protein bioassay or immunoassay techniques which include membrane-based, solution-based, or chip-based technologies for the detection and/or quantification of the nucleic acid or protein.

Antibodies

The amino acid sequence of the present invention can also be used to generate antibodies—such as by use of standard techniques—against the amino acid sequence.

Procedures well known in the art may be used for the production of antibodies to human SEP polypeptides. Such antibodies include, but are not limited to, polyclonal, monoclonal, chimeric, single chain, Fab fragments and fragments produced by a Fab expression library. Neutralising antibodies, i.e. those which inhibit biological activity of human SEP polypeptides, are especially preferred for diagnostics and therapeutics.

For the production of antibodies, various hosts including goats, rabbits, rats, mice, etc. may be immunised by injection with the inhibitor or any portion, variant, homologue, fragment or derivative thereof or oligopeptide which retains immunogenic properties. Depending on the host species, various adjuvants may be used to increase immunological response. Such adjuvants include, but are not limited to, Freund's, mineral gels such as aluminium hydroxide, and surface active substances such as lysolecithin, pluronic polyols, polyanions, peptides, oil emulsions, keyhole limpet hemocyanin, and dinitrophenol. BCG (Bacilli Calmette-Guerin) and *Corynebacterium parvum* are potentially useful human adjuvants which may be employed.

Monoclonal antibodies to the amino acid sequence may be even prepared using any technique which provides for the production of antibody molecules by continuous cell lines in culture. These include, but are not limited to, the hybridoma technique originally described by Köhler and Milstein (1975, Nature, Vol 256, pp. 495–497), the human B-cell hybridoma technique (Kosbor et al., (1983), Immunol. Today, Vol 4, p. 72; Cote et al., (1983), Proceedings of the National Academy of Sciences (USA), Vol 80, pp. 2026–2030) and the EBV-hybridoma technique (Cole et al., (1985), Monoclonal Antibodies and Cancer Therapy, Alan R Liss Inc., pp. 77–96). In addition, techniques developed for the production of "chimeric antibodies", the splicing of mouse antibody genes to human antibody genes to obtain a molecule with appropriate antigen specificity and biological activity can be used (Morrison et al., (1984), Proceedings of the National Academy of Sciences (USA), Vol 81, pp. 6851–6855; Neuberger et al., (1984), Nature, Vol 312, pp. 604–608; Takeda et al., (1985), Nature, Vol 314, pp. 452–454). Alternatively, techniques described for the production of single chain antibodies (U.S. Pat. No. 4,946,779) can be adapted to produce inhibitor-specific single chain antibodies.

Antibodies may also be produced by inducing in vivo production in the lymphocyte population or by screening recombinant immunoglobulin libraries or panels of highly specific binding reagents as disclosed in Orlandi et al. (1989, Proceedings of the National Academy of Sciences (USA), Vol 86, pp. 3833–3837), and Winter G and Milstein C (1991; Nature, Vol 349, pp. 293–299).

Antibody fragments which contain specific binding sites for human SEP may also be generated. For example, such fragments include, but are not limited to, the $F(ab')_2$ fragments which can be produced by pepsin digestion of the antibody molecule and the Fab fragments which can be generated by reducing the disulphide bridges of the $F(ab')_2$ fragments. Alternatively, Fab expression libraries may be constructed to allow rapid and easy identification of monoclonal Fab fragments with the desired specificity (Huse W D et al., (1989), Science, Vol 256, pp. 1275–1281).

An alternative technique involves screening phage display libraries where, for example, the phage express scFv fragments on the surface of their coat with a large variety of complementarity determining regions (CDRs). This technique is well known in the art.

Human SEP-specific antibodies are useful for the diagnosis of conditions and diseases associated with expression of human SEP polypeptide. A variety of protocols for competitive binding or immunoradiometric assays using either polyclonal or monoclonal antibodies with established specificities are well known in the art. Such immunoassays typically involve the formation of complexes between human SEP polypeptides and its specific antibody (or similar human SEP-binding molecule) and the measurement of complex formation. A two-site, monoclonal based immunoassay utilising monoclonal antibodies reactive to two non-interfering epitopes on a specific human SEP protein is preferred, but a competitive binding assay may also be employed. These assays are described in Maddox D E et al. (1983, Journal of Experimental Medicine, Vol 158, p. 1211).

Anti-human SEP antibodies are useful for the diagnosis of disorders involving abnormal peptide signalling or other disorders or diseases characterised by abnormal expression of a human SEP. Diagnostic assays for a human SEP include methods utilising the antibody and a label to detect a human SEP polypeptide in human body fluids, cells, tissues or sections or extracts of such tissues. The polypeptides and antibodies of the present invention may be used with or without modification. Frequently, the polypeptides and antibodies will be labelled by joining them, either covalently or noncovalently, with a reporter molecule. A wide variety of reporter molecules are known to those of skill in the art.

Antibodies may be used in method of detecting polypeptides of the invention present in biological samples by a method which comprises: (a) providing an antibody of the invention; (b) incubating a biological sample with said antibody under conditions which allow for the formation of an antibody-antigen complex; and (c) determining whether antibody-antigen complex comprising said antibody is formed.

Depending on the circumstances, suitable samples may include extract tissues such as testis or brain or from neoplastic growths derived from such tissues.

Antibodies of the invention may be bound to a solid support and/or packaged into kits in a suitable container along with suitable reagents, controls, instructions and the like.

Assays/Identification Methods

The present invention also relates to an assay method for detecting the presence of human SEP in cells (such as human cells) comprising: (a) performing a reverse transcriptase-polymerase chain reaction (RT-PCR) on RNA (such as total RNA) from such cells using a pair of PCR primers that are specific for human SEP, as determined from the DNA sequence shown in SEQ ID NO: 1 or SEQ ID NO: 5 or an allelic variation thereof; and (b) assaying the appearance of an appropriately sized PCR fragment—such as by agarose gel electrophoresis.

The present invention also relates to a method of identifying agents (such as compounds, other substances or compositions comprising the same) that affect (such as inhibit or otherwise modify) the activity of human SEP and/or the expression thereof, the method comprising contacting human SEP or the nucleotide sequence coding for the same with the agent and then measuring the activity of human SEP and/or the expression thereof.

The present invention also relates to a method of identifying agents (such as compounds, other substances or compositions comprising the same) that selectively affect (such as selectively inhibit or otherwise selectively modify) the activity of human SEP and/or the expression thereof, the method comprising contacting human SEP or the nucleotide sequence coding for the same with the agent and then measuring the activity of human SEP and/or the expression thereof.

The present invention also relates to a method of identifying agents (such as compounds, other substances or compositions comprising the same) that affect (such as inhibit or otherwise modify) the activity of human SEP and/or the expression thereof, the method comprising measuring the activity of human SEP and/or the expression thereof in the presence of the agent or after the addition of the agent in: (a) a cell line into which has been incorporated recombinant DNA comprising the DNA sequence shown in SEQ ID NO: 1 or SEQ ID NO: 5 or an allelic variation thereof, or (b) a cell population or cell line that naturally selectively expresses human SEP. Preferably, the activity of human SEP is determined by the assay method described above.

The present invention also relates to a method of identifying agents (such as compounds, other substances or compositions comprising the same) that selectively affect (such as inhibit or otherwise modify) the activity of human SEP and/or the expression thereof, the method comprising measuring the activity of human SEP and/or the expression thereof in the presence of the agent or after the addition of the agent in: (a) a cell line into which has been incorporated recombinant DNA comprising the DNA sequence shown in SEQ ID NO: 1 or SEQ ID NO: 5 or an allelic variation thereof, or (b) a cell population or cell line that naturally selectively expresses human SEP. Preferably, the activity of human SEP is determined by the assay method described above.

The present invention also relates to a method of screening an agent for modulation (preferably for specific modulation) of human SEP (or a derivative, homologue, variant or fragment thereof) activity or the expression of the nucleotide sequence coding for the same (including a derivative, homologue, variant or fragment thereof), the method comprising the steps of: (a) providing a candidate agent; (b) combining human SEP (or the derivative, homologue, variant or fragment thereof) or the nucleotide sequence coding for the same (or the derivative, homologue, variant or fragment thereof) with the candidate agent for a time sufficient to allow modulation under suitable conditions; and (c) detecting modulation of human SEP by the candidate agent (or the derivative, homologue, variant or fragment thereof) or the nucleotide sequence coding for the same (or the derivative, homologue, variant or fragment thereof) in order to ascertain if the candidate agent modulates human SEP (or the derivative, homologue, variant or fragment thereof) activity or the expression of the nucleotide sequence coding for the same (or the derivative, homologue, variant or fragment thereof).

The present invention also relates to a method of screening an agent for specific binding affinity with human SEP (or a derivative, homologue, variant or fragment thereof) or the nucleotide sequence coding for the same (including a derivative, homologue, variant or fragment thereof), the method comprising the steps of: (a) providing a candidate agent; (b) combining human SEP (or the derivative, homologue, variant or fragment thereof) or the nucleotide sequence coding for the same (or the derivative, homologue, variant or fragment thereof) with the candidate agent for a time sufficient to allow binding under suitable conditions; and (c) detecting binding of the candidate agent to human SEP (or the derivative, homologue, variant or fragment thereof) or the nucleotide sequence coding for the same (or the derivative, homologue, variant or fragment thereof) in order to ascertain if the candidate agent binds to human SEP (or the derivative, homologue, variant or fragment thereof) or the nucleotide sequence coding for the same (or the derivative, homologue, variant or fragment thereof).

The present invention also relates to a method of identifying an agent which is capable of modulating human SEP, the method comprising the steps of: (a) contacting the agent with human SEP (or a derivative, homologue, variant or fragment thereof) or the nucleotide sequence coding for the same (or the derivative, homologue, variant or fragment thereof); (b) incubating the mixture of step (a) with a bioactive peptide under conditions suitable for the proteolysis of the bioactive peptide; (c) measuring the amount of bioactive peptide proteolysis; and (d) comparing the amount of bioactive peptide proteolysis of step (c) with the amount of bioactive peptide proteolysis obtained with human SEP (or the derivative, homologue, variant or fragment thereof) or the nucleotide sequence coding for the same (or the derivative, homologue, variant or fragment thereof) incubated without the agent, thereby determining whether the agent affects (such as inhibits or selectively inhibits) bioactive peptide proteolysis.

Thus, in certain embodiments of the present invention, human SEP or a variant, homologue, fragment or derivative thereof and/or a cell line that expresses the human SEP or variant, homologue, fragment or derivative thereof may be used to screen for antibodies, peptides, or other agents, such as organic or inorganic molecules, that act as modulators of endopeptidase activity or for the expression thereof, thereby identifying a therapeutic agent capable of modulating bioactive peptide levels. For example, anti-human SEP antibodies capable of neutralising the activity of human SEP may be used to inhibit human SEP proteolysis of bioactive peptides, thereby increasing their levels. Alternatively, screening of peptide libraries or organic libraries made by combinatorial chemistry with recombinantly expressed human SEP or a variant, homologue, fragment or derivative thereof or cell lines expressing human SEP or a variant, homologue, fragment or derivative thereof may be useful for identification of therapeutic agents that function by modulating (e.g. inhibiting or selectively inhibiting) human SEP proteolysis of bioactive peptides. Synthetic compounds, natural products, and other sources of potentially biologically active materials can be screened in a number of ways deemed to be routine to those of skill in the art. For example, nucleotide sequences encoding the N-terminal region of human SEP may be expressed in a cell line, which can be used for screening of allosteric modulators, either agonists or antagonists, of human SEP activity. Alternatively, nucleotide sequences encoding the conserved catalytic domain of human SEP can be expressed in cell lines and used to screen for inhibitors or selective inhibitors of bioactive peptide proteolysis.

The ability of a test agent to interfere with human SEP activity or bioactive peptide proteolysis may be determined by measuring human SEP levels or bioactive peptide levels.

Accordingly, the present invention relates to a method of identifying a compound which is capable of modulating the bioactive peptide proteolysis activity of a human SEP, or a variant, homologue, fragment or derivative thereof, comprising the steps of (a) contacting the compound with a human SEP, or a variant, homologue, fragment or derivative thereof; (b) incubating the mixture of step (a) with a bioactive peptide under conditions suitable for the proteolysis of the bioactive peptide; (c) measuring the amount of bioactive peptide proteolysis; and (d) comparing the amount of bioactive peptide proteolysis of step (c) with the amount of bioactive peptide proteolysis obtained with the human SEP, or a variant, homologue, fragment or derivative thereof, incubated without the compound, thereby determining whether the compound stimulates or inhibits bioactive peptide proteolysis. In one embodiment of the method, the fragment may be from the N-terminal region of the human SEP and provides a method to identify allosteric modulators of the human SEP. In another embodiment of the present invention, the fragment may be from the carboxy terminal region of the human SEP and provides a method to identify inhibitors or selective inhibitors of bioactive peptide proteolysis.

The bioactive peptides may be full-length or fragments thereof and may be produced recombinantly or, preferably, synthetically. Preferably, said bioactive peptides are small synthetic peptides capable of being modulated (preferably cleaved by proteolysis/hydrolysis) by human SEP. More preferably, said synthetic peptides are labelled (preferably, fluorescently labelled, more preferably fluorescently labelled with intramolecularly quenchable fluorogenic dyes such as can be used in the FRET assay described herein).

Since human SEP may be involved in regulating bioactive peptide activity and/or in proteolysis of biologically inactive peptides into their active form, references to "bioactive peptide(s)" (and the like) hereinabove can also be taken to mean references to "biologically inactive peptide(s)" (and the like), with the context within which these references exist to be construed mutatis mutandis, as appropriate. For example, where the inhibition of human SEP activity might lead to increased levels of bioactive peptide(s), such inhibition might also, or instead, lead to increased levels of biologically inactive peptide(s), thereby leading to reduced levels of peptide(s) in their "active form".

A human SEP polypeptide, its immunogenic fragments or oligopeptides thereof can be used for screening therapeutic compounds in any of a variety of drug screening techniques. The polypeptide employed in such a test may be free in solution, affixed to a solid support, borne on a cell surface, or located intracellularly. The abolition of activity or the formation of binding complexes between a human SEP polypeptide and the agent being tested may be measured. Accordingly, the present invention relates to a method for screening one or a plurality of compounds for modulation (preferably specific modulation, such as specific binding affinity or inhibition) of human SEP or the expression thereof, or a portion thereof or variant, homologue, fragment or derivative thereof, comprising providing one or a plurality of compounds; combining a human SEP or a nucleotide sequence coding for the same or a portion thereof or variant, homologue, fragment or derivative thereof with the or each of a plurality of compounds for a time sufficient to allow modulation under suitable conditions; and detecting, for example, (i) binding of a human SEP, or portion thereof or variant, homologue, fragment or derivative thereof, to each of the plurality of compounds, thereby identifying the compound or compounds which modulate a human SEP or a nucleotide sequence coding for the same; or (ii) inhibition of a human SEP, or portion thereof or variant, homologue, fragment or derivative thereof, by each of the plurality of compounds, thereby identifying the compound or compounds which modulate (inhibit) a human SEP or a nucleotide sequence coding for the same. In such an assay, the plurality of compounds may be produced by combinatorial chemistry techniques known to those of skill in the art.

Another technique for drug screening provides for high throughput screening (HTS) of compounds having suitable binding affinity to the human SEP polypeptides and is based upon the method described in detail in Geysen, WO 84/03564, published on Sep. 13, 1984. In summary, large numbers of different small peptide test compounds are synthesized on a solid substrate, such as plastic pins or some other surface. The peptide test compounds are reacted with human SEP fragments and washed. A bound human SEP is then detected—such as by appropriately adapting methods well known in the art. A purified human SEP can also be coated directly onto plates for use in the aforementioned drug screening techniques. Alternatively, non-neutralising antibodies can be used to capture the peptide and immobilise it on a solid support.

This invention also contemplates the use of competitive drug screening assays in which neutralising antibodies capable of binding a human SEP specifically compete with a test compound for binding a human SEP. In this manner, the antibodies can be used to detect the presence of any peptide which shares one or more antigenic determinants with a human SEP.

The assay method of the present invention may be a high throughput screen (HTS). In this regard, the teachings of WO 84/03564 may be adapted for the human SEP of the present invention.

The teachings of U.S. Pat. No. 5,738,985 may be adapted for the assay method of the present invention.

Agents

The present invention also provides one or more agents identified by the assays methods and identification methods of the present invention.

The agent of the present invention can be, for example, an organic compound or an inorganic compound. The agent can be, for example, a nucleotide sequence that is antisense to all or part of the sequence shown in SEQ ID NO: 1 or SEQ ID NO: 5. Preferably, the agent will be a modulator of SEP activity, more preferably a SEP inhibitor (SEPi) or a selective SEPi.

A SEPi is a compound which inhibits the enzymatic activity of SEP, that is prevents it cleaving (by proteolysis) a substrate peptide, polypeptide or protein.

The invention further provides an agent of the present invention (or even a pharmaceutically acceptable salt thereof, or a pharmaceutically acceptable solvate thereof) or a pharmaceutical composition containing any of the foregoing, for use as a medicament.

The present invention also relates to the use of an agent to affect human SEP activity (such as to inhibit, selectively inhibit, modulate or agonise) in any one or more of the urogenital system, cardiovascular system, the neurological system, and the endocrine system.

Diagnostics

The present invention also provides a diagnostic composition for the detection of human SEP polynucleotide sequences. The diagnostic composition may comprise the sequence shown in SEQ ID NO: 1 or SEQ ID NO: 5 or a variant, homologue, fragment or derivative thereof, or a sequence capable of hybridising to all or part of the nucleotide sequence shown in SEQ ID NO: 1 or SEQ ID NO: 5 or an allelic variation thereof.

In order to provide a basis for the diagnosis of disease, normal or standard values from a human SEP polypeptide expression should be established. This is accomplished by combining body fluids or cell extracts (e.g. from the testis) taken from normal subjects, either animal or human, with antibody to a human SEP polypeptide under conditions suitable for complex formation which are well known in the art. The amount of standard complex formation may be quantified by comparing it to a dilution series of positive controls where a known amount of antibody is combined with known concentrations of a purified human SEP polypeptide. Then, standard values obtained from normal samples may be compared with values obtained from samples from subjects potentially affected by a disorder or disease related to a human SEP polypeptide expression. Deviation between standard and subject values establishes the presence of the disease state.

A human SEP polynucleotide, or any part thereof, may provide the basis for a diagnostic and/or a therapeutic compound. For diagnostic purposes, human SEP polynucleotide sequences may be used to detect and quantify gene expression in conditions, disorders or diseases in which human SEP activity may be implicated.

Human SEP encoding polynucleotide sequence may be used for the diagnosis of diseases resulting from expression of human SEP. For example, polynucleotide sequences encoding human SEP may be used in hybridisation or PCR assays of tissues from biopsies or autopsies or biological fluids, such as serum, synovial fluid or tumour biopsy, to detect abnormalities in human SEP expression. The form of such qualitative or quantitative methods may include Southern or northern analysis, dot blot or other membrane-based technologies; PCR technologies; dip stick, pin or chip technologies; and ELISA or other multiple sample format technologies. All of these techniques are well known in the art and are, in fact, the basis of many commercially available diagnostic kits.

Such assays may be tailored to evaluate the efficacy of a particular therapeutic treatment regime and may be used in animal studies, in clinical trials, or in monitoring the treatment of an individual patient. In order to provide a basis for the diagnosis of disease, a normal or standard profile for human SEP expression should be established. This is accomplished by combining body fluids or cell extracts taken from normal subjects, either animal or human, with human SEP or a portion thereof, under conditions suitable for hybridisation or amplification. Standard hybridisation may be quantified by comparing the values obtained for normal subjects with a dilution series of positive controls run in the same experiment where a known amount of purified human SEP is used. Standard values obtained from normal samples may be compared with values obtained from samples from subjects potentially affected by a disorder or disease related to expression of the human SEP coding sequence. Deviation between standard and subject values establishes the presence of the disease state. If disease is established, an existing therapeutic agent is administered, and treatment profile or values may be generated. Finally, the assay may be repeated on a regular basis to evaluate whether the values progress toward or return to the normal or standard pattern. Successive treatment profiles may be used to show the efficacy of treatment over a period of several days or several months.

The present invention also relates to the use of a human SEP polypeptide, or variant, homologue, fragment or derivative thereof, to produce anti-human SEP antibodies which can, for example, be used diagnostically to detect and quantify human SEP levels in disease states.

The present invention further relates to diagnostic assays and kits for the detection of human SEP in cells and tissues comprising a purified human SEP which may be used as a positive control, and anti-human SEP antibodies. Such antibodies may be used in solution-based, membrane-based, or tissue-based technologies to detect any disease state or condition related to the expression of human SEP protein or expression of deletions, variants, homologues, fragments or derivatives thereof.

Probes

Another aspect of the subject invention is the provision of nucleic acid hybridisation or PCR probes which are capable of detecting polynucleotide sequences, including genomic sequences, encoding human SEP coding region or closely related molecules, such as alleles. The specificity of the probe, i.e. whether it is derived from a highly conserved, conserved or non-conserved region or domain, and the stringency of the hybridisation or amplification (high, intermediate or low) will determine whether the probe identifies only naturally occurring human SEP coding sequence, or related sequences. Probes for the detection of related nucleic acid sequences are selected from conserved or highly conserved nucleotide regions of human SEP family members, such as the 3' region, and such probes may be used in a pool of degenerate probes. For the detection of identical nucleic acid sequences, or where maximum specificity is desired, nucleic acid probes are selected from the non-conserved nucleotide regions or unique regions of human SEP polynucleotides. As used herein, the term "non-conserved nucleotide region" refers to a nucleotide region that is unique to the human SEP coding sequence disclosed herein and does not occur in related family members, such as known SEPs.

PCR, as described in U.S. Pat. No. 4,683,195, U.S. Pat. No. 4,800,195 and U.S. Pat. No. 4,965,188 provides additional uses for oligonucleotides based upon the human SEP sequence. Such oligomers are generally chemically synthesized, but they may be generated enzymatically or produced from a recombinant source. Oligomers generally comprise two nucleotide sequences, one with sense orientation (5'→3') and one with antisense (3'←5') employed under optimised conditions for identification of a specific gene or condition. The same two oligomers, nested sets of oligomers, or even a degenerate pool of oligomers may be employed under less stringent conditions for detection and/or quantification of closely related DNA or RNA sequences.

The nucleic acid sequence for human SEP can also be used to generate hybridisation probes as previously described, for mapping the endogenous genomic sequence. The sequence may be mapped to a particular chromosome or to a specific region of the chromosome using well known techniques. These include in situ hybridisation to chromosomal spreads (Verma et al. (1988) Human Chromosomes: A Manual of Basic Techniques, Pergamon Press, New York City, USA), flow-sorted chromosomal preparations, or artificial chromosome constructions such as yeast artificial chromosomes (YACs), bacterial artificial chromosomes (BACs), bacterial PI constructions or single chromosome cDNA libraries.

In situ hybridisation of chromosomal preparations and physical mapping techniques such as linkage analysis using established chromosomal markers are invaluable in extending genetic maps. Examples of genetic maps can be found in Science (1995; 270:410f and 1994; 265:1981f). Often the placement of a gene on the chromosome of another mammalian species may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localised by genetic linkage to a particular genomic region, for example, AT to 11q22–23 (Gatti et al, (1988), Nature, 336:577–580), any sequences mapping to that area may represent associated or regulatory genes for further investigation. The nucleotide sequence of the subject invention may also be used to detect differences in the chromosomal location due to translocation, inversion, etc. between normal, carrier or affected individuals.

Pharmaceuticals

The present invention also provides a pharmaceutical composition for treating an individual in need of the same due to human SEP activity, the composition comprising a therapeutically effective amount of an agent that affects (such as inhibits or selectively inhibits) said activity and a pharmaceutically acceptable carrier, diluent or excipient.

Thus, the present invention also covers pharmaceutical compositions comprising the agents of the present invention (an agent capable of modulating the expression pattern of the nucleotide sequence of the present invention or the activity of the expression product thereof and/or an agent identified by an assay according to the present invention). In this regard, and in particular for human therapy, even though the agents of the present invention can be administered alone, they will generally be administered in admixture with a pharmaceutical carrier, excipient or diluent selected with regard to the intended route of administration and standard pharmaceutical practice.

By way of example, in the pharmaceutical compositions of the present invention, the agents of the present invention may be admixed with any suitable binder(s), lubricant(s), suspending agent(s), coating agent(s), or solubilising agent(s).

In general, a therapeutically effective daily oral or intravenous dose of the agents of the present invention is likely to range from 0.01 to 50 mg/kg body weight of the subject to be treated, preferably 0.01 to 20 mg/kg, more preferably 0.1 to 20 mg/kg. The agents of the present invention may also be administered by intravenous infusion, at a dose which is likely to range from 0.001–10 mg/kg/hr.

Thus, the present invention also provides a method of treating an individual in need of the same due to human SEP activity comprising administering to said individual an effective amount of the pharmaceutical composition of the present invention.

Typically, the physician will determine the actual dosage which will be most suitable for an individual patient and it will vary with the age, weight, sex and response of the particular patient. The above dosages are exemplary of the average case. There can, of course, be individual instances where higher or lower dosage ranges are merited, and such are within the scope of this invention.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intracavernosally, intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

For oral, parenteral, buccal and sublingual administration to subjects (such as patients), the daily dosage level of the agents of the present invention may typically be from 10 to 500 mg (in single or divided doses). Thus, and by way of example, tablets or capsules may contain from 5 to 100 mg of active agent for administration singly, or two or more at a time, as appropriate. It is also possible to administer the agents of the present invention in sustained release formulations.

In some applications, generally in humans, oral administration of the agents of the present invention is the preferred route, being the most convenient and can in some cases avoid disadvantages associated with other routes of administration—such as those associated with intracavernosal (i.c.) administration. In circumstances where the recipient suffers from a swallowing disorder or from impairment of drug absorption after oral administration, the drug may be administered parenterally.

For veterinary use, the agent of the present invention is typically administered as a suitably acceptable formulation in accordance with normal veterinary practice and the veterinary surgeon will determine the dosing regimen and route of administration which will be most appropriate for a particular animal. However, as with human treatments, it may be possible to administer the agent alone for veterinary treatments.

Typically, the pharmaceutical compositions—which may be for human or animal usage—will comprise any one or more of a pharmaceutically acceptable diluent, carrier or excipient. The choice of pharmaceutical carrier, excipient or diluent can be selected with regard to the intended route of administration and standard Pharmaceutical practice. As indicated above, the pharmaceutical compositions may comprise as—or in addition to—the carrier, excipient or diluent any suitable binder(s), lubricant(s), suspending agent(s), coating agent(s) or solubilising agent(s).

In some embodiments of the present invention, the pharmaceutical compositions will comprise one or more of: an agent that has been screened by an assay of the present invention; an agent that is capable of interacting with any one of the sequences shown in the Sequence Listing or Figures including derivatives, fragments, homologues or variants thereof or sequences capable of hybridising to the nucleotide sequence shown in SEQ ID NO: 1 or SEQ ID NO: 5.

Included in the scope of the invention are oligonucleotide sequences, antisense RNA and DNA molecules and ribozymes, which function to destabilise human SEP mRNA or inhibit translation of a human SEP. Such nucleotide sequences may be used in conditions where it would be preferable to increase levels of bioactive peptides.

A human SEP antisense molecule may provide the basis for the prophylaxis and/or treatment of various abnormal conditions related to, for example, increased human SEP activity.

A human SEP nucleic acid antisense molecule may be used to block the activity of the human SEP in conditions where it would be preferable to elevate bioactive peptide levels.

Expression vectors derived from retroviruses, adenovirus, herpes or vaccinia viruses, or from various bacterial plasmids, may be used for delivery of recombinant human SEP sense or antisense molecules to the targeted cell population. Methods which are well known to those skilled in the art can be used to construct recombinant vectors containing human SEP. Alternatively, recombinant human SEP can be delivered to target cells in liposomes.

The full length cDNA sequence and/or its regulatory elements enable researchers to use human SEP as a tool in sense (Youssoufian H and H F Lodish, (1993), Mol. Cell Biol., 13:98–104) or antisense (Eguchi et al, (1991), Annual Rev. Biochem., 60:631–652) investigations of gene function. Oligonucleotides, designed from the cDNA or control sequences obtained from the genomic DNA can be used in vitro or in vivo to inhibit expression. Such technology is now well known in the art, and sense or antisense oligonucleotides or larger fragments can be designed from various locations along the coding or control regions. Appropriate oligonucleotides, which can be 20 nucleotides in length, may be used to isolate human SEP sequences or closely related molecules from human libraries.

Additionally, human SEP expression can be modulated by transfecting a cell or tissue with expression vectors which express high levels of a human SEP fragment in conditions where it would be preferable to block endopeptidase activity thereby increasing bioactive peptide levels. Such constructs can flood cells with untranslatable sense or antisense sequences. Even in the absence of integration into the DNA, such vectors may continue to transcribe RNA molecules until all copies of the vector are disabled by endogenous nucleases. Such transient expression may last for a month or more with a non-replicating vector and even longer if appropriate replication elements are part of the vector system.

Since human SEP may be involved in regulating bioactive peptide activity and/or in proteolysis of biologically inactive peptides into their active form, references to "bioactive peptide(s)" (and the like) hereinabove can also be taken to mean references to "biologically inactive peptide(s)" (and the like), with the context within which these references exist to be construed mutatis mutandis, as appropriate. For example, where the inhibition of human SEP activity might lead to increased levels of bioactive peptide(s), such inhibition might also, or instead, lead to increased levels of biologically inactive peptide(s), thereby leading to reduced levels of peptide(s) in their "active form".

Modifications of gene expression can be obtained by designing antisense sequences to the control regions of the human SEP gene, such as the promoters, enhancers, and introns.

Oligonucleotides derived from the transcription initiation site, e.g. between −10 and +10 regions of the leader sequence, are preferred. Antisense RNA and DNA molecules may also be designed to block translation of mRNA by preventing the transcript from binding to ribosomes. Similarly, inhibition can be achieved using Hogeboom basepairing methodology, also known as "triple helix" base pairing. Triple helix pairing compromises the ability of the double helix to open sufficiently for the binding of polymerases, transcription factors, or regulatory molecules.

Thus the invention provides a pharmaceutical composition comprising an agent of the present invention (or even a pharmaceutically acceptable salt thereof, or a pharmaceutically acceptable solvate thereof) together with a pharmaceutically acceptable diluent, excipient or carrier.

The pharmaceutical composition could be for veterinary (i.e. animal) usage or for human usage.

Thus, the present invention therefore also relates to pharmaceutical compositions comprising effective amounts of inhibitors or antagonists of human SEP protein (including antisense nucleic acid sequences) in admixture with a pharmaceutically acceptable diluent, carrier or excipient (including combinations thereof).

The present invention yet further relates to pharmaceutical compositions which may comprise all or portions of human SEP polynucleotide sequences, human SEP antisense molecules, human SEP polypeptides, protein, peptide or organic modulators of human SEP bioactivity, such as inhibitors, selective inhibitors, antagonists (including antibodies) or agonists, alone or in combination with at least one other agent, such as stabilising compound, and may be administered in any sterile, biocompatible pharmaceutical carrier, including, but not limited to, saline, buffered saline, dextrose, and water.

Pharmaceutical Combinations

The pharmaceutical compositions of the present invention may be used in combination with one or more other pharmaceutically active agents, such as a potentiators or enhancers of cyclic GMP (such a phosphodiestertase type 5 inhibitor e.g. Sildenafil, or a nitric oxide donor, or a nitric oxide precursor e.g. L-argininase) and/or a centrally acting pharmaceutical (e.g. a dopamine receptor agonist or melanocortin receptor agonist, such as apomorphine or melanotan II). Teachings on the use of apomorphine as a pharmaceutical may be found in U.S. Pat. No. 5,945,117. In that particular document, apomorphine is delivered sub-lingually.

In addition, or in the alternative, the pharmaceutical compositions of the present invention may be used in combination with: one or more of a neutral endopeptidase (NEP) inhibitor (NEPi), one or more of a PDE5 inhibitor (PDE5i) (e.g. sildenafil (Pfizer), vardenafil (Bayer BA 38-9456) and IC351 (Cialis, Icos Lilly)), one or more of an NPY receptor antagonist, one or more of a PDE type 2 inhibitor, one or more of a nitric oxide (NO) donor (e.g. NMI-921), one or more of a dopamine receptor agonist (e.g. apomorphine, Uprima, Ixsene), one or more of a melanocortin receptor agonist (e.g. Melanotan II or PT14), one or more of a potassium channel opener (e.g. a $K_{ATP}$ channel opener (e.g. minoxidil, nicorandil) and/or a calcium activated potassium channel opener (e.g. BMS-204352), one or more of a α1-adrenoceptor antagonist (e.g. phentolamine, Vasofem, Vasomax), one or more of a VIP receptor agonist or VIP analogue (e.g. Ro-125-1553) or VIP fragments, one or more of a α-adrenoceptor antagonist with VIP combination (e.g. Invicorp, Aviptadil), one or more of a α2-adrenoceptor antagonist (e.g. yohimbine), one or more of an estrogen, estrogen and medroxyprogesterone or medroxyprogesterone acetate (MPA) or oestrogen and methyl testosterone hormone replacement therapy agent (e.g. HRT especially Premarin, Cenestin, Oestrofeminal, Equin, Estrace, Estrofem, Elleste Solo, Estring, Eastraderm, Eastraderm TTS, Eastraderm Matrix, Dermestril, Premphase, Prempro, Prempak, Premique, Estratest, Estratest HS, Tibolone), one or more of a testosterone replacement agent (including DHEA (dehydroandrostendione), testosterone (Tostrelle) or a testosterone implant (Organon)), one or more of a testosteroneloestradiol agent, one or more of an estrogen agonist (e.g. Lasofoxifene), one or more of a serotonin receptor agonist or antagonist (e.g. $5HT_{1A}$, $5HT_{2C}$, $5HT_{2A}$ and $5HT_3$ receptor agonists and antagonists; as described in WO 00/28993), one or more of a prostanoid receptor agonist (e.g. Muse, alprostadil, misoprostol), one or more of a purinergic receptor agonist (especially P2Y2 and P2Y4), or one or more antidepressant agents (e.g. bupropion (Wellbutrin), mirrtazapine, nefazodone).

Preferably, said pharmaceutical composition of the present invention used in such combinations described above is a SEPi. Preferred combinations of the present invention are: SEPi+NEPi and SEPi+PDE5i, in particular SEPi+Sildenafil.

General Methodology References

Although in general the techniques mentioned herein are well known in the art, reference may be made in particular to Sambrook et al., Molecular Cloning, A Laboratory Manual (1989) and Ausubel et al., Short Protocols in Molecular Biology (1999) 4$^{th}$ Ed, John Wiley & Sons, Inc. PCR is described in U.S. Pat. No. 4,683,195, U.S. Pat. No. 4,800,195 and U.S. Pat. No. 4,965,188.

Deposit

The following sample was deposited in accordance with the Budapest Treaty at the recognised depositary The National Collections of Industrial, Food and Marine Bacteria (NCIMB) at 23 St. Machar Drive, Aberdeen, Scotland, AB24 3RY, United Kingdom on 29 Jun. 2001:
NCIMB number NCIMB 41110 is *E. coli* MSSE82.

The depositor was Pfizer Limited, Ramsgate Road, Sandwich, Kent, CT13 9NJ, United Kingdom.

One skilled in the art could readily grow the above-mentioned *E. coli* clone (NCIMB 41110) in Luria Broth containing ampicillin and isolate the plasmid DNA of the clone using the alkali lysis method as described in Sambrook, et al., eds. (1989) Molecular Cloning: A Laboratory Manual, Cold Spring Harbor Laboratory Press, New York, N.Y., USA. The di-deoxy termination method as described by Sanger et al. (Proceedings of the National Academy of Sciences (USA), (Dec. 1977), 74(12) :5463–5467) and modified by Applied Biosystems, Foster City, Calif., USA (see Applied Biosystems manufacturer's literature) for fluorescent detection could then be used to sequence the DNA and identify human SEP.

The terms "cell" or "cells" used herein when referring to the above-mentioned deposited biological material deposited under Accession Number NCIMB 41110 are interchangeable with the equivalent terms "micro-organism" or "micro-organisms" or "bacterium" or "bacteria".

The present invention also encompasses sequences derivable and/or expressable from that deposit and embodiments comprising the same. The present invention also encompasses partial sequences derivable and/or expressable from that deposit and embodiments comprising the same, wherein those partial sequences code for active polypeptides (active enzymatic sites). The present invention also encompasses proteins comprising sequences derivable and/or expressable from that deposit and embodiments comprising the same. The present invention also encompasses proteins comprising partial sequences derivable and/or expressable from that deposit and embodiments comprising the same, wherein those partial sequences code for active polypeptides (active enzymatic sites).

EXAMPLES

The present invention will now be described, by way of example only, with reference to the accompanying Figures and Sequence Listing.

1. Identification of Human SEP

Database Mining

The novel gene of human SEP was found by mining databases of human expressed sequence tags (ESTs) using the neprilysin protein as probe and the BLAST algorithm. EST hits (database=Incyte Gold™; gene id.=241161) were then assembled into contiguous sequence which predicted a large fragment of coding sequence. This corresponds to the catalytic domain by homology with the neprilysin protein sequence (60% identity). Probes for PCR cloning were designed using this region of the predicted coding sequence for the novel gene. Thereafter, further mining of unfinished sequence from the human genomic database identified 5 predicted exons, which were hypothesised to belong to the same novel gene in the missing N-terminal region. This was later confirmed following sequencing of the full length clone obtained from human testis library (see below).

The novel human SEP sequence includes 3' UTR and part of the coding sequence in the highly conserved C-terminal region of human SEP which contains one of the two active catalytic sites. The novel human SEP appears to contain an insert of 37 amino-acids.

Isolation of Full Length Human SEP cDNA

An oligonucleotide (5'-ctgtcttgatggattggatg-3') (SEQ ID NO: 3) was designed using partial human SEP cDNA sequence from the above mentioned assembly of contiguous expression sequence tags (ESTs) that would enable longer human SEP cDNAs to be amplified from cDNA libraries using 5'-RACE (rapid amplification of 5' cDNA ends) PCR.

A panel of 12 arrayed 96-well format human Rapid-Screen™ cDNA libraries were then screened by 5'-RACE PCR. cDNAs corresponding to human SEP were identified in libraries derived from brain, liver, placenta, small intestine, and testis.

None of these cDNAs were full length, so further 5'-RACE was performed on the panel of libraries using a primer (5'-gtccttggcagtcgaattctcc-3') (SEQ ID NO: 4) designed from the sequence of one of the longer, but partial length cDNAs from testis. This identified a longer (~3.0 kb), putative full length cDNA clone in the testis library which was isolated and sequenced from both ends (FIG. 9 and FIG. 11). The full length human SEP clone was termed MSSE82 (and was deposited at NCIMB under Accession Number NCIMB 41110), with the full length cDNA cloned into the pCMV6-XL4 vector which has Genbank accession number #AF067196. The predicted amino acid sequence is shown in FIG. 10.

2. Tissue Distribution of Human SEP mRNA

A multiple tissue messenger RNA blot was probed for human SEP. SEP mRNA was detected in a testis sample but not in other tissues.

A fragment of DNA corresponding to the entire human SEP coding sequence was amplified by PCR using the SEP clone MSSE82 as a template. The fragment was radiolabelled with $^{32}P$ dCTP using a megaprime kit (Amersham PLC, UK). The radiolabelled fragment was used as a hybridisation probe to screen a multiple tissue mRNA array (dot blot) (from Clontech, USA) containing mRNAs from a selection (76) of different human tissues and cell lines. Following hybridisation and washing, the blot was subjected to autoradiography. A signal was detected from the testis, but not other tissues.

3. Production of Recombinant SEP Enzyme

A culture of Chinese Hamster Ovary (CHO) cells is transfected with the plasmid MSSE82 using the lipofectamine method as described in the lipofectamine reagent protocol (Invitrogen Ltd, Paisley, UK). The cell media is harvested at 24 or 48 hours post-transfection, and cleared of cell debris by centrifugation at 3000 g for 5 min. The media is then dialyzed overnight at 4° C. against 50 mM HEPES pH 7.4/10% glycerol, using a "slide a lyser" (from Pierce and Warner, Chester UK). The dialyzed sample is then frozen in aliquots and stored under liquid nitrogen.

4. Assay of SEP Peptidase Activity

SEP Assay

Background

The SEP assay is based on a FRET assay developed by Carvalho et al. for use with NEP (Carvalho et al., Annal. Biochem. 237, pp. 167–173 (1996)). The SEP FRET assay utilises a similar, although not identical, intramolecularly quenched fluorogenic peptide substrate, but substituted with a novel combination of fluorogenic donor/acceptor dyes, specifically Rhodamine green (Molecular Probes, Inc.) and QSY7 (Molecular Probes, Inc.).

The endopeptidase activity of SEP is measured by monitoring its ability to proteolyse the synthetic peptide substrate Rhodamine green-Gly-Gly-dPhe-Leu-Arg-Arg-Val-Cys (QSY7)-βAla-NH$_2$ (SEQ ID NO: 8).

The two fluorophores (fluorogenic dyes) chosen for this assay have overlapping emission and absorption spectra and hence are suitable for energy transfer. The Rhodamine green acts as a donor and when excited at 485 nm gives out an emission (fluorescence) at 535 nm which in turn excites the QSY7 (FRET is occurring). The QSY7 is fluorescently silent and so gives off no emission above 535 nm hence no signal is observed (the Rhodamine green emission is quenched).

Upon cleavage (selective hydrolysis) by SEP at the Arg-Val peptide bond of the peptide substrate, the Rhodamine green and QSY7 moieties move apart and so upon excitation at 485 nm, energy transfer can no longer take place. As a result, an increase in fluoresence is observed at 535 nm for the Rhodamine green.

Preparation of the Synthetic Peptide Substrate

Experimental:

Peptide assembly was completed on 0.25 mmol FMOC-PAL-PEG-PS resin by solid phase peptide synthesis protocols using modifications to manufacturer supplied (Applied Biosystems, Foster City, Calif., USA) 9-fluoreneylmethoxycarbonyl (FMOC)-based synthesis cycles. Our modified cycles deprotect the amino terminus with 2×5 minute treatments with 20% piperidine/N-methylpyrrolidinone (NMP); the efficiency of which is monitored by UV absorbance at 301 nm by passage of a small aliquot of deprotection solution through a UV absorbance detector. In a separate cartridge, the incoming amino acid is activated with 0.9 equivalents each of 2-(1H-Benzotriazole-1-yl)-1,1,3,3 tetramethyluronium hexafluorophosphate (HBTU)/1-Hydroxybenzotriazole (HOBt) dissolved in N,N-dimethylformamide (DMF). 2 equivalents of diisopropylethyl amine (DIEA) are added. Concurrently, the resin is then washed with NMP to remove deprotection by-products. The wash solution is drained from the resin and the activated amino acid ester is transferred to the resin and stirred to allow coupling to the amino terminus for 20 minutes. The residual coupling solution is drained and the resin washed again with NMP. To ensure peptide homogeneity, a solution of 0.4M Acetic Anhydride/0.04M HOBt in NMP and 12 mmole DIEA are added to the resin to acetylate any potential unreacted sites. Finally, the resin is washed with NMP, drained, then washed with a mixture of 1:1 dichloromethane/2,2,2-trifluoroethanol and drained. This typifies one cycle of peptide synthesis. The completed synthesis resin was cleaved and deprotected using Reagent K (King, D. S. et. al., (1990), Int. J. Pep. Prot. Res., 36, pp. 255–66) affording 251 mg (100%) crude peptide CP1 Electrospray mass spectrometry (ESMS) (m/z calculation (calc.)=977.21 (MH+average), obs.=977.47).

Attachment of QSY-7 to Cysteine:

50 mg (51 μmol) of crude CP1 was dissolved in solution of 10% DIEA/DMF containing 45 mg (52.4 μmol) QSY-7 maleimide After 10 minutes, the reaction was judged to be incomplete via HPLC-MS analysis and an additional 30 mg (30.7 μmol) crude peptide was added. After 30 additional minutes, the reaction was judged via HPLC-MS to be complete and all starting reagents consumed. The product was isolated by C18 preparative HPLC chromatography and fractions exhibiting desired product molecular weight by Matrix Assisted Laser Desorption Ionization mass spectrometry (MALDI-MS) were pooled and lyophilized to 73.7 mg (50%) of a purple powder, CP2 ESMS (m/z calc.=1797.86 (MH+monoisotopic), obs.=1797.86).

Attachment of bis(trifluoroacetyl) Rhodamine Green to the Amino Terminus:

73.7 mg (41 μmol) of CP2 was dissolved in a 2% DIEA/DMF solution containing 35 mg (52.8 μmol) Rhodamine Green carboxylic acid, trifluoroacetamide, succinimidyl ester (5(6)-CR 110 TFA, SE) *mixed isomers*. After 2 hours, the reaction was judged to be complete via HPLC-MS analysis. The product was isolated via C4 preparative HPLC chromatography and fractions exhibiting desired product molecular weights (MALDI-MS) were pooled and lyophilized to 71.4 mg (74%) of a purple powder CP3 ESMS (m/z calc. 2345.92 (MH+monoisotopic), obs.=2345.47).

Removal of Trifluoroacetyl Protecting Groups from Rhodamine Green:

71.4 mg (30.4 μmol) of CP3 was dissolved in 10 ml 4:1 CH$_3$CN/H$_2$O. To this was added 200 mg (1886 μmol) Na$_2$CO$_3$. After 16 hr. vortexing, the supernatant was decanted from the insoluble material. The reaction vessel was rinsed with 1 ml DMSO; this was combined with the supernatant and the product isolated via C4 preparative HPLC chromatography. Fractions exhibiting product molecular weights (MALDI-MS) were combined and lyophilized to 64 mg (98%) of a purple powder, CP4 ESMS (m/z calc.=2155.54 (MH+average), obs.=2155.27). CP4 is the desired synthetic peptide substrate Rhodamine green-Gly-Gly-dPhe-Leu-Arg-Arg-Val-Cys(QSY7)-βAla-NH$_2$ (SEQ ID NO: 8).

Materials:

All reagents were purchased of the highest commercial purity available and were used without further refinement. All reagents for peptide synthesis were purchased from Applied Biosystems, Foster City, Calif., USA with the following exceptions: QSY™-7 maleimide (Catalog number Q-10257) and Rhodamine Green carboxylic acid, trifluoroacetamide, succinimidyl ester (5(6)-CR 110 TFA, SE) *mixed isomers* (Catalog number R-6112) were purchased from Molecular Probes, Inc., OR, USA; FMOC-PAL-PEG-PS was purchased from Perseptive Biosystems, MA, USA (Catalog number GEN913384); FMOC-B-Alanine and FMOC-d-phenylalanine were purchased from Novabiochem, CA, USA; FMOC-Arg(Pbf)-OH was purchased from AnaSpec, Inc., CA, USA; 2,2,2-Trifluoroethanol was purchased from Aldrich, Wis., USA. Sodium Carbonate was purchased from Fisher, Pa., USA.

Preparative HPLC chromatography was performed on Vydac (CA, USA) C18 (Catalog number 218TP1022) or C4 (Catalog number 214TP1022) columns at 10 ml/min flow rate eluting with a linear gradient of 0% to 80%(A=5% $CH_3CN$/0.1% TFA/94.9% $H_2O$, B=100% $CH_3CN$) over 30 minutes collecting 30 second time fractions. Analytical HPLC-MS was performed using a Micromass (Manchester, UK) LCT mass spectrometer (masses based on externally calibrated standards) coupled with a Waters (MA, USA) 2690 HPLC inlet and a Waters 996 photodiode array detector performing chromatography on a Vydac C4 (Catalog number 214TP5415) column with a linear gradient of 0% to 80%(A=5% $CH_3CN$/0.1% TFA/94.9% $H_2O$, B=100% $CH_3CN$) over 30 minutes at 1 ml/min flow rate. Deconvoluted molecular weights were calculated from multiply charged observed ions using Micromass transform software. MALDI-MS were obtained on a Perseptive Biosystems Voyager-DE linear mass spectrometer using alpha cyano 4-hydroxy cinnamic acid matrix (Hewlett Packard, Calif., USA) and reported masses based on external calibration.

Process (Including Chemical Structures):

CP4 (=synthetic peptide substrate Rhodamine green-Gly-Gly-dPhe-Leu-Arg-Arg-Val-Cys(QSY™-7)-βAla-$NH_2$) (SEQ ID NO: 8) is synthesized by incorporating the key intermediate CP3 in a solid phase peptide synthesis scheme.

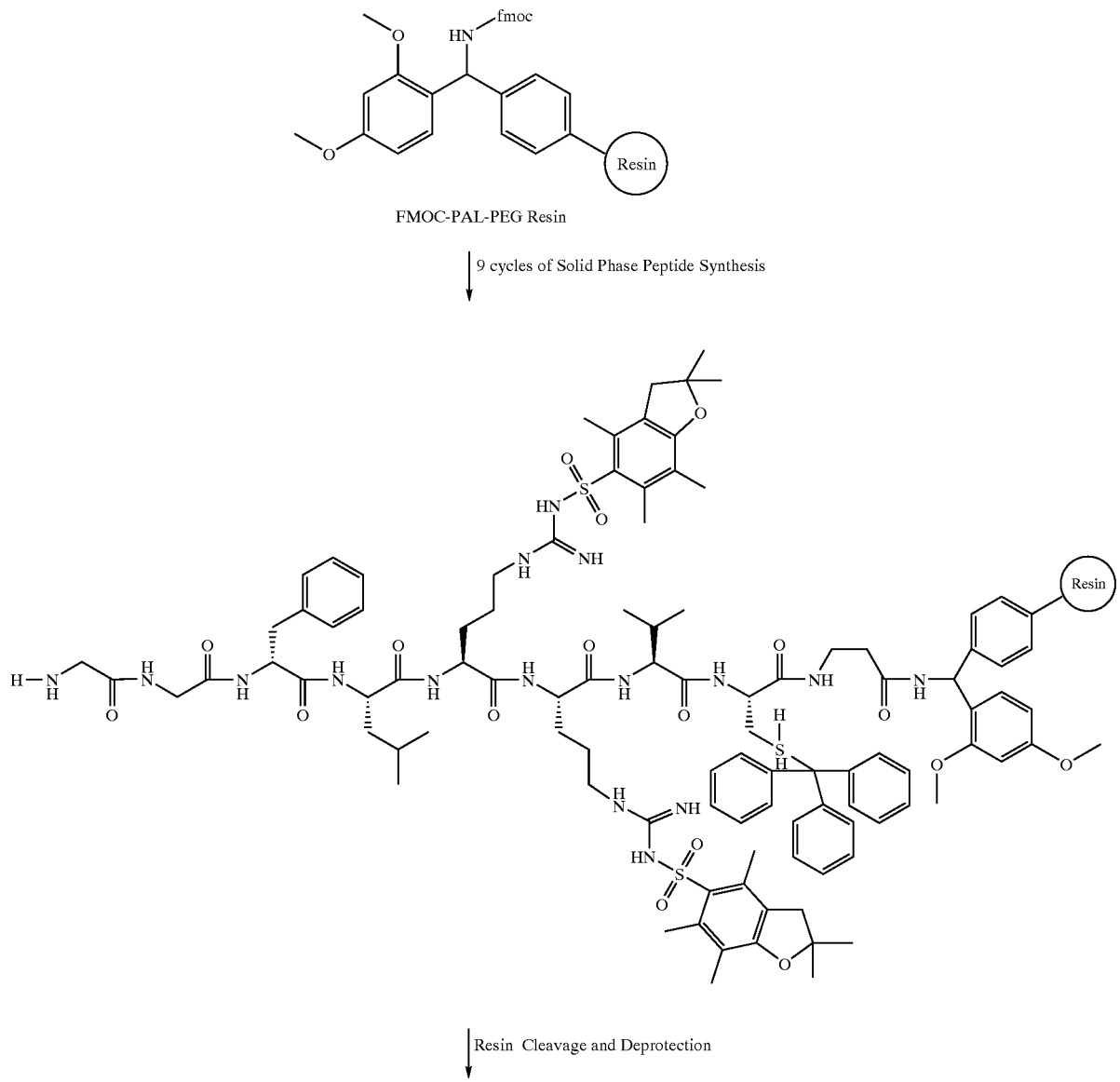

Scheme 1

FMOC-PAL-PEG Resin 9 cycles of Solid Phase Peptide Synthesis

Resin Cleavage and Deprotection

-continued

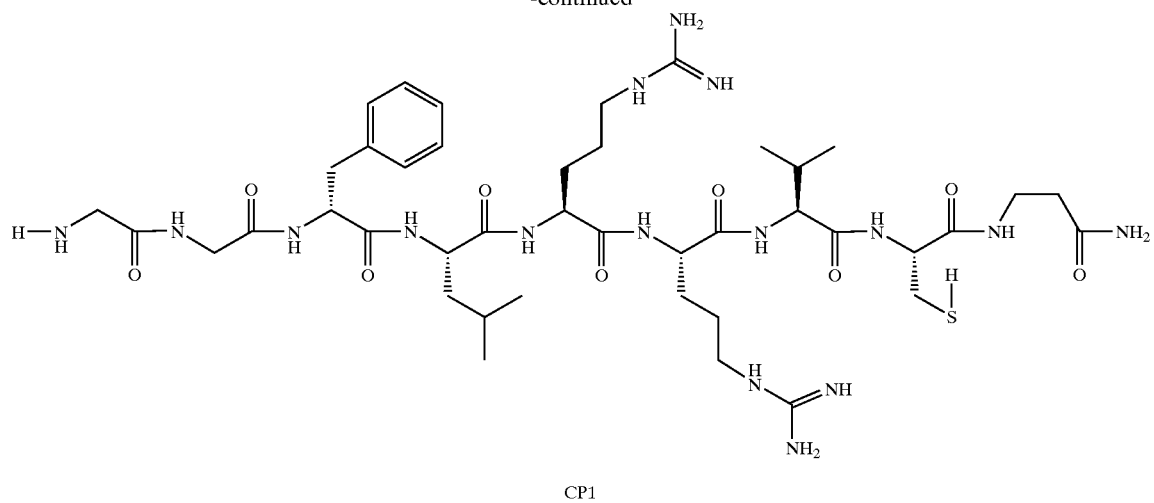

CP1

In summary, FMOC-PAL-PEG Resin is elaborated using Solid Phase Peptide Synthesis protocols optimized for efficiency of yield and time. These cycles (full details supra) incorporate 2 FMOC deprotections, washes, a single coupling of HBTU activated amino acid, washes, capping and finally, washing first with NMP then with 1:1 trifluoroethanol/dichloromethane. These washes help to relax resin secondary structure allowing for thorough deprotection and efficient coupling of the next incoming amino acid during the next cycle.

CP2 is synthesized (full details supra) according to Scheme 2:

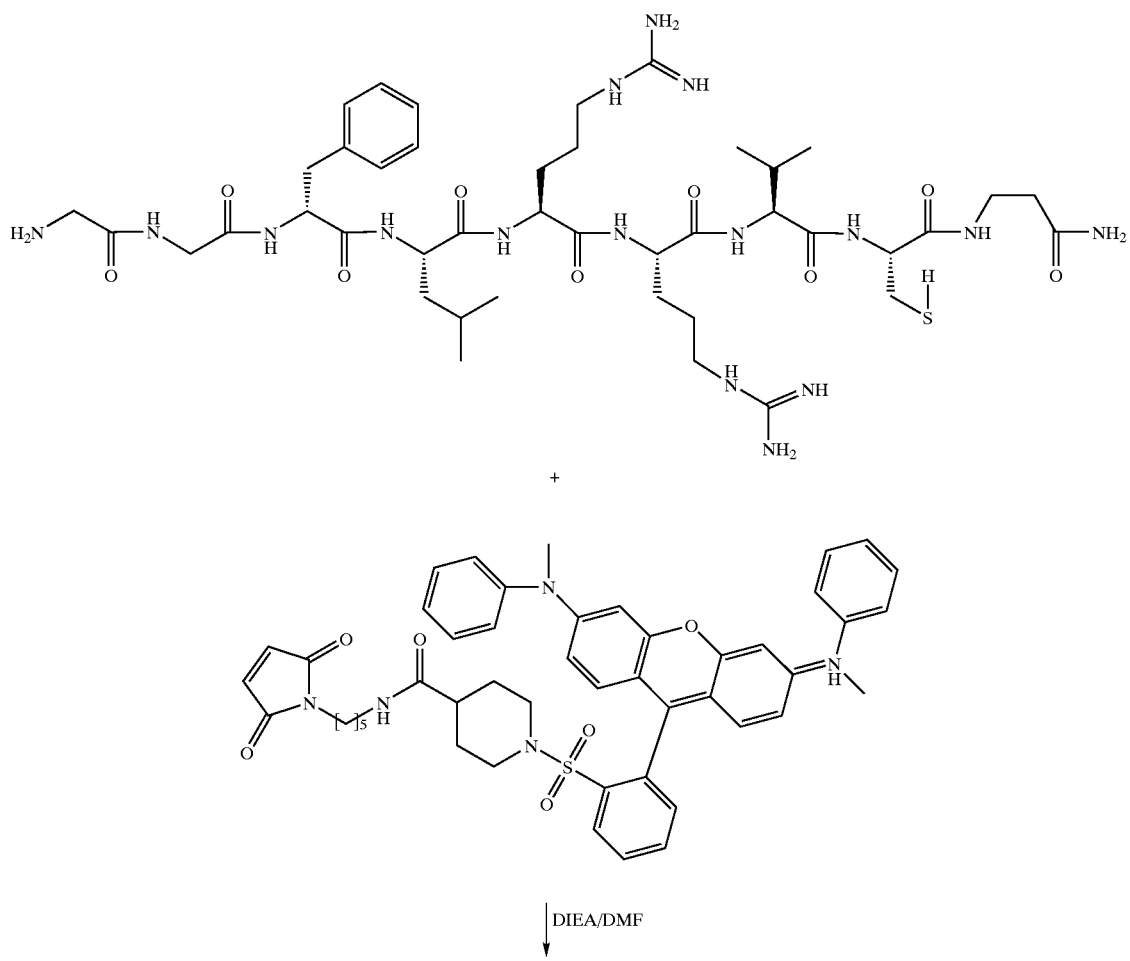

-continued
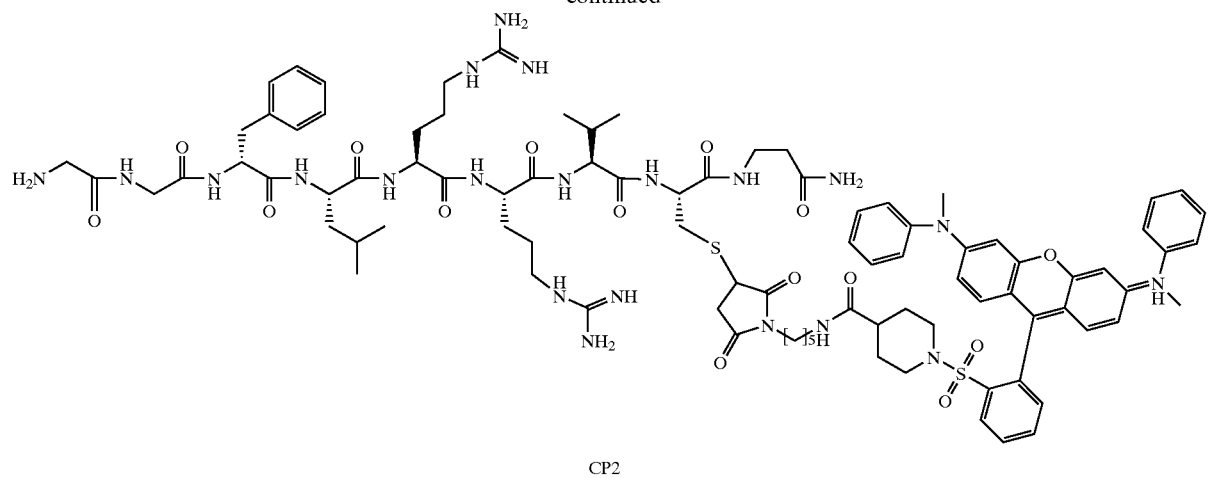
CP2
Following this incorporation of the QSY-7 tag, the second fluorophore, Rhodamine Green is added as the bis-trifluoroacetyl protected dye according to Scheme 3:

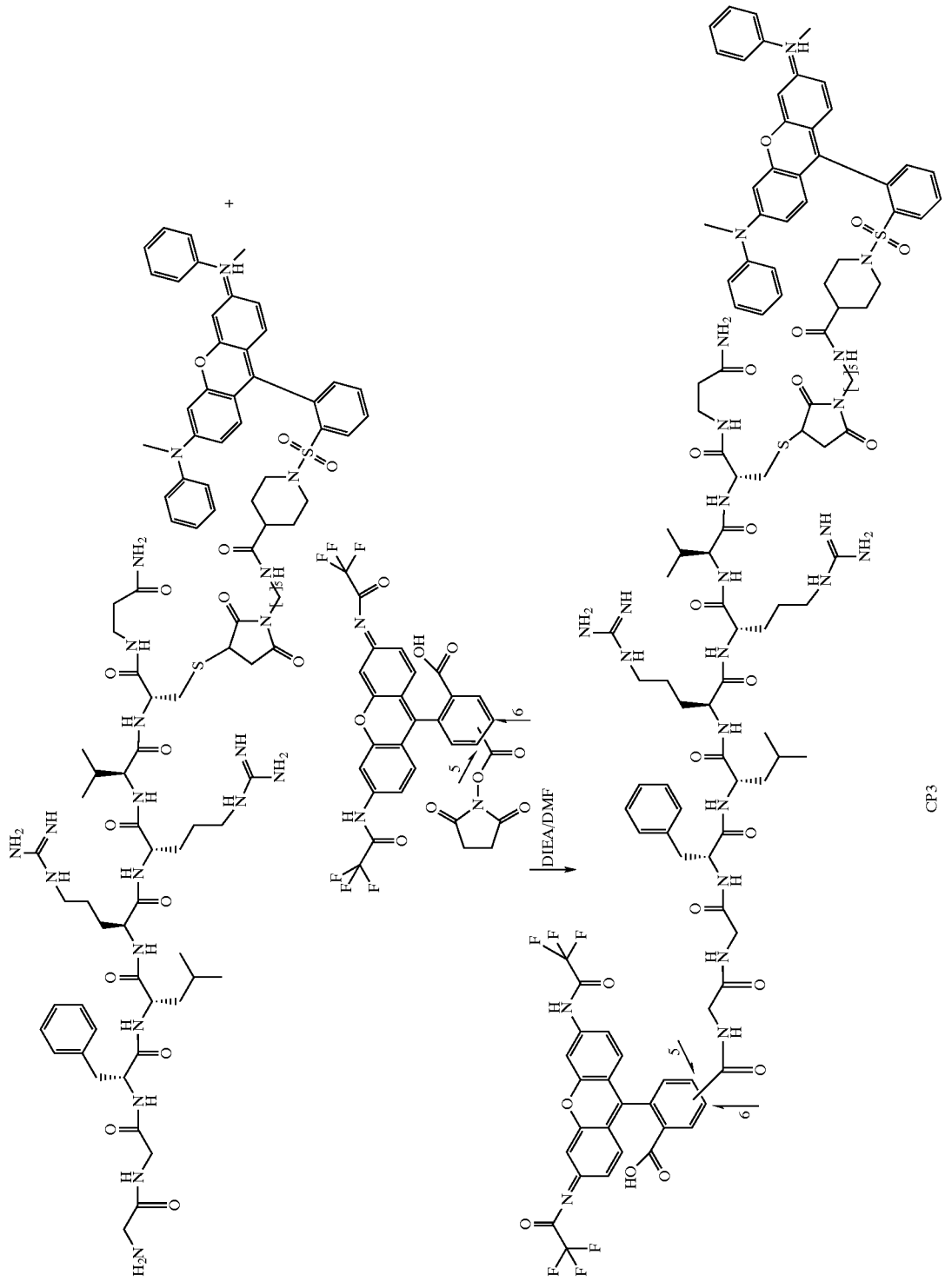

Finally, the trifluoroacetyl groups are removed by treatment with Na$_2$CO$_3$ affording the desired substrate, CP4:

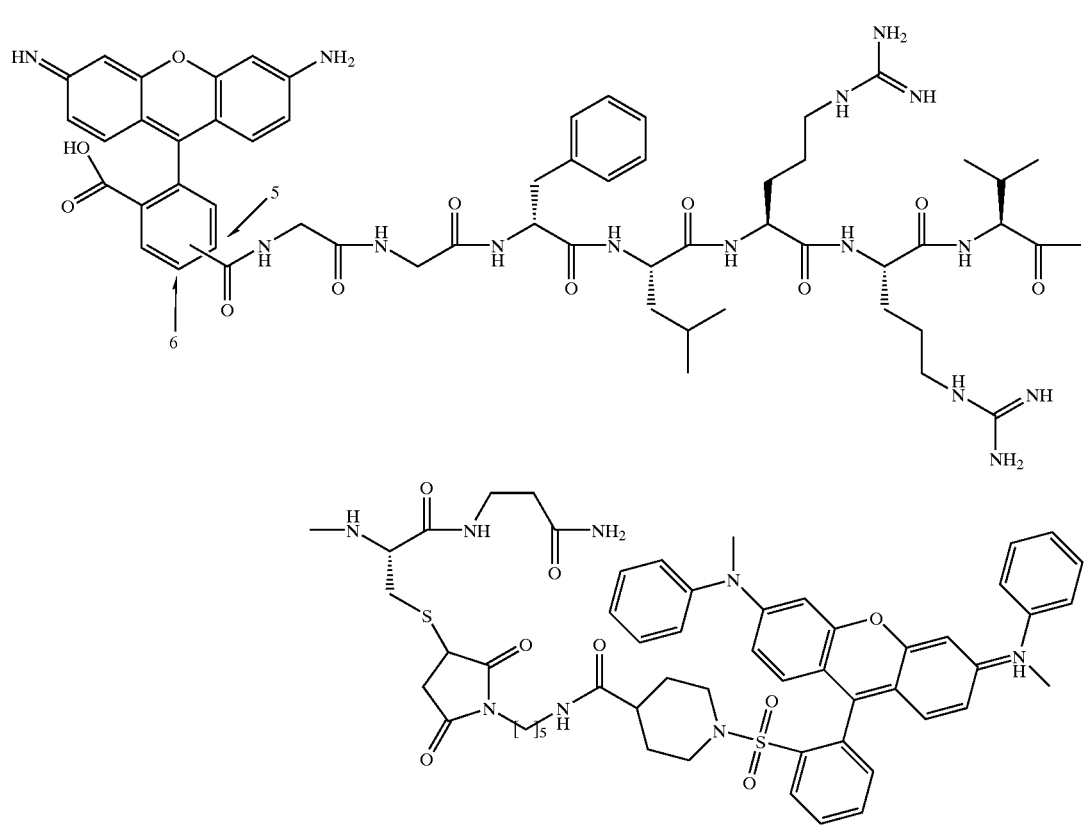

CP4

Assay

Reagents for the assay are first prepared as follows:

A substrate solution is made up by resuspending the substrate Rhodamine green-Gly-Gly-dPhe-Leu-Arg-Arg-Val-Cys(QSY7)-βAla-NH$_2$ (SEQ ID NO: 8) in 50 mM HEPES buffer pH 7.4 (Sigma, UK) at a concentration of 2 μM, then adding 1 EDTA-free protease inhibitor cocktail tablet (Roche Diagnostics, UK) per 25 ml.

An aliquot of SEP enzyme described above is thawed then diluted in 50 mM HEPES, pH 7.4 by a predetermined factor specific to each enzyme batch, such that 50 μl contains sufficient enzyme to convert approximately 30% of substrate to product during the assay.

A 4% DMSO solution comprised of 4 ml DMSO plus 96 ml 50 mM HEPES pH 7.4 is prepared.

A product solution is prepared by adding 500 μl of substrate solution to 250 μl enzyme solution plus 250 μl of 4% DMSO solution, and incubating at 37° C. for 16 hours.

Assays are set up as follows:

In a black 96 well microtitre plate, 100 μl of substrate solution is added to 50 μl of 4% DMSO solution. A similar non-specific background blank is also set up in which the 50 μl of 4% DMSO solution additionally contains 40 μM phosphoramidon. 50 μl of enzyme solution is added to the assay and blank, and the 96 well plate placed in a BMG galaxy fluorescence reader, operating with the Biolise software package (BMG Lab technologies, Offenberg, Germany).

The plate is incubated in the fluorescence reader for 1 hour at 37° C. and a fluorescence measurement taken every 3 minutes (Excitation (Ex) 485 nm/Emission (Em) 535 nm).

The proteolytic activity of SEP corresponds to the rate of increase in fluorescence of the sample—rate of increase in fluorescence units of the non-specific background blank. The maximum velocity measurement (MaxV) calculated by the software over four successive readings is used for this calculation.

A fluorescence measurement taken from 200 μl of product in a well on an identical microtitre plate is taken. If required this value is used, together with the measured fluorescence units from the 60 min timepoint of the SEP assay, to calculate the percentage (%) of the substrate proteolysed during the 1 hour incubation period or to convert the measured rates of fluorescence increase into other useful units such as ng substrate proteolysed/min/ml enzyme.

The assay is used to calculate enzyme kinetic parameters such as Vmax and Km following standard principles described in *Fundamentals of Enzyme Kinetics* by Athel Cornish Bowden, 1979, published by Butterworths.

Using the SEP Assay to Determine the Inhibition Parameters of SEP Inhibitors

To determine the IC$_{50}$ of SEP inhibitors (for example phosphoramidon), multiple SEP assays are performed as described above with a range of test concentrations of inhibitor included in the 50 μl of DMSO solution (made by appropriate dilution of a 10 mM 100% DMSO stock of inhibitor with 4% DMSO/50 mM HEPES pH 7.4.). Using a suitable standard graph fitting computer program, a sigmoidal dose response curve is fitted to a plot of log inhibitor concentration versus MaxV (or % inhibition or % activity). The IC$_{50}$ is calculated as the inhibitor concentration causing 50% maximal inhibition. Typically for a given $IC_{50}$ determination, a dose range of at least 10 inhibitor concentrations differing in half log unit increments is used.

The SEP assay is used to determine the Ki and mode of inhibition (i.e. whether the inhibition is competitive, mixed, non-competitive, etc.) following standard enzymology principles as described, for example, in *Fundamentals of Enzyme Kinetics* by Athel Cornish Bowden, 1979, published by Butterworths.

5. An Animal Model of Sexual Arousal

In our studies we have developed a robust reproducible model of the physiology of male and female sexual arousal. This model uses an anaesthetised rabbit and employs Laser Doppler technologies to monitor intracavernosal pressure and genital blood flow whilst routinely recording cardiovascular parameters. We are capable of measuring small changes in intracavernosal pressure within the penis and vaginal (and even clitoral) blood flow induced by pelvic nerve stimulation or infusion of VIP in the absence and presence of test agents.

We believe that our animal model directly reflects the clinical data. Hence, this model can be used to study candidate agents for the prophylaxis and/or treatment of MED and FSAD, such as measuring enhancement of penile erection via increases in intracavernosal pressure and enhancement vaginal or clitoral blood flow.

Identifying VIP and Other Neuropeptides as Potential Substrates that are Involved in Male and Female Sexual Arousal The ability of SEP to degrade the pro-sexual neuropeptide known as the vasoactive intestinal peptide (VIP) is measured by making use of, for example, a radioimmunoassay (RIA), such as the VIP RIA, that can be obtained commercially from Peninsula Laboratories, CA, USA.

A sample of SEP enzyme, typically 5–100 $\mu$l of recombinant SEP (produced by the method described above) is incubated with a sample of VIP peptide, typically 1–10 ng for 5 hours at 37° C., in a buffer such as 50 mM HEPES, pH 7.4. A negative control identical to this but also containing 10 $\mu$M phosphoramidon is set up and treated in an identical manner. After the incubation period, the quantity of VIP remaining in both the sample and the negative control is determined using the RIA as per manufacturer's instructions. The reduction in quantity of VIP in the sample relative to the negative control is a measure of the VIP proteolysing activity of SEP. The assay is used to determine enzyme kinetic parameters such as Vmax and Km following standard principles as described, for example, in Fundamentals of Enzyme Kinetics by Athel Cornish Bowden, 1979, published by Butterworths.

6. Animal Test Methods for SEP Inhibitors

Female Sexual Dysfunction Animal Model

Anaesthetic Protocol

Female New Zealand rabbits (~2.5 kg) are pre-medicated with a combination of Medetomidine (Domitor®) 0.5 ml/kg i.m., and Ketamine (Vetalar®) 0.25 ml/kg i.m. whilst maintaining oxygen intake via a face mask. The rabbits are tracheotomised using a Portex™ uncuffed endotracheal tube 3 ID., connected to a ventilator and maintained at a ventilation rate of 30–40 breaths per minute, with an approximate tidal volume of 18–20 ml, and a maximum airway pressure of 10 cm $H_2O$. Anaesthesia is then switched to Isoflurane and ventilation continued with $O_2$ at 2 l/min. The right marginal ear vein is cannulated using a 23G or 24G catheter, and Lactated Ringer solution perfused at 0.5 ml/min. The rabbit is maintained at 3% Isoflurane during invasive surgery, dropping to 2% for maintenance anaesthesia.

Cannulation of Vessels

The left groin area of the rabbit is shaved and a vertical incision is made approximately 5 cm in length along the thigh. The femoral vein is exposed, isolated and then cannulated with a PVC catheter (17G; Portex Limited, Hythe, Kent, UK) for the infusion of drugs and compounds. Cannulation is repeated for the femoral artery, inserting the catheter to a depth of 10 cm to ensure that the catheter reaches the abdominal aorta. This arterial catheter is linked to a Gould system to record blood pressure. Samples for blood gas analysis are also taken via the arterial catheter. Systolic and diastolic pressures are measured, and the mean arterial pressure calculated using the formula [(diastolic×2+systolic)÷3]. Heart rate is measured via the pulse oxymeter and Po-ne-mah data acquisition software system (Ponemah Physiology Platform, Gould Instrument Systems, Inc., OH, USA).

Stimulation of the Pelvic Nerve

A ventral midline incision is made into the abdominal cavity. The incision is about 5 cm in length just above the pubis. The fat and muscle is bluntly dissected away to reveal the hypogastric nerve which runs down the body cavity. It is essential to keep close to the side curve of the pubis wall in order to avoid damaging the femoral vein and artery which lie above the pubis. The sciatic and pelvic nerves lie deeper and are located after further dissection on the dorsal side of the rabbit. Once the sciatic nerve is identified, the pelvic nerve is easily located. The term pelvic nerve is loosely applied; anatomy books on the subject fail to identify the nerves in sufficient detail. However, stimulation of the nerve causes an increase in vaginal and clitoral blood flow, and innervation of the pelvic region. The pelvic nerve is freed away from surrounding tissue and a Harvard bipolar stimulating electrode is placed around the nerve. The nerve is slightly lifted to give some tension, then the electrode is secured in position. Approximately 1 ml of light paraffin oil is placed around the nerve and electrode. This acts as a protective lubricant to the nerve and prevents blood contamination of the electrode. The electrode is connected to a Grass S88 Stimulator. The pelvic nerve is stimulated using the following parameters: 5V, pulse width 0.5 ms, duration of stimulus 10 seconds and a frequency range of 2 to 16 Hz. Reproducible responses are obtained when the nerve is stimulated every 15–20 minutes.

A frequency response curve is determined at the start of each experiment in order to determine the optimum frequency to use as a sub-maximal response, normally 4 Hz. The compound(s) to be tested are infused, via the femoral vein, using a Harvard 22 infusion pump allowing a continuous 15 minute stimulation cycle.

Positioning of the Laser Doppler Probes

A ventral midline incision is made, at the caudal end of the pubis, to expose the pubic area. Connective tissue is removed to expose the tunica of the clitoris, ensuring that the wall is free from small blood vessels. The external vaginal wall is also exposed by removing any connective tissue. One Laser Doppler flow probe is inserted 3 cm into the vagina, so that half the probe shaft is still visible. A second probe is positioned so that it lay just above the external clitoral wall. The position of these probes is then adjusted until a signal is obtained. A second probe is placed just above the surface of a blood vessel on the external vaginal wall. Both probes are clamped in position.

Vaginal and clitoral blood flow is recorded either as numbers directly from the Flowmeter using Po-ne-mah data acquisition software (Ponemah Physiology Platform, Gould Instrument Systems, Inc.), or indirectly from Gould chart recorder trace. Calibration is set at the beginning of the experiment (0–125 ml/min/100 g tissue).

Infusion of Vasoactive Intestinal Peptide (VIP)

The doses of VIP (Bachem, H-3775) infused are 2.0, 6.0, 20.0, 60.0 μg/kg i.v. and are infused in a volume of 0.5 ml of saline. VIP is infused using a Harvard 22 pump, infusing at 500 μl/min via a 3-way tap into the femoral vein. After VIP infusion, the catheter is flushed with heparinised saline (Hepsaline) so that no VIP is left in the catheter.

For experiments using VIP infusions, there is a need for an initial sensitising dose response curve (2–60 μg/kg), in order that reproducible responses are obtained. An initial infusion of Hepsaline (50 UI/ml) is infused to act as a negative control.

Infusion of Inhibitors

SEP inhibitors and vehicle controls are infused at the same rate as VIP. SEP inhibitors are left for 30 minutes prior to a VIP dose response curve, and left for 15 minutes prior to pelvic nerve stimulation.

Data are expressed as mean genital (vagina/clitoris) blood flow±standard error of the mean (s.e.m.). Significant changes are identified using Student's t-tests.

Male Sexual Dysfunction Animal Model

Anaesthetised Rabbit Methodology

Male New Zealand rabbits (~2.5 kg) are pre-medicated with a combination of Medetomidine (Domitor®) 0.5 ml/kg i.m., and Ketamine (Vetalar®) 0.25 ml/kg i.m. whilst maintaining oxygen intake via a face mask. The rabbits are tracheotomised using a Portex™ uncuffed endotracheal tube 3 ID., connected to a ventilator and maintained at a ventilation rate of 30–40 breaths per minute, with an approximate tidal volume of 18–20 ml, and a maximum airway pressure of 10 cm $H_2O$. Anaesthesia is then switched to Isoflurane and ventilation continued with $O_2$ at 2 l/min. The right marginal ear vein is cannulated using a 23G or 24G catheter, and Lactated Ringer solution perfused at 0.5 ml/min. The rabbit is maintained at 3% Isoflurane during invasive surgery, dropping to 2% for maintenance anaesthesia.

Cannulation of Vessels

The left groin area of the rabbit is shaved and a vertical incision is made approximately 5 cm in length along the thigh. The femoral vein is exposed, isolated and then cannulated with a PVC catheter (17G; Portex Limited) for the infusion of drugs and compounds. Alternatively, or in addition, the left jugular vein is exposed, isolated and then cannulated with a PVC catheter (17G; Portex Limited) for the infusion of drugs and compounds. Cannulation is repeated for the femoral artery, inserting the catheter to a depth of 10 cm to ensure that the catheter reaches the abdominal aorta. This arterial catheter is linked to a Gould system to record blood pressure. Samples for blood gas analysis are also taken via the arterial catheter. Systolic and diastolic pressures are measured, and the mean arterial pressure calculated using the formula [(diastolic x2+systolic)÷3]. Heart rate is measured via the pulse oxymeter and Po-ne-mah data acquisition software system (Ponemah Physiology Platform, Gould Instrument Systems, Inc.).

Stimulation of the Pelvic Nerve

A ventral midline incision is made into the abdominal cavity. The incision is about 5 cm in length just above the pubis. The fat and muscle is bluntly dissected away to reveal the hypogastric nerve which runs down the body cavity. It is essential to keep close to the side curve of the pubis wall in order to avoid damaging the femoral vein and artery which lie above the pubis. The sciatic and pelvic nerves lie deeper and are located after further dissection on the dorsal side of the rabbit. Once the sciatic nerve is identified, the pelvic nerve is easily located. The term pelvic nerve is loosely applied; anatomy books on the subject fail to identify the nerves in sufficient detail. However, stimulation of the nerve causes an increase in intracavernosal pressure and cavernosal blood flow, and innervation of the pelvic region. The pelvic nerve is freed away from surrounding tissue and a Harvard bipolar stimulating electrode is placed around the nerve. The nerve is slightly lifted to give some tension, then the electrode is secured in position. Approximately 1 ml of light paraffin oil is placed around the nerve and electrode. This acts as a protective lubricant to the nerve and prevents blood contamination of the electrode. The electrode is connected to a Grass S88 Stimulator. The pelvic nerve is stimulated using the following parameters: 5V, pulse width 0.5 ms, duration of stimulus 20 seconds with a frequency of 16 Hz. Reproducible responses are obtained when the nerve is stimulated every 15–20 minutes.

Several stimulations using the above parameters are performed to establish a mean control response. The compound (s) to be tested are infused, via the jugular vein, using a Harvard 22 infusion pump allowing a continuous 15 minute stimulation cycle. The skin and connective tissue around the penis is removed to expose the penis. A catheter set (Insyte-W, Becton-Dickinson 20 Gauge 1.1×48 mm, Beckton-Dickinson) is inserted through the tunica albica into the left corpus cavernosal space and the needle removed, leaving a flexible catheter. This catheter is linked via a pressure transducer (Ohmeda 5299-04) to a Gould system to record intracavernosal pressure. Once an intracavernosal pressure is established, the catheter is sealed in place using Vetbond (tissue adhesive, 3M). Heart rate is measured via the pulse oxymeter and Po-ne-mah data acquisition software system (Ponemah Physiology Platform, Gould Instrument Systems, Inc.).

Intracavernosal blood flow is recorded either as numbers directly from the Flowmeter using Po-ne-mah data acquisition software (Ponemah Physiology Platform, Gould Instrument Systems, Inc.), or indirectly from Gould chart recorder trace. Calibration is set at the beginning of the experiment (0–125 ml/min/100 g tissue).

Infusion of Inhibitors

The SEP inhibitor and vehicle controls are infused at a rate of 0.1 ml/second. SEP inhibitors are left for 15 minutes prior to pelvic nerve stimulation.

Data are expressed as mean intracavernosal blood pressure±s.e.m. Significant changes are identified using Student's t-tests.

What is claimed is:

1. An isolated and/or purified polynucleotide comprising one or more of:
   (a) a polynucleotide encoding a polypeptide comprising the amino acid sequence of SEQ ID NO: 2;
   (b) a polynucleotide comprising a nucleotide sequence of SEQ ID NO: 1 or SEQ ID NO: 5;
   (c) a polynucleotide encoding a soluble secreted endopeptidase (SEP) polypeptide encoded by the human cDNA contained in NCIMB 41110;
   (d) a polynucleotide comprising a nucleotide sequence that has at least 95% identity to the polynucleotide of (a) (b) or (c) and which encodes a naturally occurring SEP that cleaves the synthetic peptide substrate comprising the amino acid sequence of SEQ ID NO: 8 at the Arg-Val bond; or
   (e) the full complement to the polynucleotide of any one of (a) to (d);

and wherein said isolated and/or purified polynucleotide is not genomic.

2. The polynucleotide of claim 1 which encodes human (SEP).

3. A process for producing a polypeptide encoded by the polynucleotide of claim 1 comprising culturing a host coil transformed or transfected with a vector comprising the polynucleotide of claim 1 in culture medium under conditions sufficient for the expression of said polynucleotide and production of a polypeptide encoded by the polynucleotide of claim 1.

4. Cells deposited under Accession Number NCIMB 41110.

5. A host cell transformed or transfected with a vector comprising the polynucleotide of claim 1, wherein a polynucleotide encoded by the polynucleotide of claim 1 is produced in said host cell.

* * * * *

SEQUENCE LISTING

<160> NUMBER OF SEQ ID NOS: 8

<210> SEQ ID NO 1
<211> LENGTH: 2893
<212> TYPE: DNA
<213> ORGANISM: Homo sapiens -continued

```
<400> SEQUENCE: 1
ggcaccagct cagccccaag ccactgctct cccatcccag tccctggaaa tccacccact      60
tggcccagct cacccaact ccaacccact gggacccagt ctccaggggc ctgactgtgg      120
gcggcagcca ctcctgagtg agcaaaggtt cctccgcggt gctctcccgt ccagagccct      180
gctgatgggg aagtccgaag gccccgtggg gatggtggag agcgctggcc gtgcagggca      240
gaagcgcccg gggttcctgg aggggggggct gctgctgctg ctgctgctgg tgaccgctgc      300
cctggtggcc ttgggtgtcc tctacgccga ccgcagaggg aagcagctgc acgccttgc      360 tagccggctg tgcttcttac aggaggagag gacctttgta aaacgaaaac cccgagggat      420
cccagaggcc aagaggtga gcgaggtctg caccacccct gctgcgtga tagcagctgc      480 caggatcctc cagaacatgg acccgaccac ggaaccgtgt gacgacttct accagtttgc      540
atgcggaggc tggctgcggc gccacgtgat ccctgagacc aactcaagat acagcatctt      600
tgacgtcctc cgcgacgagc tggaggtcat cctcaaagcg gtgctggaga attcgactgc      660
caaggaccgg ccggctgtgg agaaggccag gacgctgtac cgctcctgca tgaaccagag      720
tgtgatagag aagcgaggct ctcagcccct gctggacatc ttggaggtgg tgggaggctg      780
gccggtggcg atggacaggt ggaacgagac cgtaggactc gagtgggagc tggagcggca      840
gctggcgctg atgaactcac agttcaacag gcgcgtcctc atcgacctct tcatctggaa      900
cgacgaccag aactccagcc ggcacatcat ctacatagac cagcccacct tgggcatgcc      960
ctcccgagag tactacttca acggcggcag caaccggaag gtgcgggaag cctacctgca      1020
gttcatggtg tcagtggcca cgttgctgcg ggaggatgca aacctgccca gggacagctg      1080
cctggtgcag gaggacatgg tgcaggtgct ggagctggag acacagctgg ccaaggccac      1140 ggtacccag gaggagagac acgacgtcat cgccttgtac caccggatgg gactggagga      1200
gctgcaaagc cagtttggcc tgaagggatt taactggact ctgttcatac aaactgtgct      1260
atcctctgtc aaaatcaagc tgctgccaga tgaggaagtg gtggtctatg catccccta      1320 cctgcagaac cttgaaaaca tcatcgacac ctactcagcc aggaccatac agaactacct      1380
ggtctggcgc ctggtgctgg accgcattgg tagcctaagc cagagattca aggacacacg      1440
agtgaactac cgcaaggcgc tgtttggcac aatggtggag gaggtgcgct ggcgtgaatg      1500
tgtgggctac gtcaacagca acatggagaa cgccgtgggc tccctctacg tcagggaggc      1560
gttccctgga gacagcaaga gcatggtcag agaactcatt gacaaggtgc ggacagtgtt      1620
tgtggagacg ctggacgagc tgggctggat ggacgaggag tccaagaaga aggcgcagga      1680
gaaggccatg agcatccggg agcagatcgg gcaccctgac tacatcctgg aggagatgaa      1740
caggcgcctg gacgaggagt actccaatct gaacttctca gaggacctgt actttgagaa      1800
cagtctgcag aacctcaagg tgggcgccca gcggagcctc aggaagcttc gggaaaaggt      1860
ggacccaaat ctctggatca tcgggggcggc ggtggtcaat cgttctact ccccaaaccg      1920 aaaccagatt gtattccctg ccgggatcct ccagcccccc ttcttcagca aggagcagcc      1980
acaggccttg aactttggag gcattgggat ggtgatcggg cacgagatca cgcacggctt      2040
tgacgacaat ggccggaact tcgacaagaa tggcaacatg atggattggt ggagtaactt      2100
ctccacccag cacttccggg agcagtcaga gtgcatgatc taccagtacg caactactc      2160 ctgggacctg gcagacgaac agaacgtgaa cggattcaac acccttgggg aaaacattgc      2220
tgacaacgga ggggtgcggc aagcctataa ggcctacctc aagtgatgg cagagggtgg      2280 caaggaccag cagctgcccg gcctggatct cacccatgag cagctcttct tcatcaacta      2340
```

-continued

```
tgcccaggtg tggtgcgggt cctaccggcc cgagttcgcc atccaatcca tcaagacaga    2400
cgtccacagt ccctgaagt acagggtact ggggtcgctg cagaacctgg ccgccttcgc    2460
agacacgttc cactgtgccc ggggcacccc catgcacccc aaggagcgat gccgcgtgtg    2520
gtagccaagg ccctgccgcg ctgtgcggcc cacgcccacc tgctgctcgg aggcatctgt    2580
gcgaaggtgc agctagcggc gacccagtgt acgtcccgcc ccggccaacc atgccaagcc    2640
tgcctgccag gcctctgcgc ctggcctagg gtgcagccac ctgcctgaca cccagggatg    2700
agcagtgtcc agtgcagtac ctggaccgga gcccctcca cagacacccg cggggctcag    2760 tgccccgtc acagctctgt agagacaatc aactgtgtcc tgcccaccct ccaaggtgca    2820
ttgtcttcca gtatctacag cttcagactt gagctaagta aatgcttcaa agaaaaaaaa    2880
aaaaaaaaaa aaa                                                       2893
```

<210> SEQ ID NO 2
<211> LENGTH: 779
<212> TYPE: PRT
<213> ORGANISM: Homo sapiens

<400> SEQUENCE: 2

```
Met Gly Lys Ser Glu Gly Pro Val Gly Met Val Glu Ser Ala Gly Arg
 1               5                  10                  15

Ala Gly Gln Lys Arg Pro Gly Phe Leu Glu Gly Gly Leu Leu Leu Leu
            20                  25                  30

Leu Leu Leu Val Thr Ala Ala Leu Val Ala Leu Gly Val Leu Tyr Ala
        35                  40                  45

Asp Arg Arg Gly Lys Gln Leu Pro Arg Leu Ala Ser Arg Leu Cys Phe
    50                  55                  60

Leu Gln Glu Glu Arg Thr Phe Val Lys Arg Lys Pro Arg Gly Ile Pro
65                  70                  75                  80

Glu Ala Gln Glu Val Ser Glu Val Cys Thr Thr Pro Gly Cys Val Ile
                85                  90                  95

Ala Ala Ala Arg Ile Leu Gln Asn Met Asp Pro Thr Thr Glu Pro Cys
            100                 105                 110

Asp Asp Phe Tyr Gln Phe Ala Cys Gly Gly Trp Leu Arg Arg His Val
        115                 120                 125

Ile Pro Glu Thr Asn Ser Arg Tyr Ser Ile Phe Asp Val Leu Arg Asp
    130                 135                 140

Glu Leu Glu Val Ile Leu Lys Ala Val Leu Glu Asn Ser Thr Ala Lys
145                 150                 155                 160

Asp Arg Pro Ala Val Glu Lys Ala Arg Thr Leu Tyr Arg Ser Cys Met
                165                 170                 175

Asn Gln Ser Val Ile Glu Lys Arg Gly Ser Gln Pro Leu Leu Asp Ile
            180                 185                 190

Leu Glu Val Val Gly Gly Trp Pro Val Ala Met Asp Arg Trp Asn Glu
        195                 200                 205

Thr Val Gly Leu Glu Trp Glu Leu Glu Arg Gln Leu Ala Leu Met Asn
    210                 215                 220

Ser Gln Phe Asn Arg Arg Val Leu Ile Asp Leu Phe Ile Trp Asn Asp
225                 230                 235                 240

Asp Gln Asn Ser Ser Arg His Ile Ile Tyr Ile Asp Gln Pro Thr Leu
                245                 250                 255

Gly Met Pro Ser Arg Glu Tyr Tyr Phe Asn Gly Gly Ser Asn Arg Lys
            260                 265                 270
```

-continued

```
Val Arg Glu Ala Tyr Leu Gln Phe Met Val Ser Val Ala Thr Leu Leu
        275                 280                 285

Arg Glu Asp Ala Asn Leu Pro Arg Asp Ser Cys Leu Val Gln Glu Asp
    290                 295                 300

Met Val Gln Val Leu Glu Leu Glu Thr Gln Leu Ala Lys Ala Thr Val
305                 310                 315                 320

Pro Gln Glu Glu Arg His Asp Val Ile Ala Leu Tyr His Arg Met Gly
                325                 330                 335

Leu Glu Glu Leu Gln Ser Gln Phe Gly Leu Lys Gly Phe Asn Trp Thr
            340                 345                 350

Leu Phe Ile Gln Thr Val Leu Ser Val Lys Ile Lys Leu Leu Pro
        355                 360                 365

Asp Glu Glu Val Val Tyr Gly Ile Pro Tyr Leu Gln Asn Leu Glu
    370                 375                 380

Asn Ile Ile Asp Thr Tyr Ser Ala Arg Thr Ile Gln Asn Tyr Leu Val
385                 390                 395                 400

Trp Arg Leu Val Leu Asp Arg Ile Gly Ser Leu Ser Gln Arg Phe Lys
                405                 410                 415

Asp Thr Arg Val Asn Tyr Arg Lys Ala Leu Phe Gly Thr Met Val Glu
            420                 425                 430

Glu Val Arg Trp Arg Glu Cys Val Gly Tyr Val Asn Ser Asn Met Glu
        435                 440                 445

Asn Ala Val Gly Ser Leu Tyr Val Arg Glu Ala Phe Pro Gly Asp Ser
    450                 455                 460

Lys Ser Met Val Arg Glu Leu Ile Asp Lys Val Arg Thr Val Phe Val
465                 470                 475                 480

Glu Thr Leu Asp Glu Leu Gly Trp Met Asp Glu Glu Ser Lys Lys Lys
                485                 490                 495

Ala Gln Glu Lys Ala Met Ser Ile Arg Glu Gln Ile Gly His Pro Asp
            500                 505                 510

Tyr Ile Leu Glu Glu Met Asn Arg Arg Leu Asp Glu Glu Tyr Ser Asn
        515                 520                 525

Leu Asn Phe Ser Glu Asp Leu Tyr Phe Glu Asn Ser Leu Gln Asn Leu
    530                 535                 540

Lys Val Gly Ala Gln Arg Ser Leu Arg Lys Leu Arg Glu Lys Val Asp
545                 550                 555                 560

Pro Asn Leu Trp Ile Ile Gly Ala Ala Val Val Asn Ala Phe Tyr Ser
                565                 570                 575

Pro Asn Arg Asn Gln Ile Val Phe Pro Ala Gly Ile Leu Gln Pro Pro
            580                 585                 590

Phe Phe Ser Lys Glu Gln Pro Gln Ala Leu Asn Phe Gly Gly Ile Gly
        595                 600                 605

Met Val Ile Gly His Glu Ile Thr His Gly Phe Asp Asp Asn Gly Arg
    610                 615                 620

Asn Phe Asp Lys Asn Gly Asn Met Met Asp Trp Trp Ser Asn Phe Ser
625                 630                 635                 640

Thr Gln His Phe Arg Glu Gln Ser Glu Cys Met Ile Tyr Gln Tyr Gly
                645                 650                 655

Asn Tyr Ser Trp Asp Leu Ala Asp Glu Gln Asn Val Asn Gly Phe Asn
            660                 665                 670

Thr Leu Gly Glu Asn Ile Ala Asp Asn Gly Gly Val Arg Gln Ala Tyr
        675                 680                 685
```

```
Lys Ala Tyr Leu Lys Trp Met Ala Glu Gly Gly Lys Asp Gln Gln Leu
            690                 695                 700
Pro Gly Leu Asp Leu Thr His Glu Gln Leu Phe Phe Ile Asn Tyr Ala
705                 710                 715                 720
Gln Val Trp Cys Gly Ser Tyr Arg Pro Glu Phe Ala Ile Gln Ser Ile
                725                 730                 735
Lys Thr Asp Val His Ser Pro Leu Lys Tyr Arg Val Leu Gly Ser Leu
            740                 745                 750
Gln Asn Leu Ala Ala Phe Ala Asp Thr Phe His Cys Ala Arg Gly Thr
        755                 760                 765
Pro Met His Pro Lys Glu Arg Cys Arg Val Trp
    770                 775
```

<210> SEQ ID NO 3
<211> LENGTH: 20
<212> TYPE: DNA
<213> ORGANISM: Homo sapiens

<400> SEQUENCE: 3

| | |
|---|---|
| ctgtcttgat ggattggatg | 20 |

<210> SEQ ID NO 4
<211> LENGTH: 22
<212> TYPE: DNA
<213> ORGANISM: Homo sapiens

<400> SEQUENCE: 4

| | |
|---|---|
| gtccttggca gtcgaattct cc | 22 |

<210> SEQ ID NO 5
<211> LENGTH: 2975
<212> TYPE: DNA
<213> ORGANISM: Homo sapiens

<400> SEQUENCE: 5

| | |
|---|---|
| cagagctcgt ttagtgaacc gtcagaattt tgtaatacga ctcactatag ggcggccgcg | 60 |
| aattcggcac cagctcagcc ccaagccact gctctcccat cccagtccct ggaaatccac | 120 |
| ccacttggcc cagctcaccc caactccaac ccactgggac ccagtctcca ggggcctgac | 180 |
| tgtgggcggc agccactcct gagtgagcaa aggttcctcc gcggtgctct cccgtccaga | 240 |
| gccctgctga tggggaagtc cgaaggcccc gtggggatgg tggagagcgc tggccgtgca | 300 |
| gggcagaagc gcccggggtt cctggagggg gggctgctgc tgctgctgct gctggtgacc | 360 |
| gctgccctgg tggccttggg tgtcctctac gccgaccgca gagggaagca gctgccacgc | 420 |
| cttgctagcc ggctgtgctt cttacaggag gagaggacct tgtaaaacg aaaacccga | 480 |
| gggatcccag aggcccaaga ggtgagcgag gtctgcacca ccctggctg cgtgatagca | 540 |
| gctgccagga tcctccagaa catggacccg accacgaac cgtgtgacga cttctaccag | 600 |
| tttgcatgcg gaggctggct gcggcgccac gtgatccctg agaccaactc aagatacagc | 660 |
| atctttgacg tcctccgcga cgagctggag gtcatcctca aagcggtgct ggagaattcg | 720 |
| actgccaagg accggccggc tgtggagaag gccaggacgc tgtaccgctc ctgcatgaac | 780 |
| cagagtgtga tagagaagcg aggctctcag cccctgctgg acatcttgga ggtggtggga | 840 |
| ggctggccgg tggcgatgga caggtggaac gagaccgtag gactcgagtg ggagctggag | 900 |
| cggcagctgg cgctgatgaa ctcacagttc aacaggcgcg tcctcatcga cctcttcatc | 960 |
| tggaacgacg accagaactc cagccggcac atcatctaca gaccagcc cacccttggc | 1020 |

```
                                    -continued atgccctccc gagagtacta cttcaacggc ggcagcaacc ggaaggtgcg ggaagcctac    1080
ctgcagttca tggtgtcagt ggccacgttg ctgcgggagg atgcaaacct gcccagggac    1140
agctgcctgg tgcaggagga catggtgcag gtgctggagc tggagacaca gctggccaag    1200
gccacggtac cccaggagga gagacacgac gtcatcgcct tgtaccaccg gatgggactg    1260
gaggagctgc aaagccagtt tggcctgaag ggatttaact ggactctgtt catacaaact    1320
gtgctatcct ctgtcaaaat caagctgctg ccagatgagg aagtggtggt ctatggcatc    1380
ccctacctgc agaaccttga aaacatcatc gacaccctact cagccaggac catacagaac    1440
tacctggtct ggcgcctggt gctggaccgc attggtagcc taagccagag attcaaggac    1500
acacgagtga actaccgcaa ggcgctgttt ggcacaatgg tggaggaggt gcgctggcgt    1560
gaatgtgtgg gctacgtcaa cagcaacatg gagaacgccg tgggctccct ctacgtcagg    1620
gaggcgttcc ctggagacag caagagcatg gtcagagaac tcattgacaa ggtgcggaca    1680
gtgtttgtgg agacgctgga cgagctgggc tggatggacg aggagtccaa gaagaaggcg    1740
caggagaagg ccatgagcat ccgggagcag atcgggcacc ctgactacat cctggaggag    1800
atgaacaggc gcctggacga ggagtactcc aatctgaact tctcagagga cctgtacttt    1860
gagaacagtc tgcagaacct caaggtgggc gcccagcgga gcctcaggaa gcttcgggaa    1920
aaggtggacc caaatctctg gatcatcggg gcggcggtgg tcaatgcgtt ctactcccca    1980
aaccgaaacc agattgtatt ccctgccggg atcctccagc ccccttctt cagcaaggag    2040 cagccacagg ccttgaactt tggaggcatt gggatggtga tcgggcacga gatcacgcac    2100
ggctttgacg acaatggccg gaacttcgac aagaatggca acatgatgga ttggtggagt    2160
aacttctcca cccagcactt ccgggagcag tcagagtgca tgatctacca gtacggcaac    2220
tactcctggg acctggcaga cgaacagaac gtgaacggat tcaacaccct tggggaaaac    2280
attgctgaca acggagggt gcggcaagcc tataaggcct acctcaagtg gatggcagag    2340
ggtggcaagg accagcagct gcccggcctg gatctcaccc atgagcagct cttcttcatc    2400
aactatgccc aggtgtggtg cggtgtcctac cggcccgagt tcgccatcca atccatcaag    2460
acagacgtcc acagtcccct gaagtacagg gtactggggt cgctgcagaa cctggccgcc    2520
ttcgcagaca cgttccactg tgcccggggc accccccatgc acccccaagga gcgatgccgc    2580 gtgtggtagc caaggccctg ccgcgctgtg cggcccacgc ccacctgctg ctcggaggca    2640
tctgtgcgaa ggtgcagcta gcggcgaccc agtgtacgtc ccgccccggc caaccatgcc    2700
aagcctgcct gccaggcctc tgcgcctggc ctagggtgca gccacctgcc tgacacccag    2760
ggatgagcag tgtccagtgc agtacctgga ccggagcccc ctccacagac acccgcgggg    2820
ctcagtgccc ccgtcacagc tctgtagaga caatcaactg tgtcctgccc accctccaag    2880
gtgcattgtc ttccagtatc tacagcttca gacttgagct aagtaaatgc ttcaaagaaa    2940
aaaaaaaaaa aaaaaaaact cgactctaga ttgcg                              2975
```

<210> SEQ ID NO 6
<211> LENGTH: 9
<212> TYPE: PRT
<213> ORGANISM: Homo sapiens

<400> SEQUENCE: 6

Met Gly Lys Ser Glu Gly Pro Val Gly
1               5

```
<210> SEQ ID NO 7
<211> LENGTH: 26
<212> TYPE: DNA
<213> ORGANISM: Homo sapiens

<400> SEQUENCE: 7
atggggaagt ccgaaggccc cgtggg                                   26

<210> SEQ ID NO 8
<211> LENGTH: 9
<212> TYPE: PRT
<213> ORGANISM: synthetic construct

<400> SEQUENCE: 8

Gly Gly Phe Leu Arg Arg Val Cys Ala
1               5
```